(12) United States Patent
Vicker et al.

(10) Patent No.: US 8,558,028 B2
(45) Date of Patent: Oct. 15, 2013

(54) COMPOUND CAPABLE OF INHIBITING 17-BETA HYDROXYSTERIOD DEHYDROGENASE

(75) Inventors: Nigel Vicker, Slough (GB); Helen Victoria Bailey, Slough (GB); Wesley Heaton, Slough (GB); Joanna Mary Day, Slough (GB); Atul Purohit, Slough (GB); Barry Victor Lloyd Potter, Slough (GB)

(73) Assignee: University of Bath of Claverton Down, Bath (GB)

( * ) Notice: Subject to any disclaimer, the term of this patent is extended or adjusted under 35 U.S.C. 154(b) by 52 days.

(21) Appl. No.: 12/744,044

(22) PCT Filed: Nov. 19, 2008

(86) PCT No.: PCT/GB2008/003889
§ 371 (c)(1), (2), (4) Date: Jul. 29, 2010

(87) PCT Pub. No.: WO2009/066072
PCT Pub. Date: May 28, 2009

(65) Prior Publication Data
US 2010/0286204 A1    Nov. 11, 2010

(30) Foreign Application Priority Data
Nov. 20, 2007   (GB) .................................. 0722779.6

(51) Int. Cl.
*A61K 31/125* (2006.01)
*C07C 213/00* (2006.01)

(52) U.S. Cl.
USPC .......................................... 564/430; 514/648

(58) Field of Classification Search
None
See application file for complete search history.

(56) References Cited

U.S. PATENT DOCUMENTS

| | | | |
|---|---|---|---|
| 6,476,056 B2 * | 11/2002 | Nakazato et al. | .............. 514/351 |
| 6,541,463 B1 | 4/2003 | Labrie et al. | |
| 2006/0135619 A1 | 6/2006 | Kick et al. | |
| 2008/0031823 A1 | 2/2008 | Bornhop et al. | |

FOREIGN PATENT DOCUMENTS

| | | |
|---|---|---|
| EP | 1 004 573 | 5/2000 |
| EP | 1 123 918 | 8/2001 |
| EP | 1 854 781 | 11/2007 |
| WO | WO 86/01105 | 2/1986 |
| WO | WO 90/10462 | 9/1990 |
| WO | WO 91/00731 | 1/1991 |
| WO | WO 91/00733 | 1/1991 |
| WO | WO 94/26767 | 11/1994 |
| WO | WO 96/26201 | 8/1996 |
| WO | WO 97/11162 | 3/1997 |
| WO | WO 98/05635 | 2/1998 |
| WO | WO 98/07859 | 2/1998 |
| WO | WO 98/08870 | 3/1998 |
| WO | WO 98/09985 | 3/1998 |
| WO | 98/13348 | 4/1998 |
| WO | WO 98/30556 | 7/1998 |
| WO | WO 98/32724 | 7/1998 |
| WO | WO 98/45757 | 10/1998 |
| WO | WO 99/12540 | 3/1999 |
| WO | WO 99/46279 | 9/1999 |
| WO | WO 99/52890 | 10/1999 |

(Continued)

OTHER PUBLICATIONS

CAPLUS 1998:631744.*

(Continued)

*Primary Examiner* — Janet Andres
*Assistant Examiner* — Heidi Reese
(74) *Attorney, Agent, or Firm* — Hunton & Williams LLP

(57) ABSTRACT

There is provided a compound having Formula I

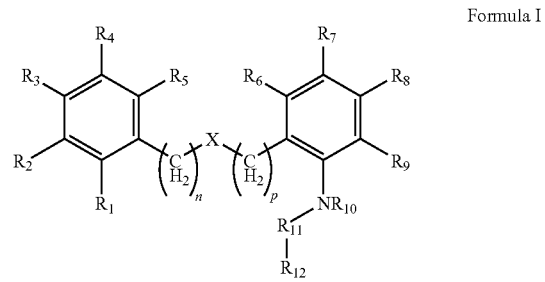

Formula I wherein
each of $R_1$, $R_2$, $R_3$, $R_4$, $R_5$, $R_6$, $R_7$, $R_8$ and $R_9$ are independently selected from
(a) H, (b) $R_{13}$, —$OC(R_{13})_3$, —$OCH(R_{13})_2$, —$OCH_2R_{13}$, $C(R_{13})_3$, —$CH(R_{13})_2$, or —$CH_2R_{13}$ wherein $R_{13}$ is a halogen; (c) —CN; (d) optionally substituted alkyl, (e) optionally substituted heteroalkyl; (f) optionally substituted aryl; (g) optionally substituted heteroaryl; (h) optionally substituted arylalkyl; (i) optionally substituted heteroarylalkyl; (j) hydroxy; (k) alkoxy; (l) aryloxy; (m) —$SO_2$-alkyl; and (n) —$N(R_{14})C(O)R_{15}$,
wherein $R_{14}$ and $R_{15}$ are independently selected from H and hydrocarbyl,
wherein the optional substituents of (d) (e) (f) (h) and (i) are selected from the group consisting of: $C_{1-6}$ alkyl, halo, cyano, nitro, haloalkyl, hydroxy, $C_{1-6}$ alkoxy, carboxy, carboxyalkyl, carboxamide, mercapto, amino, alkylamino, dialkylamino, sulfonyl, sulfonamido, aryl and heteroaryl;
wherein n and p are independently selected from 0 and 1;
X is an optional group selected from O, S, S=0, $S(=O)_2$, C=O, $S(=O)_2NR_{16}$, C=$ONR_{17}$, $NR_{18}$, in which $R_{16}$, $R_{17}$, and $R_{18}$ are independently selected from H and hydrocarbyl,
$R_{10}$ is selected from H and hydrocarbyl,
$R_{11}$ is selected from $CR_{19}R_{20}$ and C=O, in which $R_{19}$ and $R_{20}$ are independently selected from H and hydrocarbyl,
$R_{12}$ is selected from a substituted five or six membered carbon rings optionally containing one or more hetero atoms selected from N, S, and O and optionally having fused thereto a further ring, and wherein the one or more substituents are selected from hydrocarbyl groups.

44 Claims, No Drawings

(56) References Cited

FOREIGN PATENT DOCUMENTS

| WO | WO 01/42181 | 6/2001 |
| WO | WO 03/03347 | 1/2003 |
| WO | WO 2004/110459 | 12/2004 |
| WO | WO 2007/003934 | 1/2007 |
| WO | WO 2007/096647 | 8/2007 |

OTHER PUBLICATIONS

Bai, M. et al., Bioconjugate Chemistry, vol. 18, No. 6, pp. 2018-2023, XP002523882 (2007).
Geissler, W.M. et al., Nat. Genet., vol. 7, pp. 34-39 (1994).
Labrie et al., Trends Endocrinol Metab., vol. 11, pp. 421-427 (2000).
Labrie, F. et al., Steroids, vol. 62, pp. 148-158 (1997).
Lodish et al., Molecular Cell Biology, $3^{rd}$ Edition, pp. 177-181 (1995).
Oefelein, M.G. & Coornum, R., Journal of Urology, vol. 164, pp. 726-729 (2000).
Poirier, D. Current Med. Chem., vol. 10, pp. 453-477 (2003).
International Search Report for International Patent Application No. PCT/GB2008/003889 mailed on Aug. 19, 2009.
Written Opinion for International Patent Application No. PCT/GB2008/003889 mailed on Aug. 19, 2009.
International Preliminary Report on Patentability for International Patent Application No. PCT/GB2008/003889 mailed Jun. 3, 2010.

* cited by examiner

COMPOUND CAPABLE OF INHIBITING 17-BETA HYDROXYSTERIOD DEHYDROGENASE

This application is a national phase filing of International Patent Application No. PCT/GB2008/003889, filed Nov. 19, 2008, which claims priority to GB 0722779.6, filed Nov. 20, 2007, the disclosures of each are hereby incorporated by reference in its entirety.

FIELD OF INVENTION

The present invention relates to a compound. In particular the present invention provides compounds capable of inhibiting 17β-hydroxysteroid dehydrogenase Type 3 (17β-HSD3).

BACKGROUND

As discussed in WO03/03347, WO04/110459 and WO99/46279 androgen-dependent diseases, i.e. diseases whose onset or progress is aided by androgenic activity, are well known. These diseases include, but are not limited to, prostate cancer, other androgen-dependent neoplasms such as prostatic intraepithelial neoplasia, benign prostatic hyperplasia, acne, seborrhea, hirsutism, androgenic alopecia, precocious puberty, adrenal hyperplasia and polycystic ovarian syndrome. Estrogen-dependent diseases, i.e. diseases whose onset or progress is aided by estrogenic activity, are also well known. These include but are not limited to breast cancer, endometriosis, leiomyoma and precocious puberty. Androgenic and estrogenic activity may be suppressed by administering androgen receptor antagonists or estrogen receptor antagonists respectively, see for example WO 94/26767 and WO 96/26201. Androgenic and estrogenic activity may also be reduced by suppressing ovarian or testicular secretions by known methods, see for example WO 90/10462, WO 91/00731, WO 91/00733, and WO86/01105. Examples of such anti-androgenic agents include LHRH agonists (e.g. leuprolide and zoladex) and LHRH antagonists (e.g. abarelix and cetrorelix).

Androgenic and estrogenic activity may also be reduced by suppressing androgen or estrogen biosynthesis using inhibitors of enzymes that catalyze one or more steps of such biosynthesis. These include inhibitors of 5alpha-reductase Type 1 and/or Type 2 (for example. finasteride, SKF105,657, LY191,704, LY320,236, dutasteride, Flutamide, nicalutamide, bicalutamide); inhibitors of 17alpha-hydroxylase/C17-20 lyase (for example YM116, CB7630 and liarozole); and inhibitors of 17beta-HSD Types 3 and 5. Inhibitors of 17beta-hydroxysteroid dehydrogenase Type 5 are described in WO 97/11162. Novel inhibitors of both Type 3 and Type 5 17beta-hydroxysteroid dehydrogenase are described in WO 99/46279.

Mammalian 17beta-hydroxysteroid dehydrogenases (17beta-HSDs) are NAD(H) or NADP(H)-dependent enzymes which catalyse, besides other reactions, the final steps in male and female sex hormone biosynthesis. These enzymes convert inactive 17-ketosteroids into their active 17beta-hydroxy forms or catalyze the oxidation of the 17beta-hydroxysteroids into the inactive 17beta-keto forms. Because both estrogens and androgens have the highest affinity for their receptors in the 17beta-hydroxy form, 17beta-HSD enzymes play an essential role in the tissue-selective regulation of the activity of sex steroid hormones.

At present, 11 human members of the 17beta-HSD enzyme family have been described (Types 1-5, 7, 8, and 10-14). The human 17beta-HSD family members share less than 30% similarity in their primary structure. The 17beta-HSDs are expressed in distinct, though in some cases, overlapping patterns. The different types of 17beta-HSDs also differ in their substrate and cofactor specificities. In intact cells in culture, the 17beta-HSDs catalyze the reaction in a unidirectional way: e.g. Types 1, 3, 5 and 7 use NADP (H) as a cofactor and catalyze the reductive reaction (activation), while Types 2, 4, and 8 catalyze the oxidative reaction (inactivation) using NAD (H) as a cofactor (see e.g. Labrie et al. (2000) Trends Endocrinol Metab., 11, 421-7).

Due to their essential role in the tissue-selective regulation of the activity of sex steroid hormones, 17beta-HSDs can be involved in the occurrence and development of both estrogen-sensitive pathologies (e.g. breast, ovarian, uterine and endometrium cancers) and androgen-sensitive pathologies (e.g. prostate cancer, benign prostatic hyperplasia, acne, hirsutism). Furthermore, many types of 17beta-HSD have been shown to be involved in the pathogenesis of particular human disorders. For example, 17beta-HSD3 is known to be involved in the development of pseudohermaphroditism, 17beta-HSD8 plays a role in polycystic kidney disease, and 17beta-HSD4 is implicated in bifunctional enzyme deficiency. Therefore treatment of sex steroid-sensitive disease by administration of specific inhibitors of the 17beta-HSD enzymes has been suggested, optionally in combination with potent and specific anti-estrogens and anti-androgens (Labrie F et al. (1997) Steroids, 62, 148-58).

As each type of 17beta-HSD has a selective substrate affinity, directional (reductive or oxidative) activity in intact cells, and a particular tissue distribution, selectivity of drug action should be achieved by targeting a particular 17beta-HSD enzyme. By individual modulation of the particular 17beta-HSDs it is possible to influence or even control the local and paracrine concentration of estrogens and androgens in different target tissues.

The 17beta-HSD Type 3 enzyme (17beta-HSD3) is a well-characterized member of the 17beta-HSD family. Most of the 17beta-HSDs are expressed in a wide variety of tissues, however the 17beta-HSD3 enzyme is found to be expressed almost exclusively in the testis. 17beta-HSD3 has a crucial role in androgen biosynthesis. It converts 4-androstene-3,17-one (A) to testosterone (T). The physiological significance of 17beta-HSD3 is undeniable. Mutations in the 17beta-HSD3 gene have been found to lead to decreased testosterone formation in the foetal testis, and consequently to a human inter-sex disorder termed male pseudohermaphroditism (Geissler, W. M. et al. (1994) Nat. Genet. 7, 34-9).

Prostate tumours remain androgen-responsive for some time; the presence of active androgens regulates the proliferation and differentiation of the tumour cells. At present, androgen deprivation is the only effective systemic hormonal therapy available for prostate cancer. The development of selective inhibitors of 17beta-HSD3 is a therapeutic approach for the treatment of androgen-dependent disease (Labrie et al. (2000) Trends Endocrinol. Metab. 11, 421-7). Furthermore, Oefelein et al. reported that a GnRH analogue fails, in nearly 20% of cases, to achieve castrated levels of testosterone in men (Oefelein, M. G. & Cornum, R. (2000) J. Urol. 164, 726-9). In order to improve the response rate to endocrine therapy for men with prostate cancer it may be important to selectively inhibit testicular 17beta-HSD3 activity. Besides prostate cancer, many other androgen-sensitive diseases, i.e. diseases whose onset or progress is aided by androgenic activity, may be treated by selectively inhibiting 17beta-HSD3 activity. These diseases include, but are not limited to, benign prostatic hyperplasia, prostatitis, acne, seborrhea, hirsutism, androgenic alopecia, precocious puberty (usually associated with an excess of androgen secretion, often of adrenal origin), adrenal hyperplasia, and polycystic ovarian syndrome (associated with an excess of androgen secretion by the ovaries). Furthermore, considering the fact that 17beta-HSD3 is found mainly in the testis, the development of potent inhibitors could be of interest for blocking spermatogenesis as an anti-fertility agent for males.

Current therapies for the treatment of androgenic and estrogenic-dependent diseases include the use of glucocorticoids to block adrenal secretions, and luteinizing hormone releasing hormone (LHRH) agonists to cause medical castration. Both therapies are associated with undesirable side effects. An improved therapy would include compounds that specifically inhibit Type 3 17beta-hydroxysteroid dehydrogenase, while avoiding inhibition of other 17beta-hydroxysteroid dehydrogenases.

Several reversible or irreversible inhibitors of the 17beta-HSD3 enzymes of steroidal and even non-steroidal origin are already known in the literature. The characteristics of these inhibitory molecules are reviewed in Poirier, D. (2003) Curr. Med. Chem. 10, 453-77. For example, U.S. Pat. No. 6,541,463 discloses androsterone-derived inhibitors for 17beta-HSD3. These derivatives have been synthesised by parallel solid and liquid-phase chemistry, and some of these compounds showed 2 to 18-fold higher inhibitory activity than that of the natural substrate of the enzyme, A-dione, used itself as a inhibitor. Furthermore, WO01/42181 discloses benzyl-tetralins, the chemical structure of which is related to that of the phytoestrogen biochanin, as 17beta-HSD3 inhibitors. Furthermore, WO 98/32724, WO 98/30556 and WO99/12540 disclose tetralone, benzopyrane and benzofuranone derivatives, which have 17beta-HSD inhibitory activity, for the treatment of hormone-sensitive diseases.

There is a need for the development of compounds that selectively inhibit the 17beta-HSD3 enzyme, while desirably failing to substantially inhibit other members of the 17beta-HSD protein family, or other catalysts of sex steroid degradation or activation. In particular, it is an aim of the present invention to develop selective inhibitors of the 17beta-HSD3 enzyme, whereby in addition the compounds have no or only pure antagonistic binding affinities to the androgen receptor.

Aspects of the invention are defined in the appended claims.

SUMMARY OF INVENTION

In one aspect the present invention provides a compound having Formula I

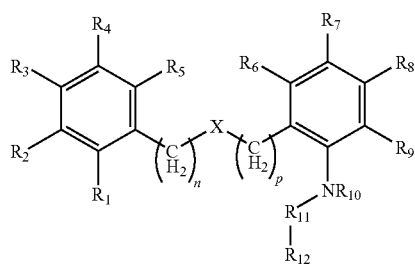

Formula I wherein
each of $R_1$, $R_2$, $R_3$, $R_4$, $R_5$, $R_6$, $R_7$, $R_8$ and $R_9$ are independently selected from (a) H, (b) $R_{13}$, —$OC(R_{13})_3$, —$OCH(R_{13})_2$, —$OCH_2R_{13}$, —$C(R_{13})_3$, —$CH(R_{13})_2$, or —$CH_2R_{13}$ wherein $R_{13}$ is a halogen; (c) —CN; (d) optionally substituted alkyl, (e) optionally substituted heteroalkyl; (f) optionally substituted aryl; (g) optionally substituted heteroaryl; (h) optionally substituted arylalkyl; (i) optionally substituted heteroarylalkyl; (j) hydroxy; (k) alkoxy; (l) aryloxy; (m) —$SO_2$-alkyl; and (n) —$N(R_{14})C(O)R_{15}$, wherein $R_{14}$ and $R_{15}$ are independently selected from H and hydrocarbyl, wherein the optional substituents of (d) (e) (f) (h) and (i) are selected from the group consisting of: $C_{1-6}$ alkyl, halo, cyano, nitro, haloalkyl, hydroxy, $C_{1-6}$ alkoxy, carboxy, carboxyalkyl, carboxamide, mercapto, amino, alkylamino, dialkylamino, sulfonyl, sulfonamido, aryl and heteroaryl;

wherein n and p are independently selected from 0 and 1;
X is an optional group selected from O, S, S=O, $S(=O)_2$, C=O, $S(=O)_2NR_{16}$, $C=ONR_{17}$, $NR_{18}$, in which $R_{16}$, $R_{17}$, and $R_{18}$ are independently selected from H and hydrocarbyl,
$R_{10}$ is selected from H and hydrocarbyl,
$R_{11}$ is selected from $CR_{19}R_{20}$ and C=O, in which $R_{19}$ and $R_{20}$ are independently selected from H and hydrocarbyl,
$R_{12}$ is selected from a substituted five or six membered carbon rings optionally containing one or more hetero atoms selected from N, S, and O and optionally having fused thereto a further ring, and wherein the one or more substituents are selected from hydrocarbyl groups.

In one aspect the present invention provides a pharmaceutical composition comprising (i) a compound having Formula I

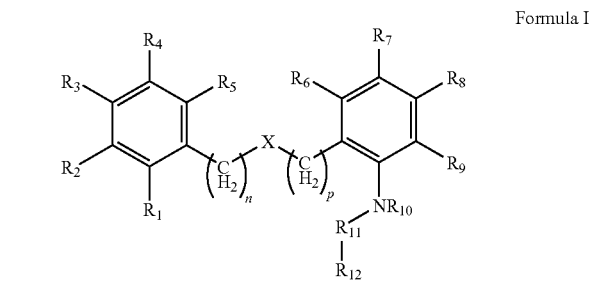

Formula I wherein
each of $R_1$, $R_2$, $R_3$, $R_4$, $R_5$, $R_6$, $R_7$, $R_8$ and $R_9$ are independently selected from (a) H, (b) $R_{13}$, —$OC(R_{13})_3$, —$OCH(R_{13})_2$, —$OCH_2R_{13}$, —$C(R_{13})_3$, —$CH(R_{13})_2$, or —$CH_2R_{13}$ wherein $R_{13}$ is a halogen; (c) —CN; (d) optionally substituted alkyl, (e) optionally substituted heteroalkyl; (f) optionally substituted aryl; (g) optionally substituted heteroaryl; (h) optionally substituted arylalkyl; (i) optionally substituted heteroarylalkyl; (j) hydroxy; (k) alkoxy; (l) aryloxy; (m) —$SO_2$-alkyl; and (n) —$N(R_{14})C(O)R_{15}$, wherein $R_{14}$ and $R_{15}$ are independently selected from H and hydrocarbyl, wherein the optional substituents of (d) (e) (f) (h) and (i) are selected from the group consisting of: $C_{1-6}$ alkyl, halo, cyano, nitro, haloalkyl, hydroxy, $C_{1-6}$ alkoxy, carboxy, carboxyalkyl, carboxamide, mercapto, amino, alkylamino, dialkylamino, sulfonyl, sulfonamido, aryl and heteroaryl;

wherein n and p are independently selected from 0 and 1;
X is an optional group selected from O, S, S=O, $S(=O)_2$, C=O, $S(=O)_2NR_{16}$, $C=ONR_{17}$, $NR_{18}$, in which $R_{16}$, $R_{17}$, and $R_{18}$ are independently selected from H and hydrocarbyl,
$R_{10}$ is selected from H and hydrocarbyl, $R_{11}$ is selected from $CR_{19}R_{20}$ and $C=O$, in which $R_{19}$ and $R_{20}$ are independently selected from H and hydrocarbyl, $R_{12}$ is selected from a substituted five or six membered carbon rings optionally containing one or more hetero atoms selected from N, S, and O and optionally having fused thereto a further ring, and wherein the one or more substituents are selected from hydrocarbyl groups.

(ii) optionally admixed with a pharmaceutically acceptable carrier, diluent, excipient or adjuvant.

In one aspect the present invention provides a compound for use in medicine wherein the compound is of Formula I Formula I wherein
each of $R_1$, $R_2$, $R_3$, $R_4$, $R_5$, $R_6$, $R_7$, $R_8$ and $R_9$ are independently selected from (a) H, (b) $R_{13}$, $-OC(R_{13})_3$, $-OCH(R_{13})_2$, $-OCH_2R_{13}$, $-(R_{13})_3$, $-CH(R_{13})_2$, or $-CH_2R_{13}$ wherein $R_{13}$ is a halogen; (c) $-CN$; (d) optionally substituted alkyl, (e) optionally substituted heteroalkyl; (f) optionally substituted aryl; (g) optionally substituted heteroaryl; (h) optionally substituted arylalkyl; (i) optionally substituted heteroarylalkyl; (j) hydroxy; (k) alkoxy; (l) aryloxy; (m) $-SO_2$-alkyl; and (n) $-N(R_{14})C(O)R_{15}$,
wherein $R_{14}$ and $R_{15}$ are independently selected from H and hydrocarbyl,
wherein the optional substituents of (d) (e) (f) (h) and (i) are selected from the group consisting of: $C_{1-6}$ alkyl, halo, cyano, nitro, haloalkyl, hydroxy, $C_{1-6}$ alkoxy, carboxy, carboxyalkyl, carboxamide, mercapto, amino, alkylamino, dialkylamino, sulfonyl, sulfonamido, aryl and heteroaryl;
wherein n and p are independently selected from 0 and 1;
X is an optional group selected from O, S, S=O, S(=O)$_2$, C=O, S(=O)$_2$NR$_{16}$, C=ONR$_{17}$, NR$_{15}$, in which $R_{16}$, $R_{17}$, and $R_{18}$ are independently selected from H and hydrocarbyl,
$R_{10}$ is selected from H and hydrocarbyl,
$R_{11}$ is selected from $CR_{19}R_{20}$ and C=O, in which $R_{19}$ and $R_{20}$ are independently selected from H and hydrocarbyl,
$R_{12}$ is selected from a substituted five or six membered carbon rings optionally containing one or more hetero atoms selected from N, S, and O and optionally having fused thereto a further ring, and wherein the one or more substituents are selected from hydrocarbyl groups.

In one aspect the present invention provides a use of a compound in the manufacture of a medicament
(i) for use in the therapy of an androgen dependent disease or estrogen dependent disease, or
(ii) for use in the therapy of a condition or disease selected from the group consisting of prostate cancer, androgen dependent neoplasms, benign prostatic hyperplasia, prostatic intraepithelial neoplasia, androgenic alopecia, hirsutism, polycystic ovary syndrome and acne; or
(iii) for use in the therapy of a condition or disease associated with 17β-HSD (preferably 17β-HSD Type 3); or
(iv) for use in the therapy of a condition or disease associated with adverse 17β-HSD (preferably 17β-HSD Type 3) levels; or
(v) for modulating 17β-HSD (preferably 17β-HSD Type 3) activity; or
(vi) for inhibiting 17β-HSD (preferably 17β-HSD Type 3) activity;
wherein the compound has Formula I Formula I wherein
each of $R_1$, $R_2$, $R_3$, $R_4$, $R_5$, $R_6$, $R_7$, $R_8$ and $R_9$ are independently selected from (a) H, (b) $R_{13}$, $-OC(R_{13})_3$, $-OCH(R_{13})_2$, $-OCH_2R_{13}$, $-C(R_{13})_3$, $-CH(R_{13})_2$, or $-CH_2R_{13}$ wherein $R_{13}$ is a halogen; (c) $-CN$; (d) optionally substituted alkyl, (e) optionally substituted heteroalkyl; (f) optionally substituted aryl; (g) optionally substituted heteroaryl; (h) optionally substituted arylalkyl; (i) optionally substituted heteroarylalkyl; (j) hydroxy; (k) alkoxy; (l) aryloxy; (m) $-SO_2$-alkyl; and (n) $-N(R_{14})C(O)R_{15}$,
wherein $R_{14}$ and $R_{15}$ are independently selected from H and hydrocarbyl,
wherein the optional substituents of (d) (e) (f) (h) and (i) are selected from the group consisting of: $C_{1-6}$ alkyl, halo, cyano, nitro, haloalkyl, hydroxy, $C_{1-6}$ alkoxy, carboxy, carboxyalkyl, carboxamide, mercapto, amino, alkylamino, dialkylamino, sulfonyl, sulfonamido, aryl and heteroaryl;
wherein n and p are independently selected from 0 and 1;
X is an optional group selected from O, S, S=O, S(=O)$_2$, C=O, S(=O)$_2$NR$_{16}$, C=ONR$_{17}$, NR$_{18}$, in which $R_{16}$, $R_{17}$, and $R_{18}$ are independently selected from H and hydrocarbyl,
$R_{10}$ is selected from H and hydrocarbyl,
$R_{11}$ is selected from $CR_{19}R_{20}$ and C=O, in which $R_{19}$ and $R_{20}$ are independently selected from H and hydrocarbyl,
$R_{12}$ is selected from a substituted five or six membered carbon rings optionally containing one or more hetero atoms selected from N, S, and O and optionally having fused thereto a further ring, and wherein the one or more substituents are selected from hydrocarbyl groups.

The present invention relates to novel inhibitory compounds of an enzyme involved in the biosynthesis of sex steroids from natural precursors, the 17beta-hydroxysteroid dehydrogenase Type 3 enzyme (17beta-HSD3), to their salts, to pharmaceutical preparations containing these compounds and to processes for the preparation of these compounds. Furthermore, the invention concerns the therapeutic use of said inhibitors, particularly their use in the treatment or prevention of androgen-dependent diseases or disorders, such as diseases or disorders requiring the inhibition of 17beta-HSD Type 3 enzyme, and/or requiring the modulation of the endogenous testosterone concentration. Pharmaceutical use of the inhibitors may reduce the natural production of androgens such as testosterone and dihydrotestosterone, and thereby beneficially treat diseases whose onset or progress is aided by androgenic activity. Because androgens formed by reactions catalyzed by Type 3 enzyme are precursors to estrogens, the invention also has applicability to diseases whose onset or progress is aided by estrogenic activity.

Another advantage of the compounds of the present invention is that they may be potent 17β-HSD inhibitors in vivo.

Some of the compounds of the present invention are also advantageous in that they may be orally active.

DETAILED INVENTION

As previously mentioned, in one aspect the present invention provides a compound having Formula I defined above.

As previously mentioned, in one aspect the present invention provides a pharmaceutical composition comprising
(i) a compound having Formula I defined above
(ii) optionally admixed with a pharmaceutically acceptable carrier, diluent, excipient or adjuvant.

As previously mentioned, in one aspect the present invention provides a compound having Formula I defined above, for use in medicine.

As previously mentioned, in one aspect the present invention provides a compound having Formula I defined above, for use in the therapy of a condition or disease associated with 17β-HSD.

In one aspect the present invention provides a compound having Formula I defined above, for use in the therapy of a condition or disease associated with adverse 17β-HSD levels.

In one aspect the present invention provides a compound having Formula I defined above, for modulating 17β-HSD activity.

In one aspect the present invention provides a compound having Formula I defined above, for inhibiting 17β-HSD activity.

For ease of reference, these and further aspects of the present invention are now discussed under appropriate section headings. However, the teachings under each section are not necessarily limited to each particular section.

As previously mentioned, in one aspect the present invention provides a compound.

In one aspect the present invention provides a compound having Formula I

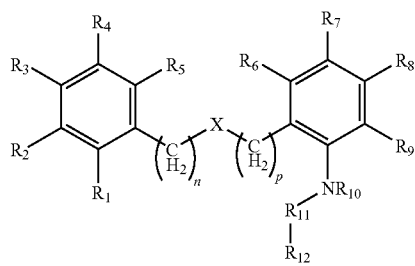

Formula I wherein
each of $R_1$, $R_2$, $R_3$, $R_4$, $R_5$, $R_6$, $R_7$, $R_8$ and $R_9$ are independently selected from
(a) H, (b) $R_{13}$, $-OC(R_{13})_3$, $-OCH(R_{13})_2$, $-OCH_2R_{13}$, $-C(R_{13})_3$, $-CH(R_{13})_2$, or $-CH_2R_{13}$ wherein $R_{13}$ is a halogen; (c) $-CN$; (d) optionally substituted alkyl, (e) optionally substituted heteroalkyl; (f) optionally substituted aryl; (g) optionally substituted heteroaryl; (h) optionally substituted arylalkyl; (i) optionally substituted heteroarylalkyl; (j) hydroxy; (k) alkoxy; (l) aryloxy; (m) $-SO_2$-alkyl; and (n) $-N(R_{14})C(O)R_{15}$, wherein $R_{14}$ and $R_{15}$ are independently selected from H and hydrocarbyl,
wherein the optional substituents of (d) (e) (f) (h) and (i) are selected from the group consisting of: $C_{1-6}$ alkyl, halo, cyano, nitro, haloalkyl, hydroxy, $C_{1-6}$ alkoxy, carboxy, carboxyalkyl, carboxamide, mercapto, amino, alkylamino, dialkylamino, sulfonyl, sulfonamido, aryl and heteroaryl;
wherein n and p are independently selected from 0 and 1;
X is an optional group selected from O, S, S=O, S(=O)$_2$, C=O, S(=O)$_2$NR$_{16}$, C=ONR$_{17}$, NR$_{15}$, in which R$_{16}$, R$_{17}$, and R$_{18}$ are independently selected from H and hydrocarbyl,
$R_{10}$ is selected from H and hydrocarbyl,
$R_{11}$ is selected from CR$_{19}$R$_{20}$ and C=O, in which R$_{19}$ and R$_{20}$ are independently selected from H and hydrocarbyl,
$R_{12}$ is selected from a substituted five or six membered carbon rings optionally containing one or more hetero atoms selected from N, S, and O and optionally having fused thereto a further ring, and wherein the one or more substituents are selected from hydrocarbyl groups.

The term "hydrocarbyl group" as used herein means a group comprising at least C and H and may optionally comprise one or more other suitable substituents. Examples of such substituents may include halo, alkoxy, nitro, an alkyl group, a cyclic group etc. In addition to the possibility of the substituents being a cyclic group, a combination of substituents may form a cyclic group. If the hydrocarbyl group comprises more than one C then those carbons need not necessarily be linked to each other. For example, at least two of the carbons may be linked via a suitable element or group. Thus, the hydrocarbyl group may contain hetero atoms. Suitable hetero atoms will be apparent to those skilled in the art and include, for instance, sulphur, nitrogen and oxygen. A non-limiting example of a hydrocarbyl group is an acyl group.

A typical hydrocarbyl group is a hydrocarbon group. Here the term "hydrocarbon" means any one of an alkyl group, an alkenyl group, an alkynyl group, which groups may be linear, branched or cyclic, or an aryl group. The term hydrocarbon also includes those groups but wherein they have been optionally substituted. If the hydrocarbon is a branched structure having substituent(s) thereon, then the substitution may be on either the hydrocarbon backbone or on the branch; alternatively the substitutions may be on the hydrocarbon backbone and on the branch.

In some aspects of the present invention, one or more hydrocarbyl groups is independently selected from optionally substituted alkyl group, optionally substituted haloalkyl group, aryl group, alkylaryl group, alkylarylakyl group, and an alkene group.

In some aspects of the present invention, one or more hydrocarbyl groups is independently selected from $C_1$-$C_{10}$ alkyl group, such as $C_1$-$C_6$ alkyl group, and $C_1$-$C_3$ alkyl group. Typical alkyl groups include $C_1$ alkyl, $C_2$ alkyl, $C_3$ alkyl, $C_4$ alkyl, $C_5$ alkyl, $C_7$ alkyl, and $C_8$ alkyl.

In some aspects of the present invention, one or more hydrocarbyl groups is independently selected from aryl groups, alkylaryl groups, alkylarylakyl groups, $-(CH_2)_{1-10}$-aryl, $-(CH_2)_{1-10}$-Ph, $(CH_2)_{1-10}$-Ph-$C_{1-10}$ alkyl, $-(CH_2)_{1-5}$-Ph, $(CH_2)_{1-5}$-Ph-$C_{1-5}$ alkyl, $-(CH_2)_{1-3}$-Ph, $(CH_2)_{1-3}$-Ph-$C_{1-3}$ alkyl, $-CH_2$-Ph, and $-CH_2$-Ph-C(CH$_3$)$_3$. The aryl groups may contain a hetero atom. Thus the aryl group or one or more of the aryl groups may be carbocyclic or more may heterocyclic. Typical hetero atoms include O, N and S, in particular N.

In some aspects of the present invention, one or more hydrocarbyl groups is independently selected from $-(CH_2)_{1-10}$-cycloalkyl, $-(CH_2)_{1-10}$-$C_{3-10}$cycloalkyl, —(CH$_2$)$_{1-7}$—C$_{3-7}$cycloalkyl, —(CH$_2$)$_{1-5}$—C$_{3-5}$cycloalkyl, —(CH$_2$)$_{1-3}$—C$_{3-5}$cycloalkyl, and —CH$_2$—C$_3$cycloalkyl.

In some aspects of the present invention, one or more hydrocarbyl groups is independently selected from alkene groups. Typical alkene groups include C$_1$-C$_{10}$ alkene group, C$_1$-C$_6$ alkene group, C$_1$-C$_3$ alkene group, such as C$_1$, C$_2$, C$_3$, C$_4$, C$_5$, C$_6$, or C$_7$ alkene group. In a preferred aspect the alkene group contains 1, 2 or 3 C=C bonds. In a preferred aspect the alkene group contains 1 C=C bond. In some preferred aspect at least one C=C bond or the only C=C bond is to the terminal C of the alkene chain, that is the bond is at the distal end of the chain to the ring system.

In some aspects of the present invention, one or more hydrocarbyl groups is independently selected from oxyhydrocarbyl groups.

One particular hydrocarbyl group is an oxyhydrocarbyl group. The term "oxyhydrocarbyl" group as used herein means a group comprising at least C, H and O and may optionally comprise one or more other suitable substituents. Examples of such substituents may include halo-, alkoxy-, nitro-, an alkyl group, a cyclic group etc. In addition to the possibility of the substituents being a cyclic group, a combination of substituents may form a cyclic group. If the oxyhydrocarbyl group comprises more than one C then those carbons need not necessarily be linked to each other. For example, at least two of the carbons may be linked via a suitable element or group. Thus, the oxyhydrocarbyl group may contain hetero atoms. Suitable hetero atoms will be apparent to those skilled in the art and include, for instance, sulphur and nitrogen.

In one embodiment of the present invention, the oxyhydrocarbyl group is a oxyhydrocarbon group.

Here the term "oxyhydrocarbon" means any one of an alkoxy group, an oxyalkenyl group, an oxyalkynyl group, which groups may be linear, branched or cyclic, or an oxyaryl group. The term oxyhydrocarbon also includes those groups but wherein they have been optionally substituted. If the oxyhydrocarbon is a branched structure having substituent(s) thereon, then the substitution may be on either the hydrocarbon backbone or on the branch; alternatively the substitutions may be on the hydrocarbon backbone and on the branch.

Typically, the oxyhydrocarbyl group is of the formula C$_{1-6}$O (such as a C$_{1-3}$O).

R$_1$-R$_9$

As discussed herein each of R$_1$, R$_2$, R$_3$, R$_4$, R$_5$, R$_6$, R$_7$, R$_8$ and R$_9$ are independently selected from (a) H, (b) R$_{13}$, —OC(R$_{13}$)$_3$, —OCH(R$_{13}$)$_2$, —OCH$_2$R$_{13}$, —C(R$_{13}$)$_3$, —CH(R$_{13}$)$_2$, or —CH$_2$R$_{13}$ wherein R$_{13}$ is a halogen; (c) —CN; (d) optionally substituted alkyl, (e) optionally substituted heteroalkyl; (f) optionally substituted aryl; (g) optionally substituted heteroaryl; (h) optionally substituted arylalkyl; (i) optionally substituted heteroarylalkyl; (j) hydroxy; (k) alkoxy; (l) aryloxy; (m) —SO$_2$-alkyl; and (n) —N(R$_{14}$)C(O)R$_{15}$,
wherein R$_{14}$ and R$_{15}$ are independently selected from H and hydrocarbyl,
wherein the optional substituents of (d) (e) (f) (h) and (i) are selected from the group consisting of: C$_{1-6}$ alkyl, halo, cyano, nitro, haloalkyl, hydroxy, C$_{1-6}$ alkoxy, carboxy, carboxyalkyl, carboxamide, mercapto, amino, alkylamino, dialkylamino, sulfonyl, sulfonamido, aryl and heteroaryl.

In one preferred aspect each of R$_1$, R$_2$, R$_3$, R$_4$, R$_5$, R$_6$, R$_7$, R$_8$ and R$_9$ are independently selected from
(a) H and
(b) R$_{13}$, —OC(R$_{13}$)$_3$, —OCH(R$_{13}$)$_2$, —OCH$_2$R$_{13}$, —C(R$_{13}$)$_3$, —CH(R$_{13}$)$_2$, or —CH$_2$R$_{13}$, wherein R$_{13}$ is a halogen.

In one preferred aspect R$_{13}$ is Cl or F.

In one preferred aspect (b) is F, Cl, —OCF$_3$, —OCHF$_2$, —OCH$_2$F, —CF$_3$, —CHF$_2$, or —CH$_2$F.

In one preferred aspect (b) is F, Cl or OCF$_3$.

In one preferred aspect each of R$_1$, R$_2$, R$_3$, R$_4$, R$_5$, R$_6$, R$_7$, R$_8$ and R$_9$ are independently selected from F, Cl, —OCF$_3$, —OCHF$_2$, —OCH$_2$F, —CF$_3$, —CHF$_2$, or —CH$_2$F.

In one preferred aspect each of R$_1$, R$_2$, R$_3$, R$_4$, R$_5$, R$_6$, R$_7$, R$_8$ and R$_9$ are independently selected from F, Cl or OCF$_3$.

R$_1$

In one preferred aspect R$_1$ is selected from (b) R$_{13}$, —OC(R$_{13}$)$_3$, —OCH(R$_{13}$)$^2$, —OCH$_2$R$_{13}$, —C(R$_{13}$)$_3$, —CH(R$_{13}$)$_2$, or —CH$_2$R$_{13}$ wherein R$_{13}$ is a halogen; (c) —CN; (d) optionally substituted alkyl, (e) optionally substituted heteroalkyl; (f) optionally substituted aryl; (g) optionally substituted heteroaryl; (h) optionally substituted arylalkyl; (i) optionally substituted heteroarylalkyl; (j) hydroxy; (k) alkoxy; (l) aryloxy; (m) —SO$_2$-alkyl; and (n) —N(R$_{14}$)C(O)R$_{15}$,
wherein R$_{14}$ and R$_{15}$ are independently selected from H and hydrocarbyl,
wherein the optional substituents of (d) (e) (f) (h) and (i) are selected from the group consisting of: C$_{1-6}$ alkyl, halo, cyano, nitro, haloalkyl, hydroxy, C$_{1-6}$ alkoxy, carboxy, carboxyalkyl, carboxamide, mercapto, amino, alkylamino, dialkylamino, sulfonyl, sulfonamido, aryl and heteroaryl.

In one preferred aspect R$_1$ is H.

In a highly preferred aspect R$_1$ is H or Cl.

R$_2$

R$_2$ is selected from (a) H, (b) R$_{13}$, —OC(R$_{13}$)$_3$, —OCH(R$_{13}$)$_2$, —OCH$_2$R$_{13}$, —C(R$_{13}$)$_3$, —CH(R$_{13}$)$_2$, or —CH$_2$R$_{13}$ wherein R$_{13}$ is a halogen; (c) —CN; (d) optionally substituted alkyl, (e) optionally substituted heteroalkyl; (f) optionally substituted aryl; (g) optionally substituted heteroaryl; (h) optionally substituted arylalkyl; (i) optionally substituted heteroarylalkyl; (j) hydroxy; (k) alkoxy; (l) aryloxy; (m) —SO$_2$-alkyl; and (n) —N(R$_{14}$)C(O)R$_{15}$,
wherein R$_{14}$ and R$_{15}$ are independently selected from H and hydrocarbyl,
wherein the optional substituents of (d) (e) (f) (h) and (i) are selected from the group consisting of: C$_{1-6}$ alkyl, halo, cyano, nitro, haloalkyl, hydroxy, C$_{1-6}$ alkoxy, carboxy, carboxyalkyl, carboxamide, mercapto, amino, alkylamino, dialkylamino, sulfonyl, sulfonamido, aryl and heteroaryl;

In a preferred aspect R$_2$ is H

R$_3$

In one a preferred aspect R$_3$ is selected from R$_{13}$, —OC(R$_{13}$)$_3$, —OCH(R$_{13}$)$_2$, —OCH$_2$R$_{13}$, —C(R$_{13}$)$_3$, —CH(R$_{13}$)$_2$, or —CH$_2$R$_{13}$ wherein R$_{13}$ is a halogen.

In one a preferred aspect R$_3$ is selected from R$_{13}$ and —OC(R$_{13}$)$_3$ wherein R$_{13}$ is a halogen.

In a highly preferred aspect R$_3$ is Cl or OCF$_3$.

R$_4$-R$_7$

In one preferred aspect R$_4$ is H.
In one preferred aspect R$_5$ is H.
In one preferred aspect R$_6$ is H.
In one preferred aspect R$_7$ is H.
In one preferred highly preferred aspect each of R$_4$, R$_5$, R$_6$ and R$_7$ is H.

R$_8$

In one preferred aspect R$_3$ is selected from (a) H, (b) R$_{13}$, —OC(R$_{13}$)$_3$, —OCH(R$_{13}$)$_2$, —OCH$_2$R$_{13}$, C(R$_{13}$)$_3$, —CH(R$_{13}$)$_2$, or —CH$_2$R$_{13}$ wherein R$_{13}$ is a halogen;
In one preferred highly preferred aspect R$_3$ is H or F.
In one preferred highly preferred aspect R$_3$ is H.
In one preferred highly preferred aspect R$_3$ is F.

In one preferred highly preferred aspect $R_1$ is H or $C_1$, $R_3$ is Cl or $OCF_3$, $R_8$ is H or F, and $R_2$, $R_4$, $R_5$, $R_6$ and $R_7$ are each H.

X

As discussed herein X is an optional group selected from O, S, S=O, $S(=O)_2$, C=O, $S(=O)_2NR_{16}$, C=$ONR_{17}$, $NR_{18}$, in which $R_{16}$, $R_{17}$, and $R_{18}$ are independently selected from H and hydrocarbyl.

It will be understood by one skilled in the art that by the term "optional group" it is meant that X may represent a bond.

It will be understood by one skilled in the art that groups $S(=O)_2NR_{16}$ and C=$ONR_{17}$ may run either way between the rings $(R_1-R_6)Ph-(CH_2)n-(=O)_2-NR_{16}-(CH_2)_p-Ph(R_6-R_9)$
$(R_1-R_5)Ph-(CH_2)n-NR_{16}-S(=O)_2-(CH_2)_p-Ph(R_6-R_9)$
$(R_1-R_6)Ph-(CH_2)n-C(=O)-NR_{17}-(CH_2)_p-Ph(R_6-R_9)$ or
$(R_1-R_6)Ph-(CH_2)n-NR_{17}-C(=O)-(CH_2)_p-Ph(R_6-R_9)$ In one aspect X is present and accordingly X is a group selected from O, S, S=O, $S(=O)_2$, C=O, $S(=O)_2NR_{16}$, C=$ONR_{17}$, $NR_{18}$, in which $R_{16}$, $R_{17}$, and $R_{18}$ are independently selected from H and hydrocarbyl.

In one highly preferred aspect X is O.

In one highly preferred aspect X is O, n is 0 and p is 0.

$R_{16}$, $R_{17}$ and $R_{18}$

As discussed herein $R_{16}$, $R_{17}$ and $R_{18}$ are independently selected from H and hydrocarbyl.

In one preferred aspect $R_{16}$, $R_{17}$ and $R_{18}$ are independently selected from H, alkyl and acyl groups.

In one preferred aspect $R_{16}$, $R_{17}$ and $R_{18}$ are independently selected from H, $C_1$-$C_{10}$ alkyl (such as $C_1$-$C_6$ alkyl group, and $C_1$-$C_3$ alkyl group, including $C_1$ alkyl, $C_2$ alkyl, $C_3$ alkyl, $C_4$ alkyl, $C_5$ alkyl, $C_7$ alkyl, and $C_8$ alkyl), and $C_1$-$C_{10}$ acyl (such as $C_1$-$C_6$ acyl group, and $C_1$-$C_3$ acyl group, including $C_1$ acyl, $C_2$ acyl, $C_3$ acyl, $C_4$ acyl, $C_5$ acyl, $C_7$ acyl, and $C_8$ acyl).

In one preferred aspect $R_{16}$, $R_{17}$ and $R_{18}$ are independently selected from H and Me.

n and p n and p being 1 provide for methylene links between X and the phenyl rings.

Preferably n and/or p is 0.

Thus in one preferred aspect n is 0. In one preferred aspect p is 0. In one preferred aspect n is 0 and p is 0

$R_{10}$

In one preferred aspect $R_{10}$ is selected from H, alkyl and acyl groups.

In one preferred aspect $R_{10}$ is selected from H, —C(=O)$C_1$-$C_{10}$ alkyl (such as —C(=O)$C_1$-$C_6$ alkyl group, and —C(=O)$C_1$-$C_3$ alkyl group, including —C(=O)$C_1$ alkyl, —C(=O)$C_2$ alkyl, —C(=O)$C_3$ alkyl, —C(=O)$C_4$ alkyl, —C(=O)$C_5$ alkyl, —C(=O)$C_7$ alkyl, and —C(=O)$C_8$ alkyl), and $C_1$-$C_{10}$ alkyl (such as $C_1$-$C_6$ alkyl group, and $C_1$-$C_3$ alkyl group, including $C_1$ alkyl, $C_2$ alkyl, $C_3$ alkyl, $C_4$ alkyl, $C_5$ alkyl, $C_7$ alkyl, and $C_8$ alkyl).

In one preferred aspect $R_{10}$ is selected from H and $C_1$-$C_{10}$ alkyl (such as $C_1$-$C_6$ alkyl group, and $C_1$-$C_3$ alkyl group, including $C_1$ alkyl, $C_2$ alkyl, $C_3$ alkyl, $C_4$ alkyl, $C_5$ alkyl, $C_7$ alkyl, and $C_8$ alkyl).

Preferably $R_{10}$ is selected from H, —C(=O)$C_1$-$C_6$ alkyl and $C_{1-6}$ alkyl Preferably $R_{10}$ is selected from H and $C_{1-6}$ alkyl Preferably $R_{10}$ is selected from H and Me In one preferred aspect $R_{10}$ is selected from H, methyl (—$CH_3$) and acetyl (—CO—$CH_3$) groups.

Preferably $R_{10}$ is selected from H and Me. Preferably $R_{10}$ is H.

As discussed herein the compounds of the present may in the form of a salt. $NR_{10}$ may be in the form of a salt, for example a chloride salt.

$R_{11}$

As discussed herein $R_{11}$ is selected from $CR_{19}R_{20}$ and C=O, in which $R_{19}$ and $R_{20}$ are independently selected from H and hydrocarbyl, In one preferred aspect $R_{11}$ is $CR_{19}R_{20}$, in which $R_{19}$ and $R_{20}$ are independently selected from H and hydrocarbyl. In one preferred aspect at least one of $R_{19}$ and $R_{20}$ is a hydrocarbyl.

In one preferred aspect $R_{11}$ is C=O.

Preferably $R_{19}$ and $R_{20}$ are independently selected from H, alkyl, alkenyl and alkylaryl groups In one preferred aspect at least one of $R_{19}$ and $R_{20}$ is independently selected from alkyl, alkenyl and alkylaryl groups.

Preferably $R_{19}$ and $R_{20}$ are independently selected from H, $C_{1-6}$ alkyl, $C_{1-6}$ alkenyl and $C_{1-6}$ alkyl phenyl groups. In one preferred aspect at least one of $R_{19}$ and $R_{20}$ is independently selected from $C_{1-6}$ alkyl, $C_{1-6}$ alkenyl and $C_{1-6}$ alkyl phenyl groups.

Preferably $R_{19}$ and $R_{20}$ are independently selected from H, —$CH_3$, —$CH_2CH_3$, —$CH_2CH_2CH_3$, —$CH_2CH=CH_2$, and —$CH_2$-Ph. In one preferred aspect at least one of $R_{19}$ and $R_{20}$ is selected from —$CH_3$, —$CH_2CH_3$, —$CH_2CH_2CH_3$, —$CH_2CH=CH_2$, and —$CH_2$-Ph. Preferably $R_{19}$ and $R_{20}$ are independently selected from H, —$CH_3$, —$CH_2CH_2CH_3$, —$CH_2CH=CH_2$, and —$CH_2$-Ph. In one preferred aspect at least one of $R_{19}$ and $R_{20}$ is selected from —$CH_3$, —$CH_2CH_2CH_3$, —$CH_2CH=CH_2$, and —$CH_2$-Ph In one preferred aspect $R_{20}$ is H and $R_{19}$ is selected from H, —$CH_3$, —$CH_2CH_3$, —$CH_2CH_2CH_3$, —$CH_2CH=CH_2$, and —$CH_2$-Ph. In one preferred aspect at least one of $R_{19}$ and $R_{20}$ is selected from —$CH_3$, —$CH_2CH_3$, —$CH_2CH_2CH_3$, —$CH_2CH=CH_2$, and —$CH_2$-Ph. In one preferred aspect $R_{20}$ is H and $R_{19}$ is selected from H, —$CH_3$, —$CH_2CH_2CH_3$, —$CH_2CH=CH_2$, and —$CH_2$-Ph. In one preferred aspect at least one of $R_{19}$ and $R_{20}$ is selected from —$CH_3$, —$CH_2CH_2CH_3$, —$CH_2CH=CH_2$, and —$CH_2$-Ph.

In one highly preferred aspect $R_{20}$ is H and $R_{19}$ is selected from —$CH_3$, —$CH_2CH_3$, —$CH_2CH_2CH_3$, —$CH_2CH=CH_2$, and —$CH_2$-Ph. In one highly preferred aspect $R_{20}$ is H and $R_{19}$ is selected from —$CH_3$, —$CH_2CH_2CH_3$, —$CH_2CH=CH_2$, and —$CH_2$-Ph.

In one highly preferred aspect $R_{20}$ is H and $R_{19}$ is selected from —$CH_3$, and —$CH_2CH_3$.

In one highly preferred aspect $R_{20}$ is H and $R_{19}$ is —$CH_3$.

In one highly preferred aspect $R_{20}$ is H and $R_{19}$ is —$CH_2CH_3$.

$R_{12}$

As discussed herein $R_{12}$ is selected from five or six membered carbon rings optionally containing one or more hetero atoms selected from N, S, and O and optionally having fused thereto a further ring. It will be understood that by "five or six membered carbon rings optionally containing one or more hetero atoms selected from N, S, and O" it is meant a ring containing carbon and optionally N, S, and O and wherein the total number of members (both carbon and optional N, S, and O) is five or six.

In one preferred aspect $R_{12}$ is a substituted aryl ring, optionally having fused thereto a further ring, and wherein the one or more substituents are selected from hydrocarbyl groups.

In one preferred aspect $R_{12}$ is a substituted carbocyclic ring, optionally having fused thereto a further ring, and wherein the one or more substituents are selected from hydrocarbyl groups.

In one preferred aspect $R_{12}$ is a substituted six membered carbocyclic ring, optionally having fused thereto a further ring, and wherein the one or more substituents are selected from hydrocarbyl groups.

In one preferred aspect $R_{12}$ is a substituted phenyl ring, optionally having fused thereto a further ring, and wherein the one or more substituents are selected from hydrocarbyl groups.

In one preferred aspect $R_{12}$ is a substituted heterocyclic ring, optionally having fused thereto a further ring, and wherein the one or more substituents are selected from hydrocarbyl groups.

In one preferred aspect the heterocyclic ring contain carbon and nitrogen.

In one preferred aspect the heterocyclic ring contains carbon and only one nitrogen.

In one preferred aspect $R_{12}$ is a substituted pyrrole ring, optionally having fused thereto a further ring, and wherein the one or more substituents are selected from hydrocarbyl groups.

In one preferred aspect $R_{12}$ is an optionally substituted pyrrolidone, and wherein the one or more substituents are selected from hydrocarbyl groups. Preferably the pyrrolidone is a 2-pyrrolidone. Preferably the pyrrolidone is unsubstituted. Preferably the pyrrolidone is unsubstituted 2-pyrrolidone.

Preferably the optional further ring fused to the ring of $R_{12}$ is independently selected from five or six membered carbon rings optionally containing one or more hetero atoms selected from N, S, and O. Preferably the optional further ring fused to the ring of $R_{12}$ is a five membered carbon rings containing one or more oxygen atoms.

In one preferred aspect $R_{12}$ is a substituted group of the formula:

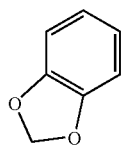

In one preferred aspect $R_{12}$ is a substituted group of the formula:

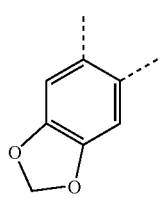

wherein - - - - are points of attachment to $R_{11}$ and of the substituent.

In one preferred aspect $R_{12}$ is a substituted group of the formula:

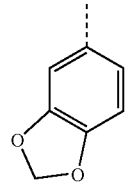

wherein - - - - is the point of attachment to $R_{11}$.

In one preferred aspect $R_{12}$ is a substituted group of the formula:

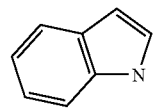

In one preferred aspect $R_{12}$ is a substituted group of the formula:

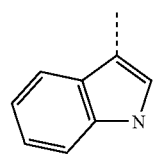

wherein - - - - is the point of attachment to $R_{11}$.

In one preferred aspect $R_{12}$ is a substituted group of the formula:

In one preferred aspect $R_{12}$ is a substituted group of the formula:

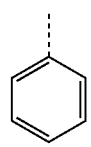

wherein - - - - is the point of attachment to $R_{11}$.

In one preferred aspect $R_{12}$ is a substituted group of the formula:

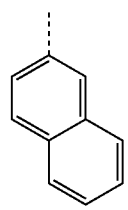

wherein - - - - is the point of attachment to $R_{11}$.

In one preferred aspect $R_{12}$ is selected from substituted group of the formulae:

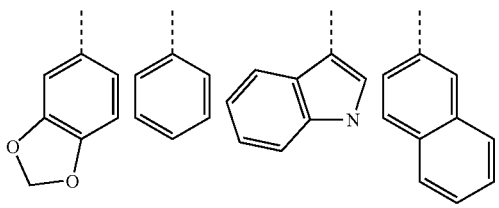

wherein - - - - is the point of attachment to $R_{11}$.

In one preferred aspect $R_{12}$ is selected from substituted group of the formulae:

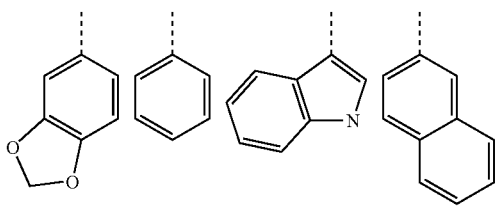

wherein - - - - is the point of attachment to $R_{11}$ and wherein the one or more substituents are selected from amide groups, alkyl groups, alkoxy groups and halogens,
preferably the one or more substituents are selected from —$NR_{21}$—CO—$R_{22}$, $C_{1-10}$ alkyl groups, $C_{1-10}$ alkoxy groups and halogens, wherein $R_{21}$ and $R_{22}$ are independently selected from H and hydrocarbyl and wherein $R_{21}$ and $R_{22}$ may join to form a pyrrolidone ring
preferably the one or more substituents are selected from —$NR_{21}$—CO—$R_{22}$, $C_{1-10}$ alkyl groups, $C_{1-10}$ alkoxy groups and halogens, wherein $R_{21}$ and $R_{22}$ are independently selected from H and hydrocarbyl,
preferably the one or more substituents are selected from —$NR_{21}$—CO—$R_{22}$, $C_{1-3}$ alkyl groups, $C_{1-3}$ alkoxy groups and halogens, wherein $R_{21}$ and $R_{22}$ are independently selected from H and hydrocarbyl and wherein $R_{21}$ and $R_{22}$ may join to form a pyrrolidone ring,
preferably the one or more substituents are selected from —$NR_{21}$—CO—$R_{22}$, $C_{1-3}$ alkyl groups, $C_{1-3}$ alkoxy groups and halogens, wherein $R_{21}$ and $R_{22}$ are independently selected from H and hydrocarbyl,
  preferably $R_{21}$ and $R_{22}$ are independently selected from H, phenyl and $C_{1-10}$ alkyl groups wherein $R_{21}$ and $R_{22}$ may join to form a pyrrolidone ring, or
  preferably $R_{21}$ and $R_{22}$ are independently selected from H, phenyl and $C_{1-10}$ alkyl groups, or
  preferably $R_{21}$ and $R_{22}$ are independently selected from H, methyl and phenyl.
preferably the one or more substituents are selected from —NEt-CO-Me, 2-pyrrolidone, —NMe-CO-Me, —NH—CO-Me, —NH—CO-Ph, —NMe-CO-Me, —OMe, -Me, and —Cl
preferably the one or more substituents are selected from —NEt-CO-Me, —NMe-CO-Me, —NH—CO-Me, —NH—CO-Ph, —NMe-CO-Me, —OMe, -Me, and —Cl
preferably the one or more substituents are selected from —NH—CO-Me, —NH—CO-Ph, —NMe-CO-Me, —OMe, -Me, and —Cl Preferably the ring of $R_{12}$ has fused thereto a further ring, the fused rings together contain six or more members, preferably from six to ten members.

In one aspect the ring of $R_{12}$ is selected from phenyl, furan, pyrimidine, pyridine, and thiophene. In one aspect the ring of $R_{12}$ is selected from phenyl, pyrimidine, pyridine, and thiophene. Preferably the ring of $R_{12}$ is phenyl.

In a preferred aspect $R_{12}$ is selected from a substituted five or six membered carbon rings, wherein the one or more substituents are selected from amide groups, alkyl groups, alkoxy groups and halogens.

In a preferred aspect the one or more substituents are selected from —$NR_{21}$—CO—$R_{22}$, $C_{1-10}$ alkyl groups, $C_{1-10}$ alkoxy groups and halogens, wherein $R_{21}$ and $R_{22}$ are independently selected from: H and hydrocarbyl and wherein $R_{21}$ and $R_{22}$ may join to form a pyrrolidone ring. In a preferred aspect the one or more substituents are selected from —$NR_{21}$—CO—$R_{22}$, $C_{1-10}$ alkyl groups, $C_{1-10}$ alkoxy groups and halogens, wherein $R_{21}$ and $R_{22}$ are independently selected from H and hydrocarbyl.

In a preferred aspect the one or more substituents are selected from —$NR_{21}$—CO—$R_{22}$, $C_{1-3}$ alkyl groups, $C_{1-3}$ alkoxy groups and halogens, wherein $R_{21}$ and $R_{22}$ are independently selected from H and hydrocarbyl and wherein $R_{21}$ and $R_{22}$ may join to form a pyrrolidone ring. In a preferred aspect the one or more substituents are selected from —$NR_{21}$—CO—$R_{22}$, $C_{1-3}$ alkyl groups, $C_{1-3}$ alkoxy groups and halogens, wherein $R_{21}$ and $R_{22}$ are independently selected from H and hydrocarbyl.

Preferably $R_{21}$ and $R_{22}$ are independently selected from H, phenyl and $C_{1-10}$ alkyl groups wherein $R_{21}$ and $R_{22}$ may join to form a pyrrolidone ring. Preferably $R_{21}$ and $R_{22}$ are independently selected from H, phenyl and $C_{1-10}$ alkyl groups.

Preferably $R_{21}$ and $R_{22}$ are independently selected from H, methyl and phenyl.

Preferably the one or more substituents are selected from —NEt-CO-Me, 2-pyrrolidone, —NMe-CO-Me, —NH—CO-Me, —NH—CO-Ph, —NMe-CO-Me, —OMe, -Me, and —Cl. Preferably the one or more substituents are selected from —NEt-CO-Me, —NMe-CO-Me, —NH—CO-Me, —NH—CO-Ph, —NMe-CO-Me, —OMe, -Me, and —Cl. Preferably the one or more substituents are selected from —NH—CO-Me, —NH—CO-Ph, —NMe-CO-Me, —OMe, -Me, and —Cl In a preferred aspect the compound of the present invention is a compound having Formula II

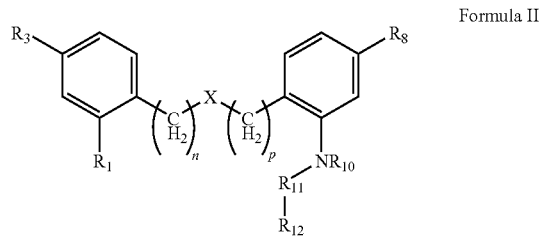

Formula II

In a preferred aspect the compound of the present invention is a compound having Formula III

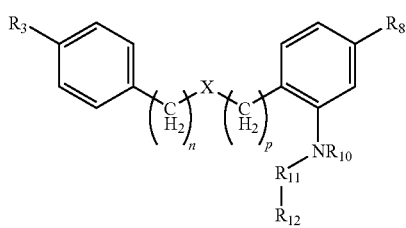

Formula III

In a preferred aspect the compound of the present invention is a compound having Formula IV

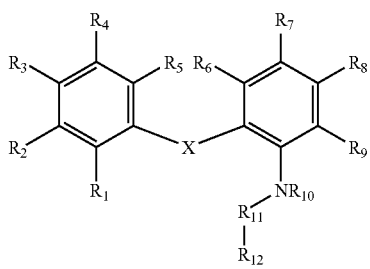

Formula IV

In a preferred aspect the compound of the present invention is a compound having Formula V

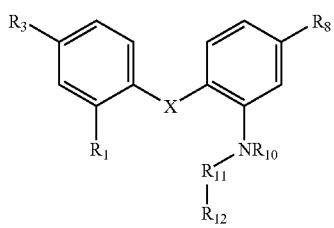

Formula V

In a preferred aspect the compound of the present invention is a compound having Formula VI

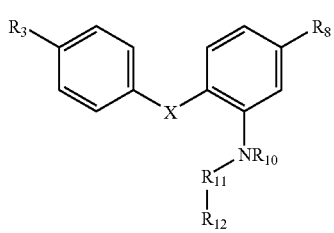

Formula VI

In a preferred aspect the compound of the present invention is a compound having Formula VII

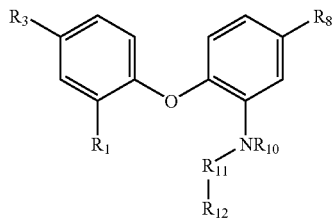

Formula VII

In a preferred aspect the compound of the present invention is a compound having Formula VIII

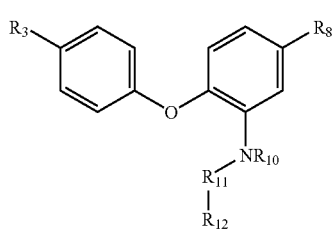

Formula VIII

In a preferred aspect the compound of the present invention is a compound having Formula VIII

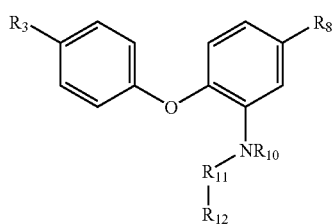

Formula VIII wherein $R_{12}$ is selected from substituted group of the formulae:

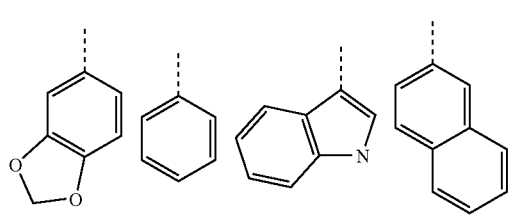

wherein - - - - is the point of attachment to $R_{11}$.

In a preferred aspect the compound of the present invention is a compound having Formula VIIIa

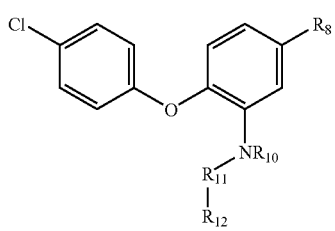

Formula VIIIa wherein $R_{12}$ is selected from substituted group of the formulae:

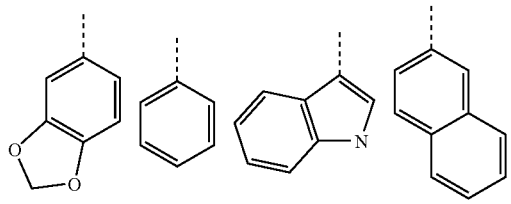

wherein - - - - is the point of attachment to $R_{11}$.

In a preferred aspect the compound of the present invention is a compound having Formula VIIIb

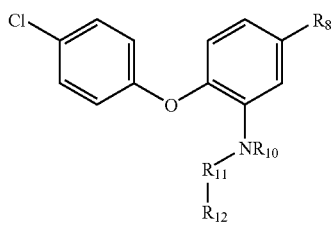

Formula VIIIb wherein $R_8$ is selected from F and H (preferably H)
wherein $R_{12}$ is selected from substituted group of the formulae:

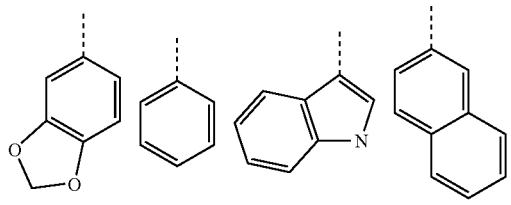

wherein - - - - is the point of attachment to $R_{11}$.

In a preferred aspect the compound of the present invention is a compound having Formula VIIIb

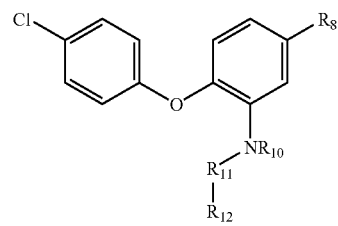

Formula VIIIb wherein $R_8$ is selected from F and H (preferably H)

wherein $R_{10}$ is selected from H, C=O—$C_{1-6}$ alkyl and $C_{1-6}$ alkyl (preferably C=OMe, Me and H)

wherein $R_{11}$ is selected from C=O and $CR_{19}R_{20}$, in which $R_{20}$ is H and $R_{19}$ is selected from —$CH_3$, —$CH_2CH_3$, —$CH_2CH_2CH_3$, —$CH_2CH=CH_2$, and —$CH_2$-Ph.

wherein $R_{12}$ is selected from substituted group of the formulae:

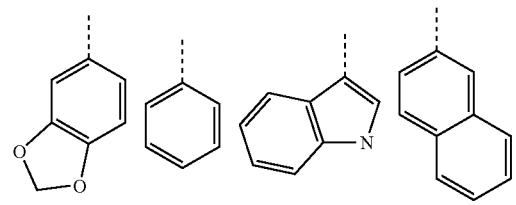

wherein - - - - is the point of attachment to $R_{11}$ and the one or more substituents are selected from —NEt-CO-Me, 2-pyrrolidone, —NMe-CO-Me, —NH—CO-Me, —NH—CO-Ph, —NMe-CO-Me, —OMe, -Me, and —Cl. Preferably the one or more substituents are selected from —NEt-CO-Me, —NMe-CO-Me, —NH—CO-Me, —NH—CO-Ph, —NMe-CO-Me, —OMe, -Me, and —Cl.

In a highly preferred aspect the compound is selected from the following compounds

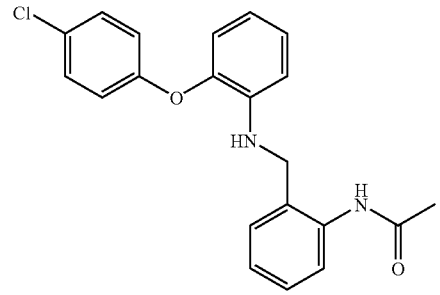

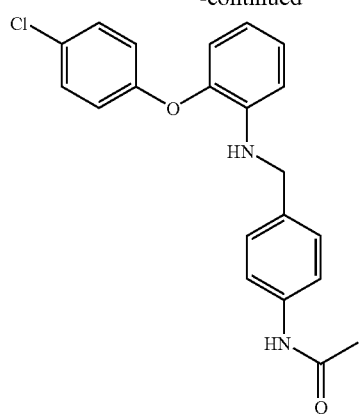
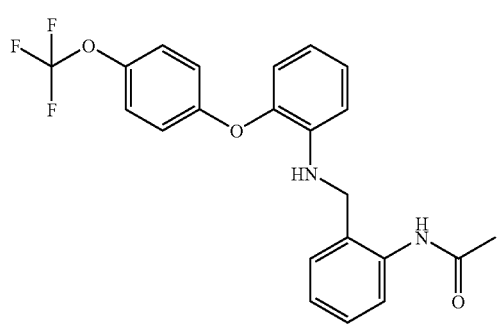
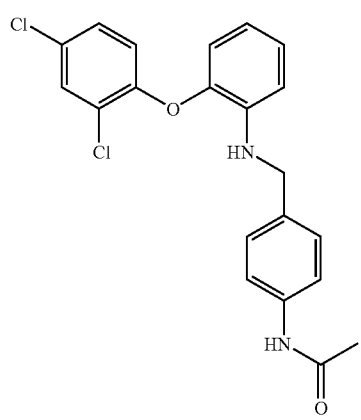
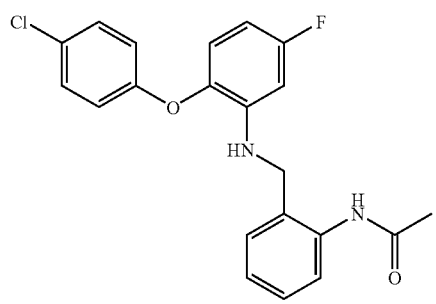
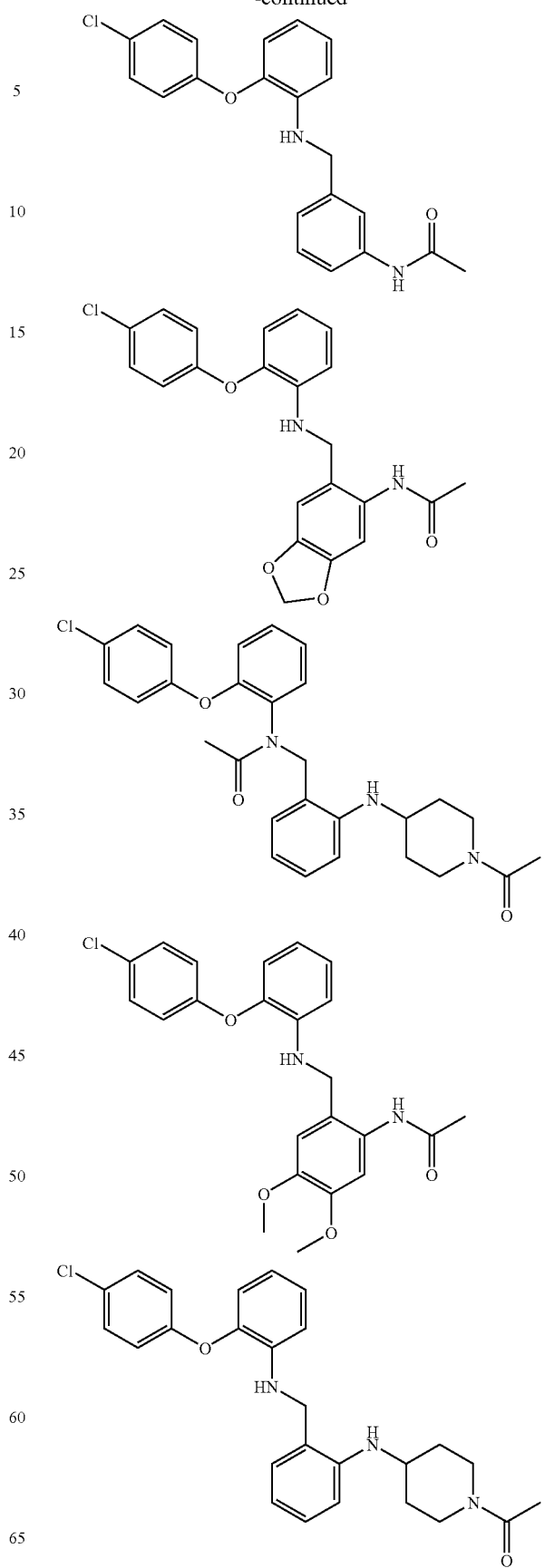

-continued
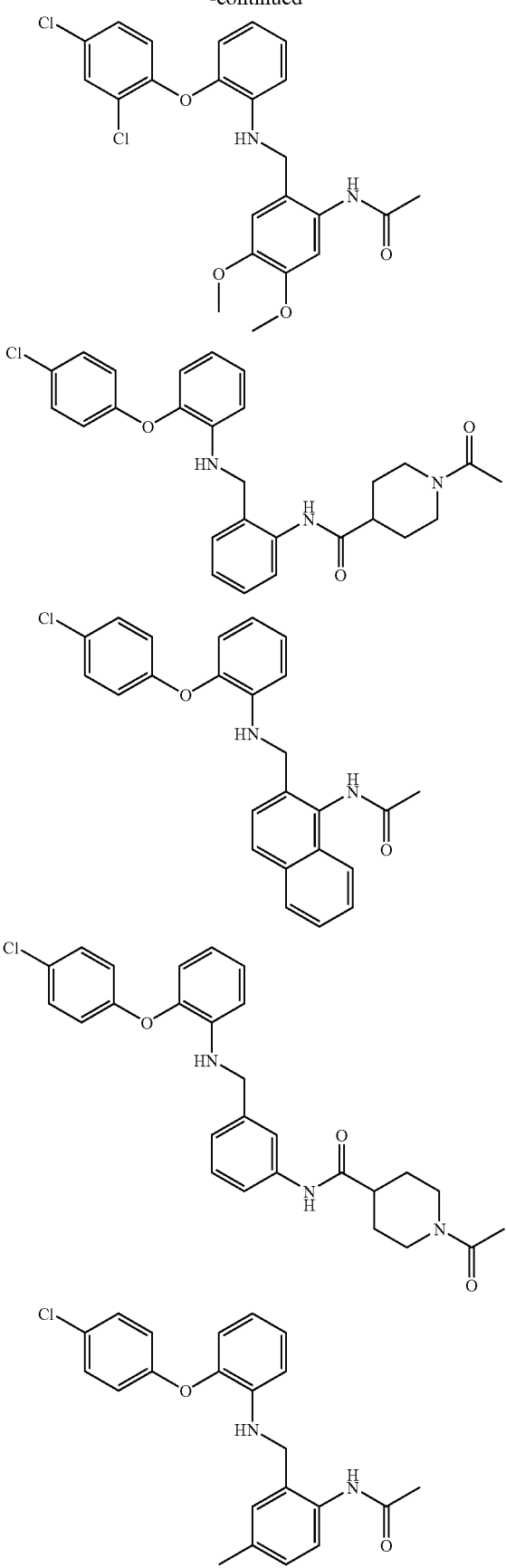
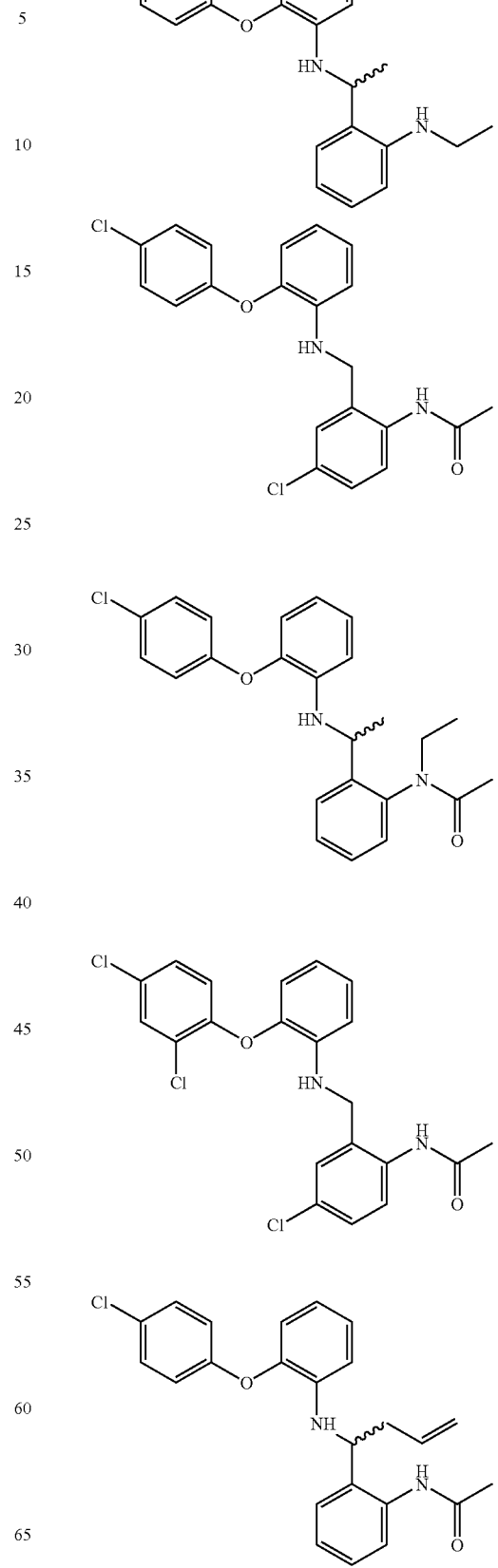

-continued
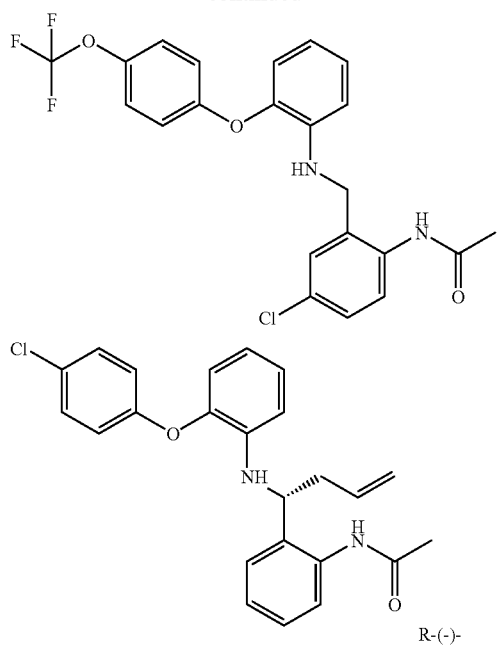
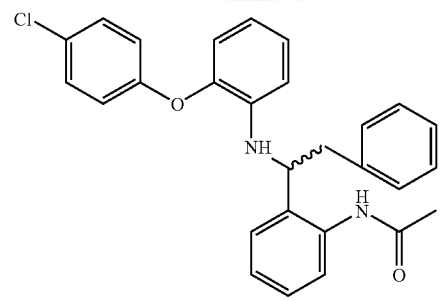
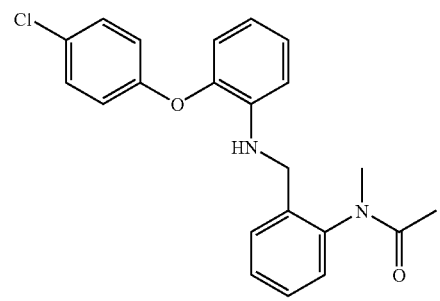
R-(-)-
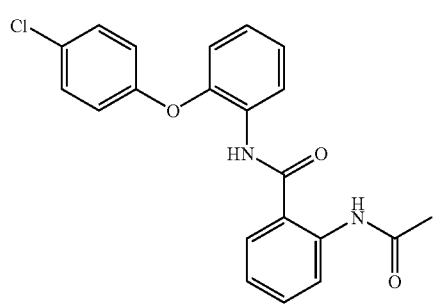
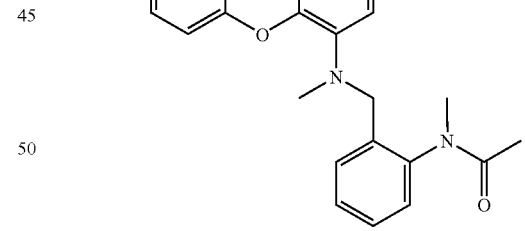
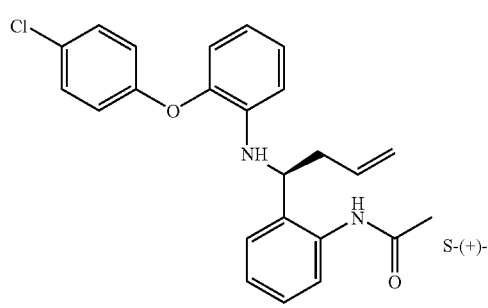
S-(+)-
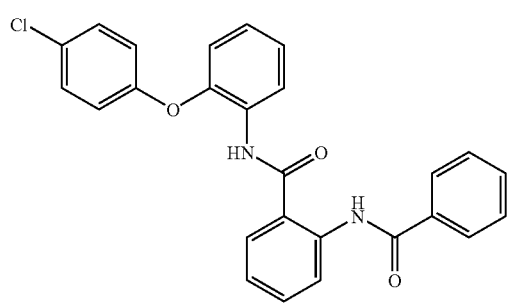
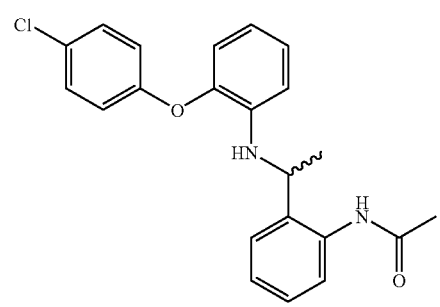

27
-continued
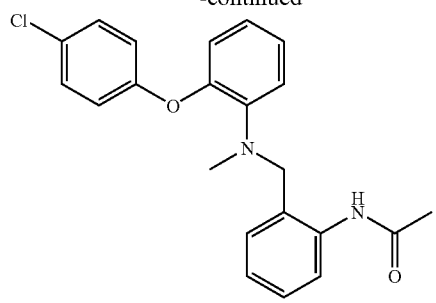
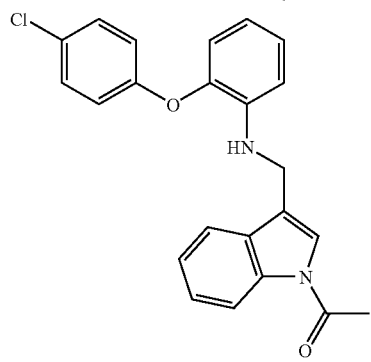
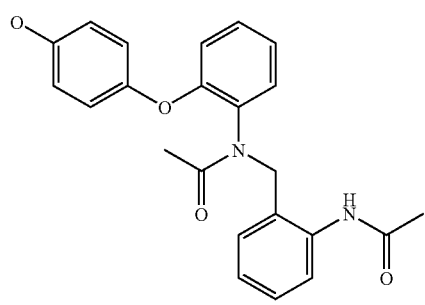
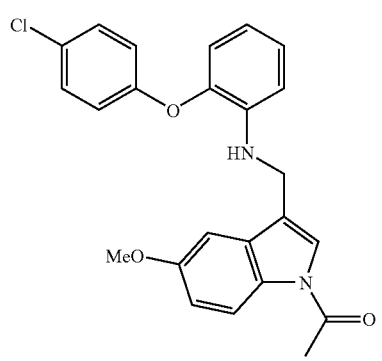
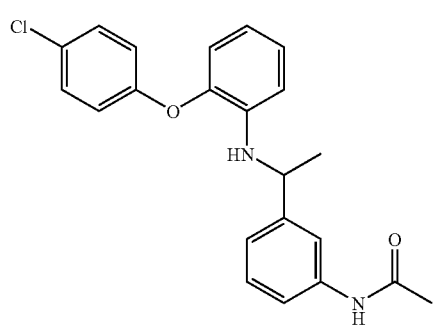
28
-continued
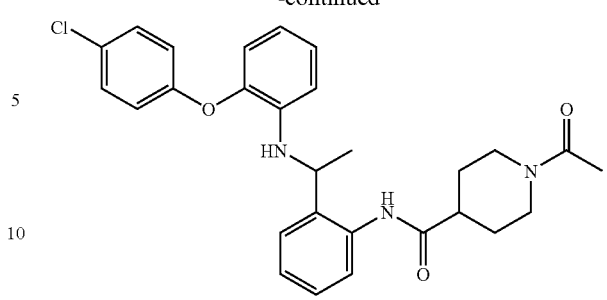
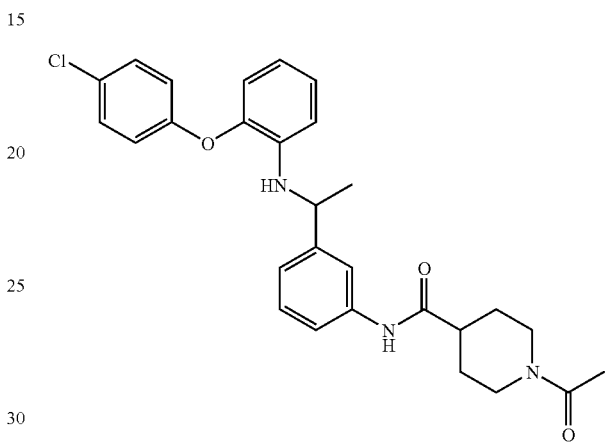
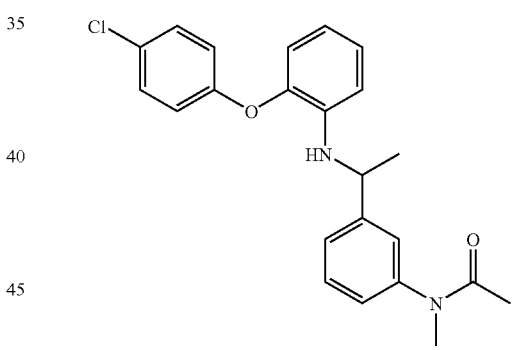
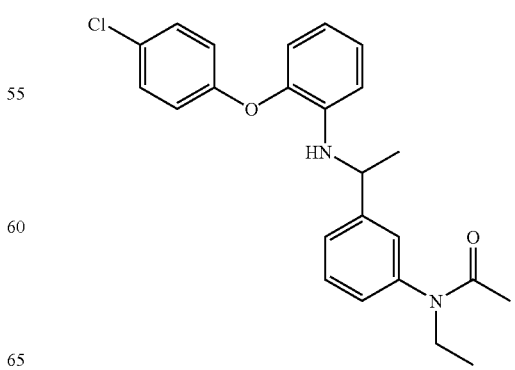

-continued

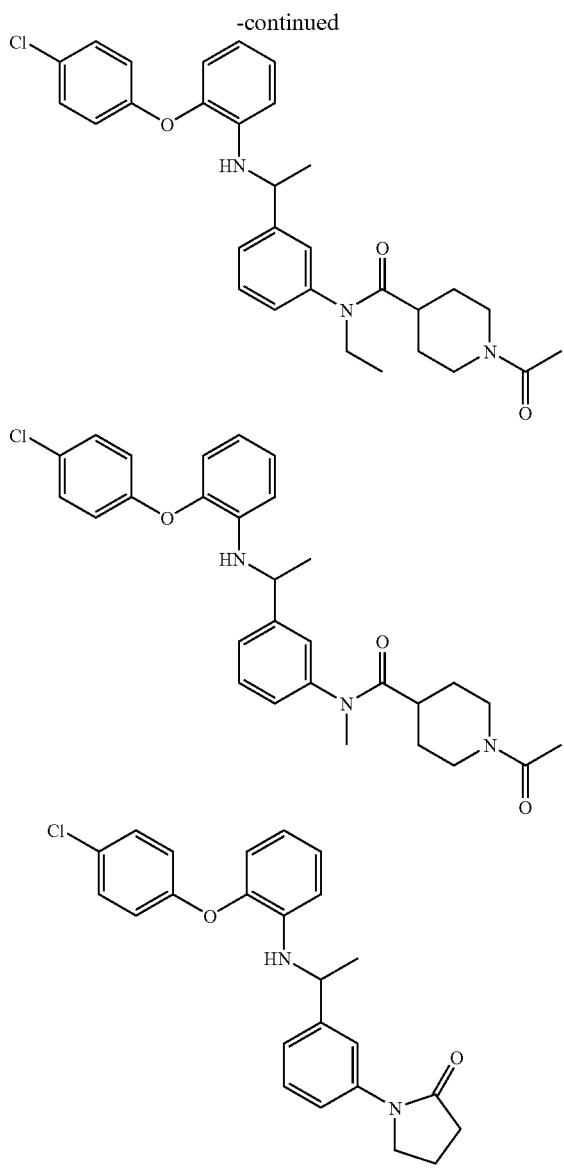

For some applications, preferably the compounds have a reversible action.

For some applications, preferably the compounds have an irreversible action.

The compounds of the present invention may be in the form of a salt.

The present invention also covers novel intermediates that are useful to prepare the compounds of the present invention. For example, the present invention covers novel alcohol precursors for the compounds. The present invention also encompasses a process comprising precursors for the synthesis of the compounds of the present invention.

The compound of the present invention may have substituents other than those of the ring systems show herein. Furthermore the ring systems herein are given as general formulae and should be interpreted as such. The absence of any specifically shown substituents on a given ring member indicates that the ring member may substituted with any moiety of which H is only one example. Each ring system may contain one or more degrees of unsaturation, for example is some aspects one or more rings of a ring system is aromatic. Each ring system may be carbocyclic or may contain one or more hetero atoms.

The compound of the invention, in particular the ring systems of the compound of the invention may contain substituents other than those show herein. By way of example, these other substituents may be one or more of: one or more halo groups, one or more O groups, one or more hydroxy groups, one or more amino groups, one or more sulphur containing group(s), one or more hydrocarbyl group(s)—such as an oxyhydrocarbyl group.

In general terms the ring systems of the present compounds may contain a variety of non-interfering substituents. In particular, the ring systems may contain one or more hydroxy, alkyl especially lower ($C_1$-$C_6$) alkyl, e.g. methyl, ethyl, n-propyl, isopropyl, n-butyl, sec-butyl, tert-butyl, n-pentyl and other pentyl isomers, and n-hexyl and other hexyl isomers, alkoxy especially lower ($C_1$-$C_6$) alkoxy, e.g. methoxy, ethoxy, propoxy etc., alkinyl, e.g. ethinyl, or halogen, e.g. fluoro substituents.

Hydroxysteroid Dehydrogenase

17β Hydroxysteroid dehydrogenase may be referred to as "17β-HSD" for short.

In some aspects of the invention 17β-HSD is preferably 17β-HSD Type 3.

Hydroxysteroid Dehydrogenase Inhibition

It is believed that some disease conditions associated with 17β-HSD activity are due to conversion of 4-androstene-3,17-one (A) to testosterone (T). In disease conditions associated with 17β-HSD activity, it would be desirable to inhibit 17β-HSD activity and in particular 17β-HSD3 activity.

Here, the term "inhibit" includes reduce and/or eliminate and/or mask and/or prevent the detrimental action of 17β-HSD.

HSD Inhibitor

In accordance with the present invention, the compound of the present invention is capable of acting as an 17β-HSD inhibitor.

Here, the term "inhibitor" as used herein with respect to the compound of the present invention means a compound that can inhibit 17β-HSD activity—such as reduce and/or eliminate and/or mask and/or prevent the detrimental action of 17β-HSD. The 17β-HSD inhibitor may act as an antagonist.

The ability of compounds to inhibit 17β hydroxysteroid dehydrogenase activity can be assessed using the suitable biological assay presented in the Examples section.

It is to be noted that the compound of the present invention may have other beneficial properties in addition to or in the alternative to its ability to inhibit HSD activity.

Therapy

In one aspect the present invention provides use of a compound as described herein in the manufacture of a medicament for use in the therapy of an androgen dependent disease or estrogen dependent disease.

Types of androgen or estrogen dependent diseases include, but are not limited to prostate cancer, benign prostatic hyperplasia, prostatic intraepithelial neoplasia, acne, seborrheas, hirsutism, androgenic alopecia, precocious puberty, adrenal hyperplasia, and polycystic ovarian syndrome, breast cancer, endometriosis and leiomyoma.

In one aspect the present invention provides use of a compound as described herein in the manufacture of a medicament for use in the therapy of a condition or disease selected from the group consisting of prostate cancer, androgen dependent neoplasms, benign prostatic hyperplasia, prostatic intraepithelial neoplasia, androgenic alopecia (i.e. pattern baldness in both male and female patients), hirsutism, polycystic ovary syndrome and acne.

In one aspect the present invention provides use of a compound as described herein in the manufacture of a medicament for use in the therapy of a condition or disease associated with 17β-HSD.

In one aspect the present invention provides use of a compound as described herein in the manufacture of a medicament for use in the therapy of a condition or disease associated with adverse 17β-HSD levels.

In one aspect the present invention provides use of a compound as described herein in the manufacture of a pharmaceutical for modulating 17β-HSD activity.

In one aspect the present invention provides use of a compound as described herein in the manufacture of a pharmaceutical for inhibiting 17β-HSD activity.

Preferably the 17β-HSD is 17β-HSD Type 3.

The compounds of the present invention may be used as therapeutic agents—i.e. in therapy applications.

The term "therapy" includes curative effects, alleviation effects, and prophylactic effects.

The therapy may be on humans or animals, preferably male animals or humans, such as male humans.

Pharmaceutical Compositions

In one aspect, the present invention provides a pharmaceutical composition, which comprises a compound according to the present invention and optionally a pharmaceutically acceptable carrier, diluent or excipient (including combinations thereof).

The pharmaceutical compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Preservatives, stabilisers, dyes and even flavouring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition of the present invention may be formulated to be delivered using a minipump or by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation may be designed to be delivered by both routes.

Where the agent is to be delivered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

Combination Pharmaceutical

The compound of the present invention may be used in combination with one or more other active agents, such as one or more other pharmaceutically active agents.

By way of example, the compounds of the present invention may be used in combination with other 17β-HSD inhibitors and/or other inhibitors such as an aromatase inhibitor (such as for example, 4hydroxyandrostenedione (4-OHA)), and/or a steroid sulphatase inhibitors such as EMATE and/or steroids and/or Coumate 667—such as the naturally occurring sterneurosteroids dehydroepiandrosterone sulfate (DH-EAS) and pregnenolone sulfate (PS) and/or other structurally similar organic compounds.

In addition, or in the alternative, the compound of the present invention may be used in combination with a biological response modifier.

The term biological response modifier ("BRM") includes cytokines, immune modulators, growth factors, haematopoiesis regulating factors, colony stimulating factors, chemotactic, haemolytic and thrombolytic factors, cell surface receptors, ligands, leukocyte adhesion molecules, monoclonal antibodies, preventative and therapeutic vaccines, hormones, extracellular matrix components, fibronectin, etc. For some applications, preferably, the biological response modifier is a cytokine. Examples of cytokines include: interleukins (IL)—such as IL-1, IL-2, IL-3, IL-4, IL-5, IL-6, IL-7, IL-8, IL-9, IL-10, IL-11, IL-12, IL-19; Tumour Necrosis Factor (TNF)— such as TNF-α; Interferon alpha, beta and gamma; TGF-β. For some applications, preferably the cytokine is tumour necrosis factor (TNF). For some applications, the TNF may be any type of TNF—such as TNF-α, TNF-β, including derivatives or mixtures thereof. More preferably the cytokine is TNF-α. Teachings on TNF may be found in the art—such as WO-A-98/08870 and WO-A-98/13348.

In addition, or in the alternative, the compound of the present invention may be used in combination with an androgen receptor (AR) modulator.

Administration

Typically, a physician will determine the actual dosage which will be most suitable for an individual subject and it will vary with the age, weight and response of the particular patient. The dosages below are exemplary of the average case. There can, of course, be individual instances where higher or lower dosage ranges are merited.

The compositions of the present invention may be administered by direct injection. The composition may be formulated for parenteral, mucosal, intramuscular, intravenous, subcutaneous, intraocular or transdermal administration. Depending upon the need, the agent may be administered at a dose of from 0.01 to 30 mg/kg body weight, such as from 0.1 to 10 mg/kg, more preferably from 0.1 to 1 mg/kg body weight.

By way of further example, the agents of the present invention may be administered in accordance with a regimen of every second or third day, or 1 to 4 times per day, preferably once or twice per day. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Aside from the typical modes of delivery—indicated above—the term "administered" also includes delivery by techniques such as lipid mediated transfection, liposomes, immunoliposomes, lipofectin, cationic facial amphiphiles (CFAs) and combinations thereof. The routes for such delivery mechanisms include but are not limited to mucosal, nasal, oral, parenteral, gastrointestinal, topical, or sublingual routes.

The term "administered" includes but is not limited to delivery by a mucosal route, for example, as a nasal spray or aerosol for inhalation or as an ingestable solution; a parenteral route where delivery is by an injectable form, such as, for example, an intravenous, intramuscular or subcutaneous route.

Thus, for pharmaceutical administration, the compounds of the present invention can be formulated in any suitable manner utilising conventional pharmaceutical formulating techniques and pharmaceutical carriers, adjuvants, excipients, diluents etc. and usually for parenteral administration. Approximate effective dose rates may be in the range from 1 to 1000 mg/day, such as from 10 to 900 mg/day or even from 100 to 800 mg/day depending on the individual activities of the compounds in question and for a patient of average (70 Kg) bodyweight. More usual dosage rates for the preferred and more active compounds will be in the range 200 to 800 mg/day, more preferably, 200 to 500 mg/day, most preferably from 200 to 250 mg/day. They may be given in single dose regimes, split dose regimes and/or in multiple dose regimes lasting over several days. For oral administration they may be formulated in tablets, capsules, solution or suspension containing from 100 to 500 mg of compound per unit dose. Alternatively and preferably the compounds will be formulated for parenteral administration in a suitable parenterally administrable carrier and providing single daily dosage rates in the range 200 to 800 mg, preferably 200 to 500, more preferably 200 to 250 mg. Such effective daily doses will, however, vary depending on inherent activity of the active ingredient and on the bodyweight of the patient, such variations being within the skill and judgement of the physician.

Cell Cycling

The compounds of the present invention may be useful in the method of treatment of a cell cycling disorder.

As discussed in "Molecular Cell Biology" 3rd Ed. Lodish et al. pages 177-181 different eukaryotic cells can grow and divide at quite different rates. Yeast cells, for example, can divide every 120 min., and the first divisions of fertilised eggs in the embryonic cells of sea urchins and insects take only 1530 min. because one large pre-existing cell is subdivided. However, most growing plant and animal cells take 10-20 hours to double in number, and some duplicate at a much slower rate. Many cells in adults, such as nerve cells and striated muscle cells, do not divide at all; others, like the fibroblasts that assist in healing wounds, grow on demand but are otherwise quiescent.

Still, every eukaryotic cell that divides must be ready to donate equal genetic material to two daughter cells. DNA synthesis in eukaryotes does not occur throughout the cell division cycle but is restricted to a part of it before cell division.

The relationship between eukaryotic DNA synthesis and cell division has been thoroughly analysed in cultures of mammalian cells that were all capable of growth and division. In contrast to bacteria, it was found, eukaryotic cells spend only a part of their time in DNA synthesis, and it is completed hours before cell division (mitosis). Thus a gap of time occurs after DNA synthesis and before cell division; another gap was found to occur after division and before the next round of DNA synthesis. This analysis led to the conclusion that the eukaryotic cell cycle consists of an M (mitotic) phase, a $G_1$ phase (the first gap), the S (DNA synthesis) phase, a $G_2$ phase (the second gap), and back to M. The phases between mitoses ($G_1$, S, and $G_2$) are known collectively as the interphase.

Many nondividing cells in tissues (for example, all quiescent fibroblasts) suspend the cycle after mitosis and just prior to DNA synthesis; such "resting" cells are said to have exited from the cell cycle and to be in the $G_o$ state.

It is possible to identify cells when they are in one of the three interphase stages of the cell cycle, by using a fluorescence-activated cell sorter (FACS) to measure their relative DNA content: a cell that is in $G_1$ (before DNA synthesis) has a defined amount x of DNA; during S (DNA replication), it has between x and 2x; and when in $G_2$ (or M), it has 2x of DNA.

The stages of mitosis and cytokinesis in an animal cell are as follows (a) Interphase. The $G_2$ stage of interphase immediately precedes the beginning of mitosis. Chromosomal DNA has been replicated and bound to protein during the S phase, but chromosomes are not yet seen as distinct structures. The nucleolus is the only nuclear substructure that is visible under light microscope. In a diploid cell before DNA replication there are two morphologic chromosomes of each type, and the cell is said to be 2n. In $G_2$, after DNA replication, the cell is 4n. There are four copies of each chromosomal DNA. Since the sister chromosomes have not yet separated from each other, they are called sister chromatids.

b) Early prophase. Centrioles, each with a newly formed daughter centriole, begin moving toward opposite poles of the cell; the chromosomes can be seen as long threads. The nuclear membrane begins to disaggregate into small vesicles.

(c) Middle and late prophase. Chromosome condensation is completed; each visible chromosome structure is composed of two chromatids held together at their centromeres. Each chromatid contains one of the two newly replicated daughter DNA molecules. The microtubular spindle begins to radiate from the regions just adjacent to the centrioles, which are moving closer to their poles. Some spindle fibres reach from pole to pole; most go to chromatids and attach at kinetochores.

(d) Metaphase. The chromosomes move toward the equator of the cell, where they become aligned in the equatorial plane. The sister chromatids have not yet separated.

(e) Anaphase. The two sister chromatids separate into independent chromosomes. Each contains a centromere that is linked by a spindle fibre to one pole, to which it moves. Thus one copy of each chromosome is donated to each daughter cell. Simultaneously, the cell elongates, as do the pole-to-pole spindles. Cytokinesis begins as the cleavage furrow starts to form.

(f) Telophase. New membranes form around the daughter nuclei; the chromosomes uncoil and become less distinct, the nucleolus becomes visible again, and the nuclear membrane forms around each daughter nucleus. Cytokinesis is nearly complete, and the spindle disappears as the microtubules and other fibres depolymerise. Throughout mitosis the "daughter" centriole at each pole grows until it is full-length. At telophase the duplication of each of the original centrioles is completed, and new daughter centrioles will be generated during the next interphase.

(g) Interphase. Upon the completion of cytokinesis, the cell enters the $G_1$ phase of the cell cycle and proceeds again around the cycle.

It will be appreciated that cell cycling is an extremely important cell process. Deviations from normal cell cycling can result in a number of medical disorders. Increased and/or unrestricted cell cycling may result in cancer. Reduced cell cycling may result in degenerative conditions. Use of the compound of the present invention may provide a means to treat such disorders and conditions.

Thus, the compound of the present invention may be suitable for use in the treatment of cell cycling disorders such as cancers, including hormone dependent and hormone independent cancers.

In addition, the compound of the present invention may be suitable for the treatment of cancers such as breast cancer, ovarian cancer, endometrial cancer, sarcomas, melanomas, prostate cancer, testicular cancer, pancreatic cancer etc. and other solid tumours.

For some applications, cell cycling is inhibited and/or prevented and/or arrested, preferably wherein cell cycling is prevented and/or arrested. In one aspect cell cycling may be inhibited and/or prevented and/or arrested in the $G_2$/M phase. In one aspect cell cycling may be irreversibly prevented and/or inhibited and/or arrested, preferably wherein cell cycling is irreversibly prevented and/or arrested.

By the term "irreversibly prevented and/or inhibited and/or arrested" it is meant after application of a compound of the present invention, on removal of the compound the effects of the compound, namely prevention and/or inhibition and/or arrest of cell cycling, are still observable. More particularly by the term "irreversibly prevented and/or inhibited and/or arrested" it is meant that when assayed in accordance with the cell cycling assay protocol presented herein, cells treated with a compound of interest show less growth after Stage 2 of the protocol I than control cells. Details on this protocol are presented below.

Thus, the present invention provides compounds which: cause inhibition of growth of androgen receptor positive (AR+) and AR negative (AR−) prostate or testes cancer cells in vitro by preventing and/or inhibiting and/or arresting cell cycling; and/or cause regression of nitroso-methyl urea (NMU)-induced mammary tumours in intact animals (i.e. not ovariectomised), and/or prevent and/or inhibit and/or arrest cell cycling in cancer cells; and/or act in vivo by preventing and/or inhibiting and/or arresting cell cycling and/or act as a cell cycling agonist.

Cell Cycling Assay

Protocol 2

Procedure
Stage 1
MCF-7 breast cancer cells are seeded into multi-well culture plates at a density of $10^5$ cells/well. Cells were allowed to attach and grown until about 30% confluent when they are treated as follows:
Control—no treatment
Compound of Interest (COI) 20 µM
Cells are grown for 6 days in growth medium containing the COI with changes of medium/COI every 3 days. At the end of this period cell numbers were counted using a Coulter cell counter.

Stage 2
After treatment of cells for a 6-day period with the COI cells are re-seeded at a density of $10^4$ cells/well. No further treatments are added. Cells are allowed to continue to grow for a further 6 days in the presence of growth medium. At the end of this period cell numbers are again counted.
Cancer
As indicated, the compounds of the present invention may be useful in the treatment of a cell cycling disorder. A particular cell cycling disorder is cancer.

Cancer remains a major cause of mortality in most Western countries. Cancer therapies developed so far have included blocking the action or synthesis of hormones to inhibit the growth of hormone-dependent tumours. However, more aggressive chemotherapy is currently employed for the treatment of hormone-independent tumours.

Hence, the development of a pharmaceutical for anti-cancer treatment of hormone dependent and/or hormone independent tumours, yet lacking some or all of the side-effects associated with chemotherapy, would represent a major therapeutic advance.

We believe that the compound of the present invention provides a means for the treatment of cancers and, especially, prostate cancer.

In addition or in the alternative the compound of the present invention may be useful in the blocking the growth of cancers including leukaemias and solid tumours such as breast, endometrium, prostate, ovary and pancreatic tumours.
Other Therapies As previously mentioned, in one aspect the present invention provides use of a compound as described herein in the manufacture of a medicament for use in the therapy of a condition or disease associated with 17β-HSD.

It is also to be understood that the compound/composition of the present invention may have other important medical implications.

For example, the compound or composition of the present invention may be useful in the treatment of the disorders listed in WO-A-99/52890—viz:

In addition, or in the alternative, the compound or composition of the present invention may be useful in the treatment of the disorders listed in WO-A-98/05635. For ease of reference, part of that list is now provided: diabetes including Type II diabetes, obesity, cancer, inflammation or inflammatory disease, dermatological disorders, fever, cardiovascular effects, haemorrhage, coagulation and acute phase response, cachexia, anorexia, acute infection, HIV infection, shock states, graft-versus-host reactions, autoimmune disease, reperfusion injury, meningitis, migraine and aspirin-dependent anti-thrombosis; tumour growth, invasion and spread, angiogenesis, metastases, malignant ascites and malignant pleural effusion; cerebral ischaemia, ischaemic heart disease, osteoarthritis, rheumatoid arthritis, osteoporosis, asthma, multiple sclerosis, neurodegeneration, Alzheimer's disease, atherosclerosis, stroke, vasculitis, Crohn's disease and ulcerative colitis; periodontitis, gingivitis; psoriasis, atopic dermatitis, chronic ulcers, epidermolysis bullosa; corneal ulceration, retinopathy and surgical wound healing; rhinitis, allergic conjunctivitis, eczema, anaphylaxis; restenosis, congestive heart failure, endometriosis, atherosclerosis or endosclerosis.

In addition, or in the alternative, the compound or composition of the present invention may be useful in the treatment of disorders listed in WO-A-98/07859. For ease of reference, part of that list is now provided: cytokine and cell proliferation/differentiation activity; immunosuppressant or immunostimulant activity (e.g. for treating immune deficiency, including infection with human immune deficiency virus; regulation of lymphocyte growth; treating cancer and many autoimmune diseases, and to prevent transplant rejection or induce tumour immunity); regulation of haematopoiesis, e.g. treatment of myeloid or lymphoid diseases; promoting growth of bone, cartilage, tendon, ligament and nerve tissue, e.g. for healing wounds, treatment of burns, ulcers and periodontal disease and neurodegeneration; inhibition or activation of follicle-stimulating hormone (modulation of fertility); chemotactic/chemokinetic activity (e.g. for mobilising specific cell types to sites of injury or infection); haemostatic and thrombolytic activity (e.g. for treating haemophilia and stroke); antiinflammatory activity (for treating e.g. septic shock or Crohn's disease); as antimicrobials; modulators of e.g. metabolism or behaviour; as analgesics; treating specific deficiency disorders; in treatment of e.g. psoriasis, in human or veterinary medicine.

In addition, or in the alternative, the composition of the present invention may be useful in the treatment of disorders listed in WO-A-98/09985. For ease of reference, part of that list is now provided: macrophage inhibitory and/or T cell inhibitory activity and thus, anti-inflammatory activity; anti-immune activity, i.e. inhibitory effects against a cellular and/or humoral immune response, including a response not associated with inflammation; inhibit the ability of macrophages and T cells to adhere to extracellular matrix components and fibronectin, as well as up-regulated fas receptor expression in T cells; inhibit unwanted immune reaction and inflammation including arthritis, including rheumatoid arthritis, inflammation associated with hypersensitivity, allergic reactions, asthma, systemic lupus erythematosus, collagen diseases and other autoimmune diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other oto-rhino-laryngological diseases, dermatitis or other dermal diseases, periodontal diseases or other dental diseases, orchitis or epididimo-orchitis, infertility, orchidal trauma or other immune-related testicular diseases, placental dysfunction, placental insufficiency, habitual abortion, eclampsia, pre-eclampsia and other immune and/or inflammatory-related gynaecological diseases, posterior uveitis, intermediate uveitis, anterior uveitis, conjunctivitis, chorioretinitis, uveoretinitis, optic neuritis, intraocular inflammation, e.g. retinitis or cystoid macular oedema, sympathetic ophthalmia, scleritis, retinitis pigmentosa, immune and inflammatory components of degenerative fondus disease, inflammatory components of ocular trauma, ocular inflammation caused by infection, proliferative vitreo-retinopathies, acute ischaemic optic neuropathy, excessive scarring, e.g. following glaucoma filtration operation, immune and/or inflammation reaction against ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, inflammatory components of stokes, post-polio syndrome, immune and inflammatory components of psychiatric disorders, myelitis, encephalitis, subacute sclerosing pan-encephalitis, encephalomyelitis, acute neuropathy, subacute neuropathy, chronic neuropathy, Guillaim-Barre syndrome, Sydenham chora, myasthenia gravis, pseudo-tumour cerebri, Down's Syndrome, Huntington's disease, amyotrophic lateral sclerosis, inflammatory components of CNS compression or CNS trauma or infections of the CNS, inflammatory components of muscular atrophies and dystrophies, and immune and inflammatory related diseases, conditions or disorders of the central and peripheral nervous systems, post-traumatic inflammation, septic shock, infectious diseases, inflammatory complications or side effects of surgery, bone marrow transplantation or other transplantation complications and/or side effects, inflammatory and/or immune complications and side effects of gene therapy, e.g. due to infection with a viral carrier, or inflammation associated with AIDS, to suppress or inhibit a humoral and/or cellular immune response, to treat or ameliorate monocyte or leukocyte proliferative diseases, e.g. leukaemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue.

SUMMARY

In summation, the present invention provides compounds for use as hydroxysteroid dehydrogenase inhibitors, and pharmaceutical compositions for the same.

The present invention will now be described in further detail in the following examples.

EXAMPLES

The present invention will now be described only by way of example.

Synthetic Routes

The following compounds were synthesised.

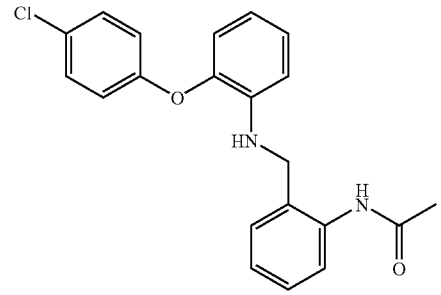

39
-continued
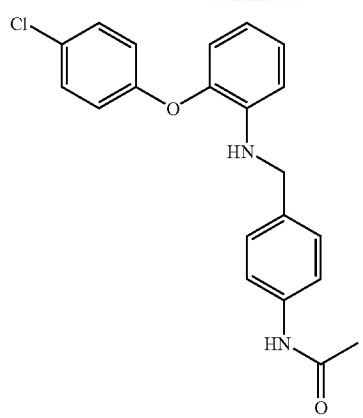
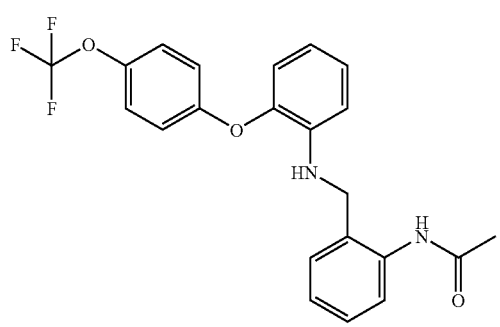
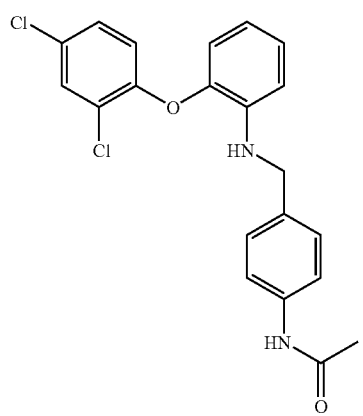
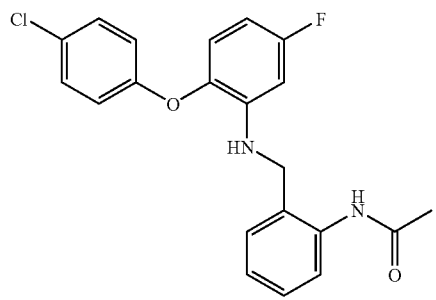
40
-continued
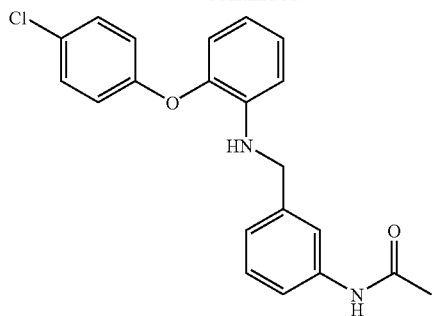
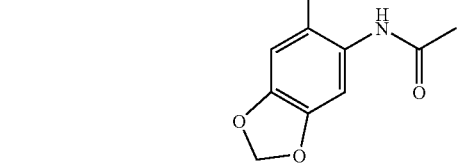
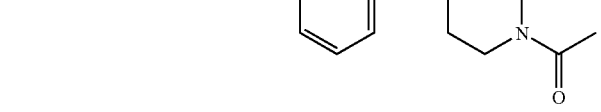
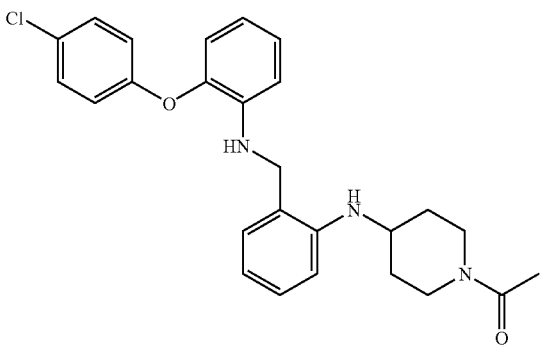

41
-continued
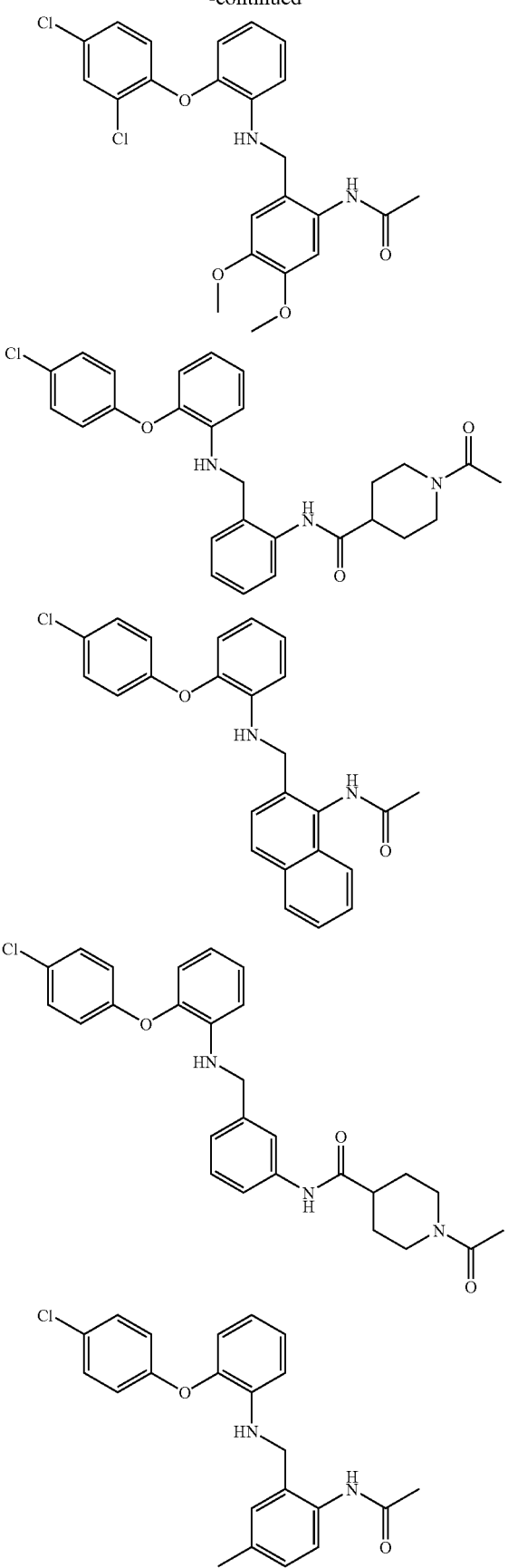
42
-continued
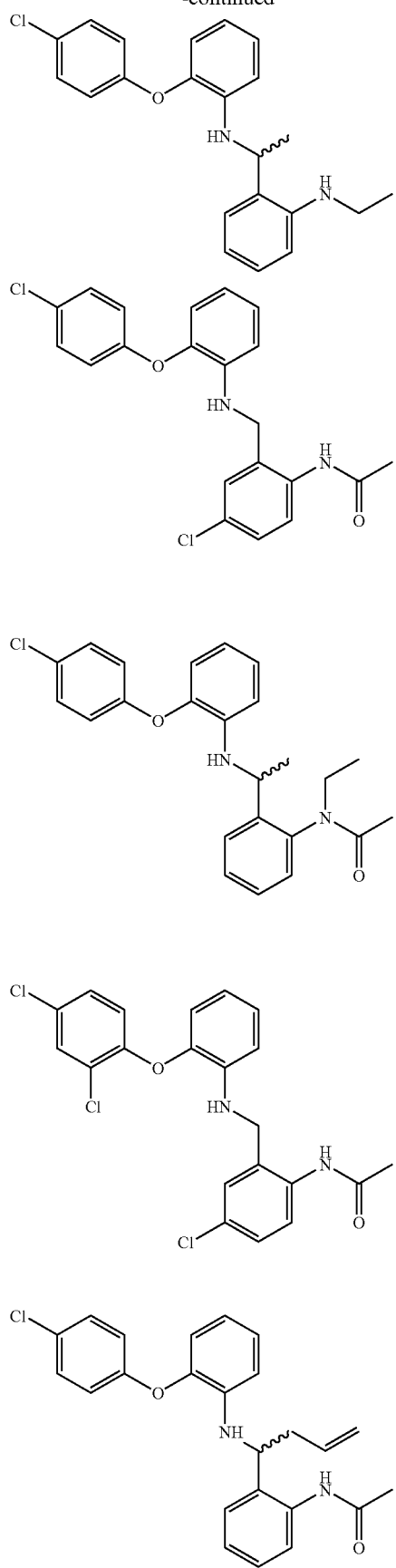

-continued
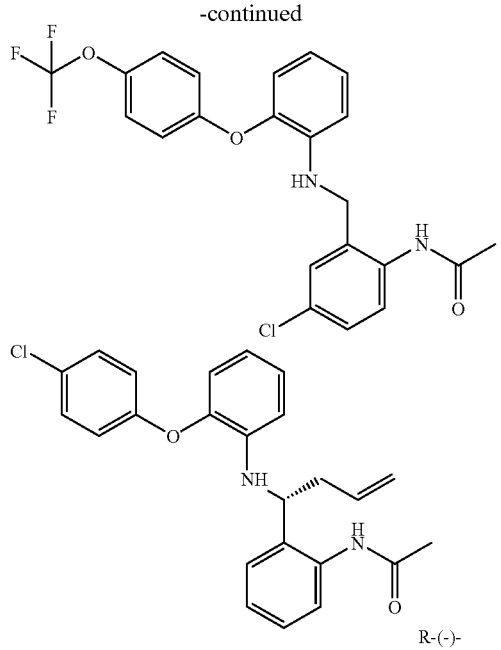
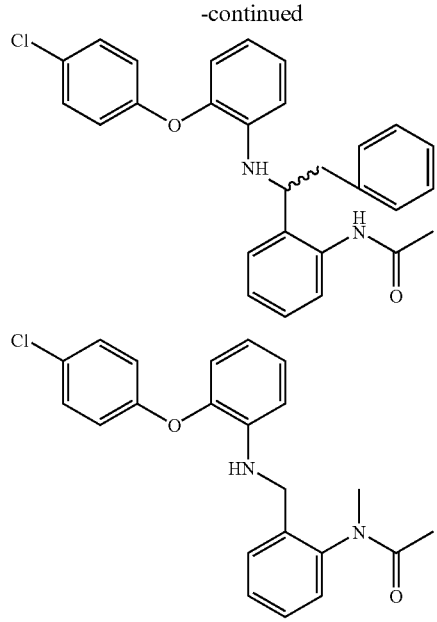
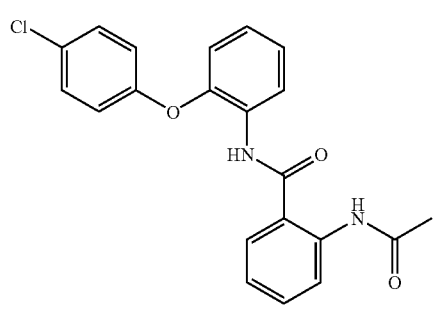
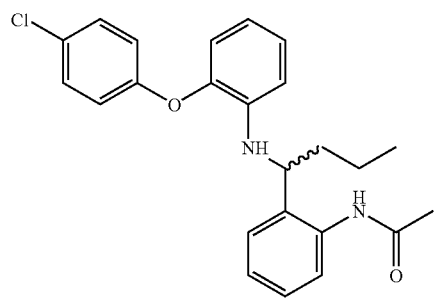
R-(-)-
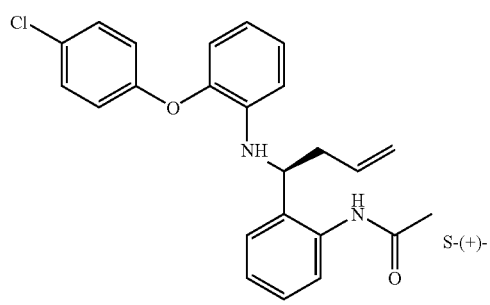
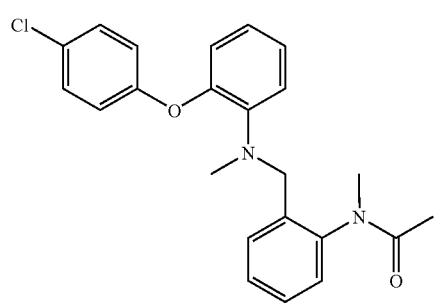
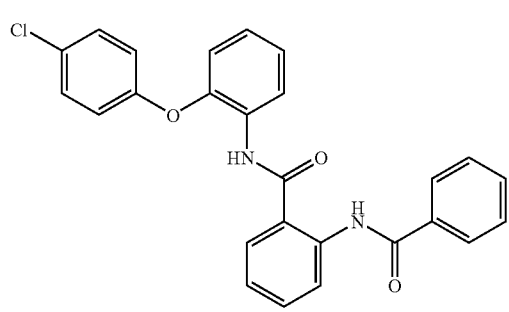
S-(+)-
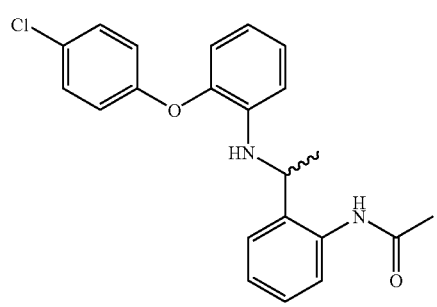

45
-continued
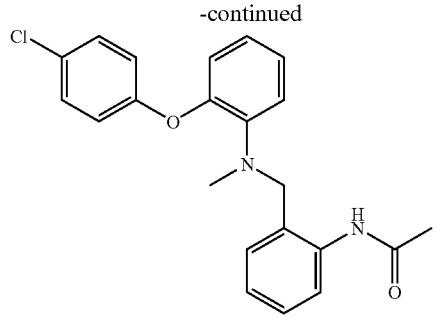
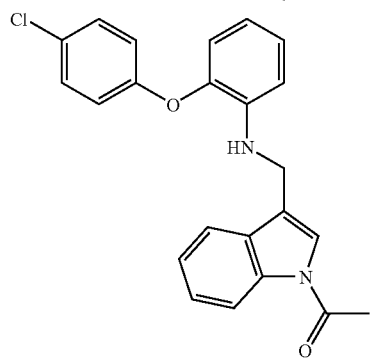
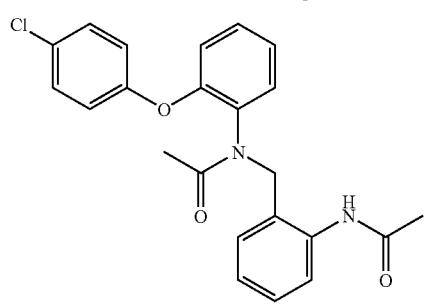
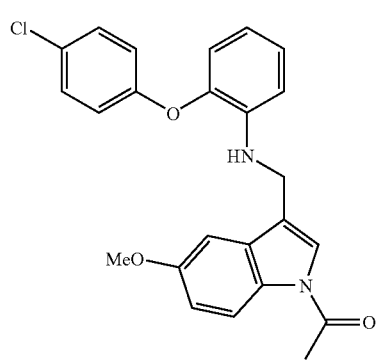
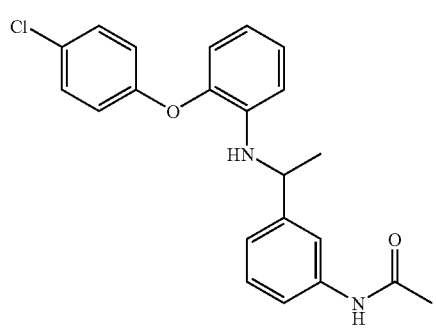
46
-continued
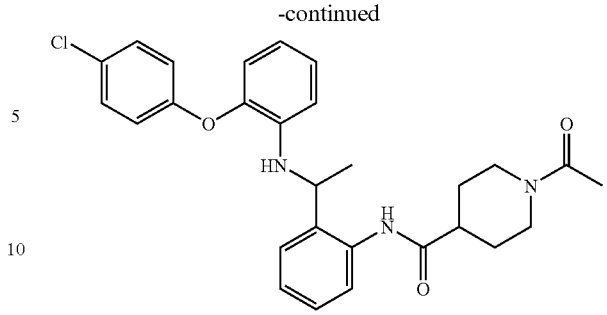
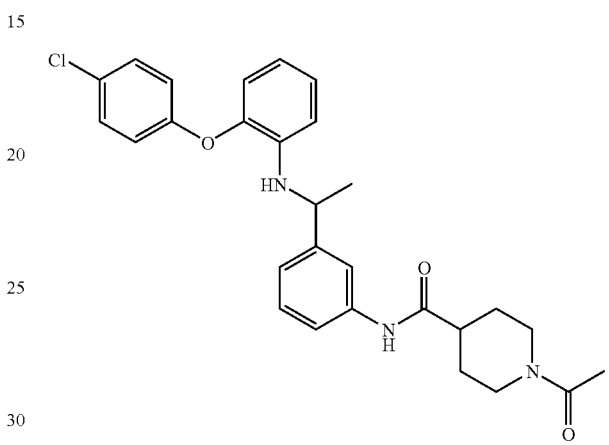
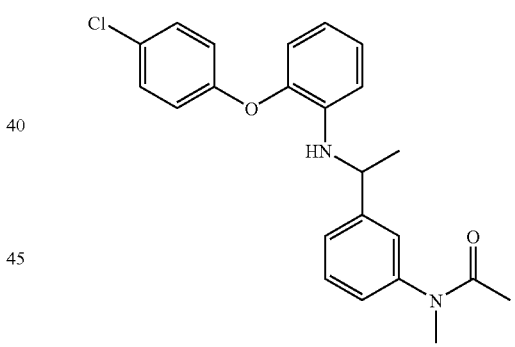
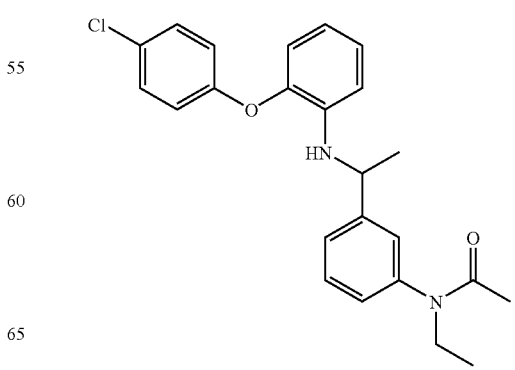

-continued

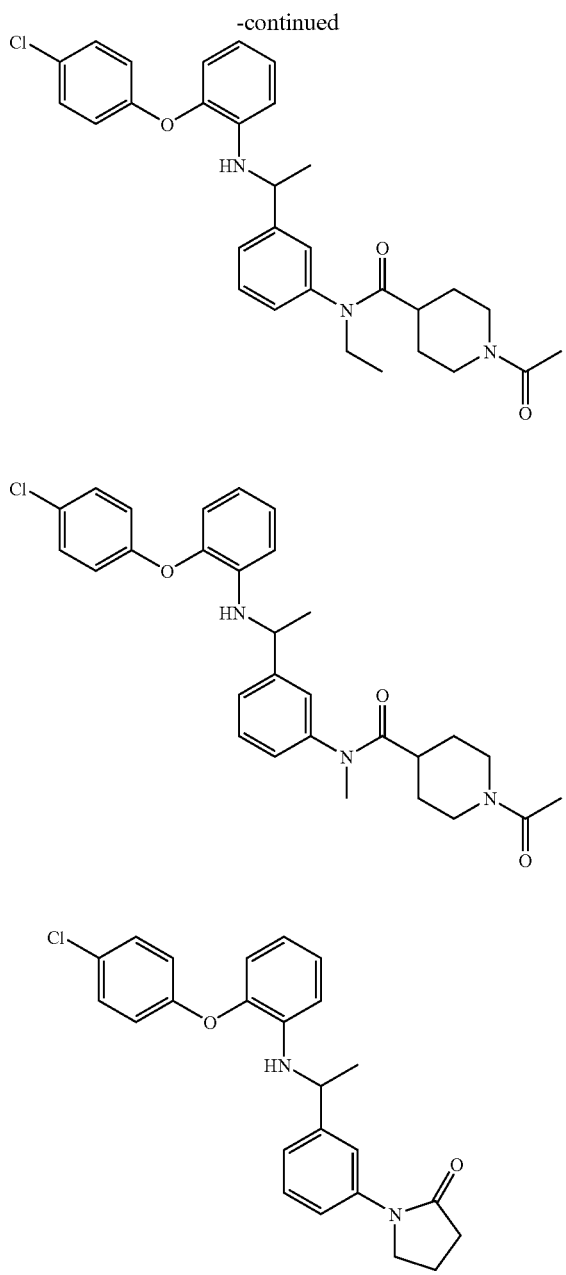

General Procedures
General Procedure for the Reduction of Substituted 2-Nitrobenzaldehyde.

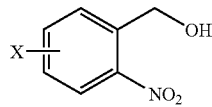

A solution of the desired substituted 2-nitrobenzaldehyde in EtOH (5 ml/mmol) was cooled to 0° C. and to this was added NaBH$_4$ (1.5 eq) and the resulting solution was stirred at r.t. for 2 h. The EtOH was removed in vacuo and sat. NH$_4$Cl solution was added and the mixture was then extracted with DCM and dried (MgSO$_4$). It was then evaporated in vacuo to yield the desired substituted 2-nitrobenzyalcohol.

General Procedure for the Reduction of the Substituted 2-Nitrobenzylalcohol.

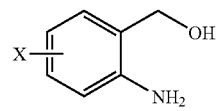

To a refluxing mixture of iron (5.5 eq.) and ammonium chloride (0.7 eq.) in a 10:1 mixture of EtOH: H$_2$O, the substituted 2-nitrobenzylalcohol (1 eq.) was added. This reaction mixture was stirred at reflux for between 1 and 4 h, and followed by TLC, it was then allowed to cool to room temperature and the solvent was removed in vacuo. The residue was re-dissolved in DCM and washed with sat. aqueous sodium bicarbonate. The organic layer was dried (MgSO$_4$) filtered and evaporated in vacuo to afford the desired 2-aminobenzyalcohol.

General Procedure for the Acylation of Substituted 2-Aminobenzylalcohols.

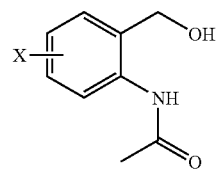

To a solution of the substituted 2-aminobenzylalcohol and TEA (3 eq) in DCM (10 ml/1 mmol) at 0° C., was added acetyl chloride (6 eq.). The resulting solution was allowed to warm to r.t. and stirred for 18 h. NaHCO$_3$ was then added and the crude mixture was repeatedly extracted with DCM (with a trace of MeOH). The organic layers were then washed with 1M HCl. The organic layers were combined and dried (MgSO$_4$) filtered and evaporated in vacuo. The resulting solid was redissolved in MeOH (40 ml/1 mmol) and to this was added NaOH (3 eq) and the reaction was stirred at r.t. for 2 h. The solvent was evaporated in vacuo and H$_2$O was added, the crude mixture was repeatedly extracted with EtOAc. The organic layers were combined and dried (MgSO$_4$), filtered and evaporated in vacuo to obtain the desired 2-acetamide benzylalcohol.

General Procedure for the Dess-Martin Periodinane Oxidation of Alcohols.

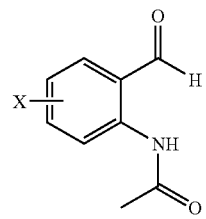

To a solution of the 2-acetamide alcohol in DCM (50 ml/1 mmol) was added Dess-Marin Periodinane (1.5 eq.) the resulting solution was stirred at r.t for 10 min. Sodium thiosulphate (4.5 eq) in NaHCO$_3$ was then added and the mixture was repeatedly extracted with DCM. The organic layers were combined, dried (MgSO$_4$) filtered and evaporated in vacuo.

The crude mixture was purified using flash chromatography to afford the desired aldehyde.

General Procedure for the Reductive Amination of the Substituted Diphenylether Aniline with the Substituted 2-Acetamide Benzaldehyde.

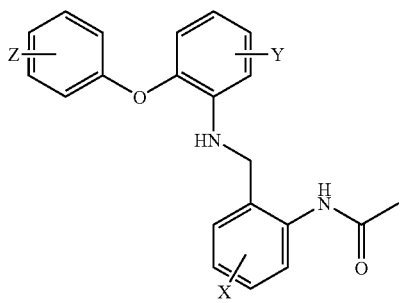

To a solution of the diphenylether aniline (1.5 eq) and aldehyde (1 eq) in DCE (2 ml/1 mmol) was added acetic acid (3 eq) and sodium triacetoxyborohydride (2.5 eq). The resulting reaction mixture was stirred at r.t. for 2-18 h. NaHCO$_3$ was then added and repeatedly extracted with DCM. The organic layers were combined, dried (MgSO$_4$) filtered and evaporated in vacuo. The crude mixture was purified using flash chromatography to afford the desired compound.

Synthetic Procedures

Synthesis of 2-amino-benzaldehyde, C$_7$H$_7$NO, MW 121.14

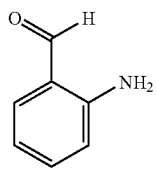

Using the general procedure for the reduction of the 2-nitrobenzylalcohol the desired compound was isolated as a yellow oil, 794 mg, 99% yield.

R.f 0.35 (DCM),

LCMS: t$_r$=3.04 min (50% to 95% MeOH in water at 0.5 ml/min to 1.0 ml/min over 5 min), m/z M$^+$H 122.15, $^1$H NMR (CDCl$_3$, 270 MHz): δ 6.12 (2H, s, NH$_2$), 6.63 (1H, d, J=8.4 HZ, ArH), 6.70-6.76 (1H, m, ArH), 7.26-7.32 (1H, m, ArH), 7.46 (1H, dd, J=1.5, 7.7 Hz, ArH), 9.85 (1H, s, CHO).

Synthesis of N-(2-formyl-phenyl)-acetamide, C$_9$H$_9$NO$_2$, MW 163.17

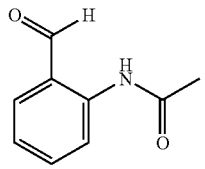

Using the general procedure for the acylation of substituted 2-aminobenzylalcohols the title compound was obtained as a yellow solid, 190 mg, 71% yield.

R.f 0.68 (DCM), m.p. 54-57° C., $^1$H NMR (CDCl$_3$, 270 MHz): δ 2.24 (3H, s, CH$_3$), 7.21 (1H, td, J=1.2, 7.7 Hz, ArH), 7.56-7.63 (1H, m, ArH), 7.65 (1H, dd, J=1.5, 7.7 Hz, ArH), 8.72 (1H, d, J=8.4 Hz, ArH), 9.90 (1H, s, CHO), 11.12 (1H, s, NH).

Synthesis of N-(2-([2-(4-chloro-phenoxy)- phenylamino]-methyl)-phenyl)-acetamide, C$_{21}$H$_{19}$ClN$_2$O$_2$, MW 366.84

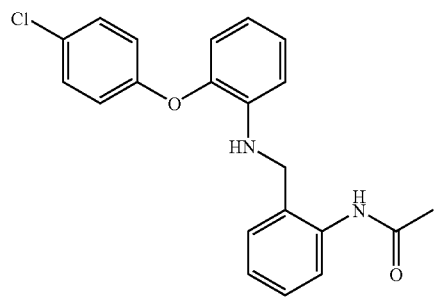

To a solution of 2-(4-chloro-phenoxy)-phenylamine (0.128 g, 0.58 mmol) and N-(2-formyl-phenyl)-acetamide (0.19 g, 1.16 mmol) in DCE (2.6 ml) was added acetic acid (0.25 ml) and sodium triacetoxyborohydride (0.31 g, 1.45 mmol). The resulting reaction mixture was heated in a CEM microwave for 10 minutes at 140° C. NaHCO$_3$ was then added and the mixture was repeatedly extracted with EtOAc. The organic layers were combined, dried (MgSO$_4$) filtered and evaporated in vacuo. The crude mixture was purified using flash chromatography (0-100% DCM in hexane) to afford the title compound as a white solid, 80 mg, 38% yield.

R.f 0.33 (DCM), m.p. 194-196° C.,

LCMS: t$_r$=1.36 min (95% MeOH in H$_2$O), m/z M–H 365.4,

HPLC: t$_r$=5.1 min (90% ACN in H$_2$O, 0.5 ml/min), 98%, $^1$H NMR (DMSO, 400 MHz): δ 2.02 (3H, s, CH$_3$), 4.27 (2H, d, J=5.6 Hz, CH$_2$), 5.95 (1H, s, NH), 6.46 (1H, d, J=8.4 Hz, ArH), 6.55 (1H, td, J=0.8, 7.6 Hz, ArH), 6.84 (1H, dd, J=1.6, 8.0, ArH), 6.89-6.95 (3H, m, ArH), 7.07-7.11 (1H, m, ArH), 7.16-7.22 (2H, m, ArH), 7.35-7.41 (3H, m, ArH), 9.47 (1H, br.s, NHCO).

$^{13}$C NMR (DMSO, 101 MHz): 23.2 (CH$_3$), 42.6 (CH$_2$), 111.7, 116.0, 118.3, 120.2, 125.2, 125.3, 125.6 (ArCH), 126.0 (ArC), 126.7, 126.9, 129.6 (ArCH), 133.5, 135.8, 140.5, 141.6, 156.7 (ArC), 168.5 (CO).

HRMS: Calcd for C$_{21}$H$_{19}$ClN$_2$O$_2$ (M+H)$^+$ 367.1208. found (M+H)$^+$ 367.1204.

Anal. calcd for $C_{21}H_{19}ClN_2O_2$: C, 68.76; H, 5.22; N, 7.64%. Found: C, 69.0; H, 5.28; N, 7.52%.

Synthesis of N-(2-([2-(4-trifluoromethoxy-phenoxy)-phenylamino]-methyl)-phenyl)-acetamide, $C_{22}K_9F_3N_2O_3$, MW 416.39

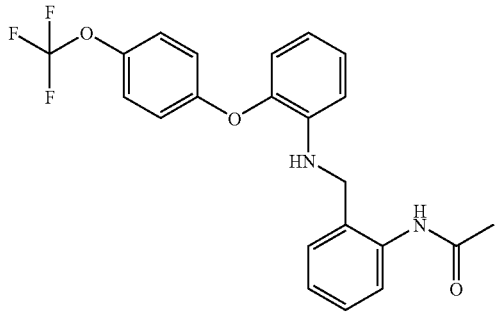 [SMILES: CC(=O)Nc1ccccc1CNc1ccccc1Oc1ccc(OC(F)(F)F)cc1]

Using the general procedure for the reductive amination of the substituted diphenylether aniline with the substituted 2-acetamide benzaldehyde the desired compound was isolated as a white solid, 155 mg, 55% yield.

R.f 0.4 (1:1, EtOAc:Hexane),
m.p. 98-100° C.,
LCMS: $t_r$=1.07 min (95% MeOH in $H_2O$), m/z M–H 415.09,
HPLC: $t_r$=2.22 min (90% ACN in $H_2O$), 99%,
$^1$H NMR ($CDCl_3$, 270 MHz): δ 1.94 (3H, s, $CH_3$), 4.3 (3H, s, $CH_2$ and NH), 6.79-6.96 (5H, m, ArH), 7.06-7.17 (3H, m, ArH), 7.25-7.34 (3H, m, ArH), 8.01 (1H, d, J=8.15, ArH), 8.54 (1H, br.s, NHCO).
$^{13}$C NMR ($CDCl_3$, 68 MHz): δ 24.5 ($CH_3$), 47.8 ($CH_2$), 113.8, 118.1, 119.6, 119.7 (ArCH), 122.5 (ArC), 122.8, 124.6, 125.7 (ArCH), 127.6 (ArC), 128.9, 129.6 (ArCH), 137.5, 139.9, 143.9, 144.4 (ArC), 155.9 ($OCF_3$), 168.5 (CO).
$^{19}$F NMR ($CDCl_3$, 376 MHz): δ –58.29 ($OCF_3$),
HRMS: Calcd for $C_{22}H_{19}F_3N_2O_3$ (M+Na)$^+$ 439.1240. found (M+Na)$^+$ 439.1240.
Anal. calcd for $C_{22}H_{19}F_3N_2O_3$: C, 63.46; H, 4.60; N, 6.73%. Found: C, 63.5; H, 4.62; N, 7.0%.

Synthesis of N-(2-([2-(4-chloro-phenoxy)-5'- fluoro-phenylamino]-methyl)-phenyl)-acetamide, $C_{21}H_{18}ClFN_2O_2$, MW 384.83

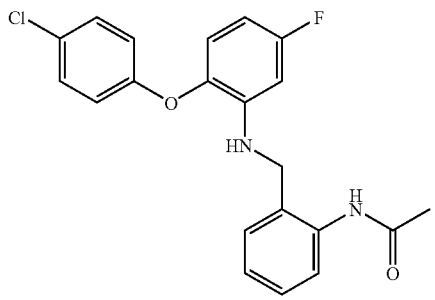 [SMILES: CC(=O)Nc1ccccc1CNc1cc(F)ccc1Oc1ccc(Cl)cc1]

Using the general procedure for the reductive amination of the substituted diphenylether aniline with the substituted 2-acetamide benzaldehyde the desired compound was isolated as a white solid, 68 mg, 27% yield.

R.f 0.4 (1:1, EtOAc:Hexane),
m.p. 178-180° C.,
LCMS: $t_r$=0.98 min (95% MeOH in $H_2O$), m/z M–H 383.28,
HPLC: $t_r$=2.87 min (90% ACN in $H_2O$), 99%,
$^1$H NMR ($CDCl_3$, 270 MHz): δ 2.03 (3H, s, $CH_3$), 4.23 (2H, d, J=5.0 Hz, $CH_2$), 4.42 (1H, t, J=4.9 Hz, NH), 6.41-6.58 (2H, m, ArH), 6.80-6.88 (3H, m, ArH), 7.10 (1H, t, J=7.2 Hz, ArH), 7.22-7.32 (4H, m, ArH), 7.86 (1H, d, J=7.9 Hz, ArH), 8.19 (1H, br.s, NHCO),
$^{13}$C NMR ($CDCl_3$, 68 MHz): δ 24.3 ($CH_3$), 46.8 ($CH_2$), 100.7 (d, J=28.1 Hz, ArH), 104.6 (d, J=23.7 Hz, ArCH), 118.0 (ArCH), 120.8 (d, J=10.0 Hz, ArCH), 123.6 (ArCH), 128.1 (d, J=11.8 Hz, ArC), 128.9, 129.4, 129.9 (ArCH), 136.9, 139.2 (ArC), 141.3 (d, J=10.6 Hz, ArC), 156.3, 158.8, 162.3 (ArC), 168.7 (CO).
$^{19}$F NMR ($CDCl_3$, 376 MHz): δ 115.43-115.57 (m, ArF),
HRMS: Calcd for $C_{21}H_{18}ClFN_2O_2$ (M+H)$^+$ 383.0968. found (M+H)$^+$ 383.0965.

Synthesis of 6-amino-benzo[1,3]dioxole-5-carbaldehyde, $C_8H_7NO_3$, MW 165.15

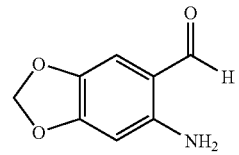 [SMILES: Nc1cc2c(cc1C=O)OCO2]

Using the general procedure for the reduction of substituted 2-nitrobenzylalcohol the desired compound was obtained as a brown solid, 360 mg, 85% yield.

R.f 0.67 (DCM),
$^1$H NMR ($CDCl_3$, 270 MHz): δ 5.90 (2H, s, $CH_2$), 6.11 (1H, s, ArH), 6.29 (2H, br.s, NH), 6.79 (1H, s, ArH), 9.57 (1H, s, CHO).

Synthesis of N-(6-formyl-benzo[1,3]dioxol-5-yl)-acetamide, $C_{10}H_9NO_4$, MW 207.18

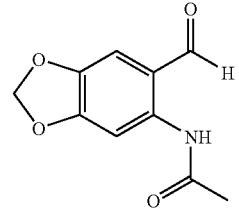

Using the general procedure for the acylation of substituted 2-aminobenzylalcohols the title compound was obtained as a dark yellow solid, 180 mg, 78% yield.

R.f 0.35 (DCM),
m.p. 133-137° C., $^1$H NMR (CDCl$_3$, 270 MHz): δ 2.21 (3H, s, CH$_3$), 6.05 (2H, s, CH$_2$), 6.98 (1H, s, ArH), 8.34 (1H, s, ArH), 9.65 (1H, s, CHO), 11.46 (1H, s, NH).

Synthesis of N-(6-[2-(4-chloro-phenoxy)-phenylamino]-methyl-benzo[1,3]dioxol-5-yl)-acetamide, C$_{22}$H$_{19}$ClN$_2$O$_4$, MW 410.85

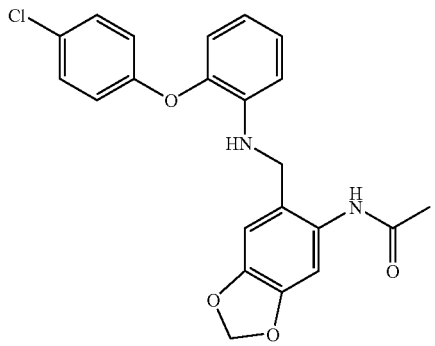 [SMILES: CC(=O)Nc1cc2c(cc1CNc1ccccc1Oc1ccc(Cl)cc1)OCO2]

Using the general procedure for the reductive amination of the substituted diphenylether aniline with the substituted 2-acetamide benzaldehyde the desired compound was isolated as a light cream solid, 540 mg, 29% yield.

R.f 0.75 (DCM), m.p. 154-156° C.,

LCMS: t$_r$=1.3 min (95% MeOH in water), m/z M$^-$H 409.45,

HPLC: t$_r$=4.7 min (90% ACN in H$_2$O), 98%, $^1$H NMR (CDCl$_3$, 400 MHz,): δ 1.95 (3H, s, CH$_3$), 4.18 (2H, s, NHCH$_2$), 4.23 (1H, s, NH), 5.93 (2H, s, CH$_2$O), 6.74 (1H, s, ArH), 6.77-6.81 (1H m, ArH), 6.86-6.89 (3H, m, ArH), 7.10 (1H, dt, J=4.0, 8.8 Hz, ArH), 7.24-7.27 (2H, m, ArH), 7.44 (1H, s, ArH), 8.23 (1H, s, ArH), $^{13}$C NMR (CDCl$_3$, 101 MHz): δ 24.2 (CH$_3$), 47.2 (CH$_2$NH), 101.4 (CH$_2$O), 105.3, 109.1, 113.4, 118.5, 119.2, 119.4 (ArCH), 121.7 (ArC), 125.4 (ArCH), 128.0 (ArC), 129.8 (ArCH), 131.1, 139.6, 143.7, 144.7, 147.4, 155.9 (ArC), 168.3 (CO).

HRMS: Calcd for C$_{22}$H$_{19}$ClN$_2$O$_4$ (M+H)$^+$ 409.0961. found (M+H)$^+$ 409.0957.

Synthesis of (2-amino-4,5-dimethoxy-phenyl)-methanol, C$_9$H$_{13}$NO$_3$, MW 183.20

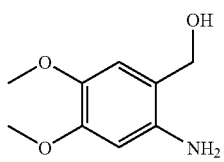

Using the general procedure for the reduction of the substituted 2-nitrobenzylalcohol the desired compound was obtained as a brown oil, 764 mg, 93% yield.

R.f 0.17 (EtOAc), $^1$H NMR (CDCl$_3$, 270 MHz,): δ 3.30 (2H, br.s, NH$_2$), 3.78 (3H, s, OCH$_3$), 3.81 (3H, s, OCH$_3$), 4.58 (2H, s, CH$_2$), 6.29 (1H, s, ArH), 6.63 (1H, s, ArH).

Synthesis of N-(2-hydroxymethyl-4,5-dimethoxy-phenyl)-acetamide, C$_{11}$H$_{15}$NO$_4$, MW 225.24

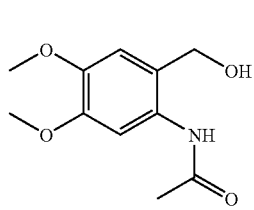 [SMILES: COc1cc(CO)c(NC(C)=O)cc1OC]

Using the general procedure for the acylation of substituted 2-aminobenzylalcohols the title compound was obtained as a yellow, waxy solid, 277 mg, 59% yield.

R.f 0.48 (EtOAc), $^1$H NMR (CDCl$_3$, 270 MHz,): δ 2.14 (3H, s, CH$_3$), 2.85, (1H, br.s, OH), 3.82 (3H, s, OCH$_3$), 3.84 (3H, s, OCH$_3$), 4.56 (2H, s, CH$_2$), 6.69 (1H, s, ArH), 7.46 (1H, s, ArH).

Synthesis of N-(2-formyl-4,5-dimethoxy-phenyl)-acetamide, C$_{11}$H$_{13}$NO$_4$, MW 223.23

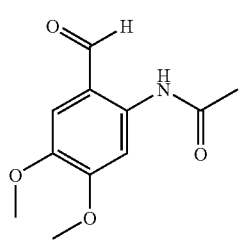 [SMILES: COc1cc(C=O)c(NC(C)=O)cc1OC]

Using the general procedure for the Dess-Martin Periodinane oxidation of alcohols the title compound was obtained as a brown solid, 137 mg, 50% yield.

R.f 0.22 (EtOAc), m.p. 138-140° C., $^1$H NMR (CDCl$_3$, 270 MHz): δ 2.23 (3H, s, CH$_3$), 3.90 (3H, s, OCH$_3$), 3.98 (3H, s, OCH$_3$), 7.02 (1H, s, ArH), 8.46 (1H, s, ArH), 9.74 (1H, s, CHO), 11.32 (1H, br.s, NH).

Synthesis of N-(2-[2-(4-chloro-phenoxy)-phenylamino]-methyl-4,5-dimethoxy-phenyl)-acetamide, C$_{23}$H$_{23}$ClN$_2$O$_4$, MW 426.89

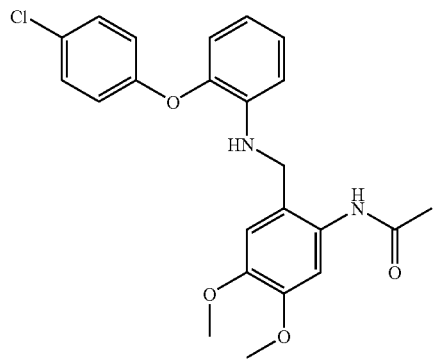 [SMILES: COc1cc(CNc2ccccc2Oc2ccc(Cl)cc2)c(NC(C)=O)cc1OC]

Using the general procedure for the reductive amination of the substituted diphenylether aniline with the substituted 2-acetamide benzaldehyde the resulting reaction mixture was stirred at r.t. for 2 h, then it was subjected to microwave heating for 5 min at 140° C. NaHCO$_3$ was then added and the mixture was repeatedly extracted with DCM. The organic layers were combined, dried (MgSO$_4$) filtered and evaporated in vacuo. The crude mixture was purified using flash chromatography (100% EtOAc) to afford the title compound as a cream solid, 20 mg, 11% yield.

R.f 0.44 (EtOAc), m.p. 117-118° C.,

LCMS: t$_r$=0.97 min (95% MeOH in water), m/z M–H 425.16,

HPLC: t$_r$=1.99 min (90% ACN in H$_2$O), 98%, $^1$H NMR (CDCl$_3$, 270 MHz): δ 1.94 (3H, s, CH$_3$), 3.81 (3H, s, OCH$_3$), 3.85 (3H, s, OCH$_3$), 4.22 (3H, br.s, CH$_2$ and NH), 6.74-6.90 (6H, m, ArH), 7.06-7.12 (1H, m, ArH), 7.21-7.26 (2H, m, ArH), 7.57 (1H, s, ArH), 8.26 (1H, br.s, NHCO).

$^{13}$C NMR (CDCl$_3$, 68 MHz): δ 24.4 (CH$_3$), 47.2 (CH$_2$), 56.11, 56.27 (OCH$_3$), 107.4, 112.5, 113.6, 118.5, 119.3, 119.6 (ArCH), 120.2 (ArC), 125.6 (ArCH), 128.1 (ArC), 129.9, (ArCH), 130.6, 139.9, 143.7, 148.7, 156.0 (ArC), 168.5 (CO).

HRMS: Calcd for C$_{23}$H$_{23}$ClN$_2$O$_4$ (M+Na)$^+$ 449.1230. found (M+Na)$^+$449.1239.

Synthesis of N-(2-([2-(2,4-dichloro-phenoxy)-phenylamino]-methyl)-4,5-dimethoxy-phenyl)-acetamide, C$_{23}$H$_{22}$Cl$_2$N$_2$O$_4$, MW 461.34

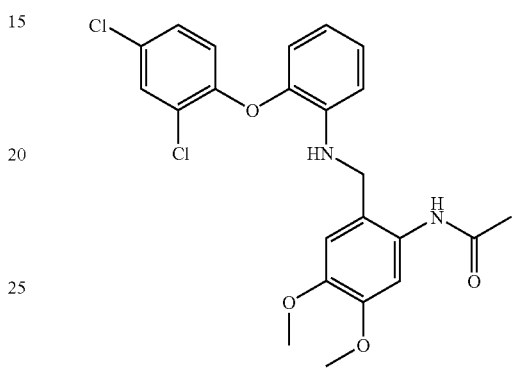

2-(2,4-Dichloro-phenoxy)-phenylamine hydrochloride (135 mg, 0.47 mmol) was dissolved in DCM (10 ml) and to this was added K$_2$CO$_3$ (128 mg, 0.94 mmol) the reaction was then stirred at r.t. for 30 min. H$_2$O was added to the reaction and the mixture was extracted with DCM. The organic layers were combined, dried (MgSO$_4$) filtered and evaporated in vacuo. The resulting free amine was dissolved in DCE (2 ml) and to this was added N-(2-formyl-4,5-dimethoxy-phenyl)-acetamide (69 mg, 0.31 mmol) acetic acid (0.12 ml) and sodium triacetoxyborohydride (164 mg, 0.8 mmol). The resulting reaction mixture was stirred at r.t. for 2 h. NaHCO$_3$ was then added, and repeatedly extracted with DCM. The organic layers were combined, dried (MgSO$_4$), filtered and evaporated in vacuo. The crude mixture was purified using flash chromatography (0-50% EtOAc in hexane) to afford the title compound as an off-white solid, 55 mg, 38% yield.

R.f 0.58 (EtOAc), m.p. 128-131° C.,

LCMS: t$_r$=1.1 min (95% MeOH in water), m/z M–H 459.24,

HPLC: t$_r$=2.2 min (90% ACN in H$_2$O), 96%, $^1$H NMR (CDCl$_3$, 270 MHz): δ 1.98 (3H, s, CH$_3$), 3.83 (3H, s, OCH$_3$), 3.87 (3H, s, OCH$_3$), 4.26 (2H, s, CH$_2$), 4.34 (1H, br.s, NH), 6.75-6.77 (3H, m, ArH), 6.83-6.91 (2H, m, ArH), 7.02-7.11 (1H, m, ArH), 7.15 (1H, dd, J=1.7, 8.7 Hz, ArH), 7.61 (1H, s, ArH), 8.31 (1H, br.s, NHCO).

$^{13}$C NMR (CDCl$_3$, 101 MHz): δ 24.5 (CH$_3$), 47.2 (CH$_2$), 56.1, 56.3 (OCH$_3$), 104.0 (ArC), 107.4, 112.5, 113.6, 118.0, 119.1, 120.0, 125.4 (ArCH), 125.5, 125.8 (ArC), 128.1 (ArCH), 129.0 (ArC), 130.6 (ArCH), 139.1, 143.7, 146.0, 148.7, 151.5 (ArC), 168.5 (CO).

HRMS: Calcd for $C_{23}H_{22}Cl_2N_2O_4$ (M+H)$^+$ 461.1029. found (M+H)$^+$ 461.1028.

Synthesis of (1-nitro-naphthalen-2-yl)-methanol, $C_{11}H_9NO_3$, MW 203.19

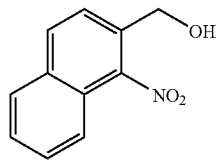 [SMILES: O=[N+]([O-])c1c(CO)ccc2ccccc12]

Using the general procedure for the reduction of substituted 2-nitrobenzaldehyde the desired product was obtained as a dark yellow solid, 1 g, >99% yield.
R.f 0.59 (EtOAc),
m.p 78-80° C.,
$^1$H NMR (CDCl$_3$, 270 MHz): δ 2.32 (1H, br.s, OH), 4.82 (2H, s, CH$_2$), 7.48-7.65 (3H, m, ArH), 7.81-7.90 (2H, m, ArH), 7.99 (1H, d, J=8.4, ArH).

Synthesis of (1-amino-naphthalen-2-yl)-methanol, $C_{11}H_{11}NO$, MW 173.21

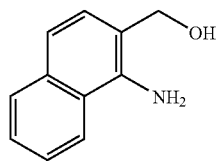

Using the general procedure for the reduction of the substituted 2-nitrobenzylalcohol, the desired product was obtained, 730 mg, 86% yield.
R.f 0.62 (EtOAc),
LCMS: t$_r$=1.3 min (80% MeOH in water), m/z M−H 171.88,
HPLC: t$_r$=2.19 min (70% ACN in water), 87%,
$^1$H NMR (CDCl$_3$, 270 MHz): δ 4.85 (2H, s, CH$_2$), 7.21-7.25 (2H, m, ArCH), 7.41-7.47 (2H, m, ArH), 7.74-7.85 (2H, m, ArH).

Synthesis of N-(2-hydroxymethyl-naphthalen-1-yl)-acetamide, $C_{13}H_{13}NO_2$, MW 215.25

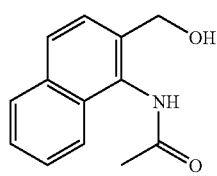 [SMILES: CC(=O)Nc1c(CO)ccc2ccccc12]

Using the general procedure for the acylation of substituted 2-aminobenzylalcohols the desired product was obtained as a yellow solid, 377 mg, 82% yield.
R.f 0.58 (EtOAc),
m.p. 105-108° C.,
$^1$H NMR (CDCl$_3$, 270 MHz): δ 2.32 (3H, s, CH$_3$), 3.29 (1H, br.s, OH), 4.63 (2H, s, CH$_2$), 7.40-7.44 (3H, m, ArH), 7.77-7.80 (3H, m, ArH).

Synthesis of N-(2-formyl-naphthalen-1-yl)-acetamide, $C_{13}H_{11}NO_2$, MW 213.23

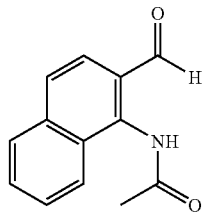 [SMILES: CC(=O)Nc1c(C=O)ccc2ccccc12]

Using the general procedure for the Dess-Martin Periodinane oxidation of alcohols the desired product was obtained, 59 mg, 77% yield.
R.f 0.45 (EtOAc),
$^1$H NMR (CDCl$_3$, 270 MHz): δ 2.28 (3H, s, CH$_3$), 7.55-7.92 (5H, m, ArH), 7.99-8.03 (1H, m, ArH), 9.31 (1H, br.s, NH), 10.18 (1H, s, CHO).

Synthesis of N-(2-[2-(4-chloro-phenoxy)-phenylamino]-methyl-naphthalen-1-yl)-acetamide, $C_{25}H_{21}ClN_2O_2$, MW 416.90

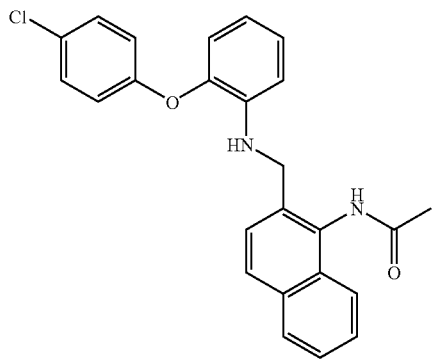 [SMILES: CC(=O)Nc1c(CNc2ccccc2Oc2ccc(Cl)cc2)ccc2ccccc12]

Using the general procedure for the reductive amination of the substituted diphenylether aniline with the substituted 2-acetamide benzaldehyde the desired compound was isolated, 28 mg, 24% yield.
R.f 0.38 (EtOAc),
m.p. 153-155° C.,
LCMS: t$_r$=1.14 min (95% MeOH in water), m/z M−H 415.34,
HPLC: t$_r$=2.26 min (90% ACN in water), 96%,
$^1$H NMR (CDCl$_3$, 270 MHz,): δ 2.28 (3H, s, CH$_3$), 4.42 (2H, s, CH$_2$), 4.53 (1H, br.s, NH), 6.63-6.73 (2H, m, ArH), 6.83-6.91 (3H, m, ArH), 6.97-7.03 (1H, m, ArH), 7.21-7.24 (2H, m, ArH), 7.42-7.51 (4H, m, ArH), 7.75 (1H, d, J=8.4 Hz, ArH), 7.80-7.85 (2H, m, ArH and NHCO).
$^{13}$C NMR (CDCl$_3$, 68 MHz): 23.5 (CH$_3$), 45.4 (CH$_2$), 112.4, 117.7, 118.5, 119.6, 122.6, 125.5, 126.0, 126.1 (ArCH), 127.8 (ArC), 128.2, 128.4, 129.8 (ArCH), 130.5, 130.6, 133.4, 133.7, 140.2, 142.9, 156.5 (ArC), 169.4 (CO).

HRMS: Calcd for $C_{25}H_{21}ClN_2O_2$ (M+H)$^+$ 439.1184. found (M+H)$^+$ 439.1190.

Synthesis of (2-amino-5-methyl-phenyl)-methanol, $C_8H_{11}NO$, MW 137.18

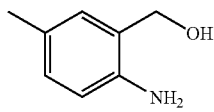

Using the general procedure for the reduction of the substituted 2-nitrobenzylalcohol the desired compound was obtained as a brown solid, 162 mg, 79% yield.

R.f 0.45 (EtOAc),
m.p. 118-121° C.,
LCMS: $t_r$=0.93 min (95% MeOH in water), m/z M+H 137.80,
HPLC: $t_r$=1.53 min (90% ACN in $H_2O$), 96%,
$^1$H NMR (CDCl$_3$, 270 MHz,): δ 2.22 (3H, s, CH$_3$), 4.02 (2H, br.s, NH), 4.64 (2H, s, CH$_2$), 6.62 (1H, d, J=9.3 Hz, ArH), 6.89-6.95 (2H, m, ArH), 7.25 (1H, s, OH).

Synthesis of N-(2-hydroxymethyl-4-methyl-phenyl)-acetamide, $C_{10}H_{13}NO_2$, MW 179.22

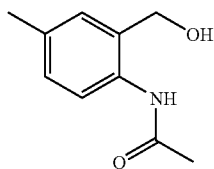

Using the general procedure for the acylation of substituted 2-aminobenzylalcohols the title compound was obtained as a cream solid, 180 mg, 79% yield.

R.f 0.35 (EtOAc),
m.p. 134-136° C.,
$^1$H NMR (CDCl$_3$, 270 MHz): δ 2.17 (3H, s, CH$_3$), 2.29 (3H, s, CH$_3$), 4.63 (2H, d, J=4.9 Hz, CH$_2$), 7.02 (1H, s, ArH), 7.12 (1H, d, J=8.4 Hz, ArH), 7.80 (1H, d, J=8.2 Hz, ArH), 8.28 (1H, s, NH).

Synthesis of N-(2-formyl-4-methyl-phenyl)-acetamide, $C_{10}H_{11}NO_2$, MW 177.20

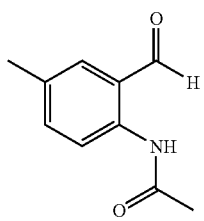

Using the general procedure for the Dess-Martin Periodinane oxidation of alcohols the title compound was obtained as a red oil, 44 mg, 25% yield.

R.f 0.8 (10% MeOH in DCM),
$^1$H NMR (CDCl$_3$, 270 MHz): δ 2.21 (3H, s, CH$_3$), 2.36 (3H, s, CH$_3$), 7.37-7.41 (2H, m, ArH), 8.55-8.61 (1H, m, ArH), 9.84 (1H, s, CHO), 10.98 (1H, br.s, NH).

Synthesis of N-(2-[2-(4-chloro-phenoxy)-phenylamino]-methyl-4-methyl-phenyl)-acetamide, $C_{22}H_{21}ClN_2O_2$, MW 380.87

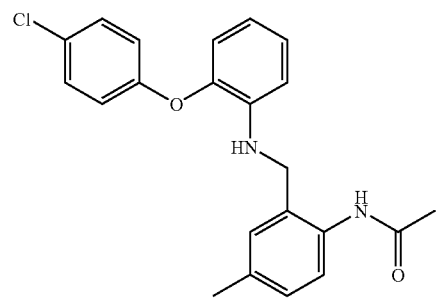 [SMILES: CC(=O)Nc1ccc(C)cc1CNc1ccccc1Oc1ccc(Cl)cc1]

Using the general procedure for the reductive amination of the substituted diphenylether aniline with the substituted 2-acetamide benzaldehyde the desired compound was isolated as a light cream solid, 37 mg, 47% yield.

R.f 0.35 (EtOAc),
m.p. 138-140° C.,
LCMS: $t_r$=1.21 min (95% MeOH in water), m/z M+H 381.20,
HPLC: $t_r$=2.38 min (90% ACN in $H_2O$), 96%,
$^1$H NMR (CDCl$_3$, 270 MHz): δ 1.97 (3H, s, CH$_3$), 2.29 (3H, s, CH$_3$), 4.25 (3H, s, CH$_2$ and NH), 6.76-6.93 (5H, m, ArCH), 7.07-7.13 (3H, m, ArH), 7.22-7.27 (2H, m, ArH), 7.83 (1H, d, J=8.2 Hz, ArH), 8.35 (1H, br.s, NH).
$^{13}$C NMR (CDCl$_3$, 68 MHz): δ 20.9, 24.5 (CH$_3$), 47.5 (CH$_2$), 113.6, 118.6, 119.3, 119.6, 123.1, 125.5 (ArCH), 128.0, 128.1 (ArC), 129.3, 129.9, 130.2 (ArCH), 134.4, 134.7, 139.9, 143.8, 156.0 (ArC), 168.5 (CO).
HRMS: Calcd for $C_{22}H_{21}ClN_2O_2$ (M+H)$^+$ 381.1364. found (M+H)$^+$ 381.1365.

Synthesis of N-(4-chloro-2-hydroxymethyl-phenyl)-acetamide, $C_9H_{10}ClNO_2$, MW 199.63

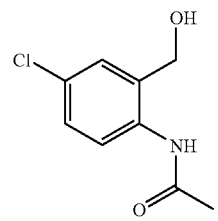

Using the general procedure for the acylation of substituted 2-aminobenzylalcohols the title compound was obtained as a cream waxy solid, 1.12 g, 89% yield.

R.f 0.35 (EtOAc), $^1$H NMR (CDCl$_3$, 270 MHz): δ 1.46 (2H, s, NH and OH), 2.19 (3H, s, CH$_3$), 4.60 (2H, s, CH$_2$), 7.14-7.26 (2H, m, ArH), 7.94-7.98 (1H, m, ArH).

Synthesis of N-(4-chloro-2-formyl-phenyl)-acetamide, C$_9$H$_8$ClNO$_2$, MW 197.62

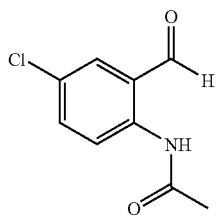

Using the general procedure for the Dess-Martin Periodinane oxidation of alcohols the title compound was obtained as a red solid, 383 mg, 70% yield.

R.f 0.72 (10% MeOH in EtOAc), m.p. 152-154° C., $^1$H NMR (CDCl$_3$, 270 MHz): δ 2.24 (3H, s, CH$_3$), 7.55 (1H, dd, J=2.5, 8.9 Hz, ArH), 7.61 (1H, dd, J=2.5 Hz, ArH), 8.71 (1H, d, J=9.2 Hz, ArH), 9.84 (1H, s, CHO), 11.00 (1H, br.s, NH).

Synthesis of N-(4-chloro-2-[2-(4-chloro-phenoxy)-phenylamino]-methyl-phenyl)-acetamide, C$_{21}$H$_{18}$Cl$_2$N$_2$O$_2$, MW 401.29

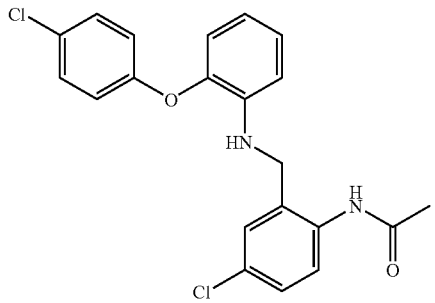 [SMILES: CC(=O)Nc1ccc(Cl)cc1CNc1ccccc1Oc1ccc(Cl)cc1]

Using the general procedure for the reductive amination of the substituted diphenylether aniline with the substituted 2-acetamide benzaldehyde the desired compound was isolated as a light brown waxy solid, 68 mg, 26% yield.

R.f 0.43 (1:1, EtOAc:Hexane),

LCMS: t$_r$=1.21 min (95% MeOH in water), m/z M−H 399.15, 401.1,

HPLC: t$_r$=2.62 min (90% ACN in H$_2$O), 97%, $^1$H NMR (CDCl$_3$, 270 MHz): δ 1.95 (3H, s, NH and CH$_2$), 4.22 (3H, s, NH and CH$_2$), 6.79-6.91 (5H, m, ArH), 7.07-7.13 (1H, m, ArH), 7.24-7.28 (4H, m, ArH), 7.98 (1H, d, J=8.4 Hz, ArH), 8.56 (1H, br.s, NHCO), $^{13}$C NMR (CDCl$_3$, 101 MHz): δ 24.5 (CH$_3$), 47.5 (CH$_2$), 113.8, 118.7, 119.5, 119.9, 124.1, 125.5, 128.7, 129.3 (ArCH), 129.5 (ArC), 129.9 (ArCH), 136.0, 139.4, 144.1, 155.9, 168.5, 200.5 (ArC), 205.1 (CO).

HRMS: Calcd for C$_{21}$H$_{18}$Cl$_2$N$_2$O$_2$ (M+H)$^+$ 401.0818. found (M+H)$^+$ 401.0803.

Synthesis of N-(4-chloro-2-[2-(2,4-dichloro-phenoxy)-phenylamino]-methyl-phenyl)-acetamide, C$_{21}$H$_{17}$Cl$_3$N$_2$O$_2$, MW 435.73

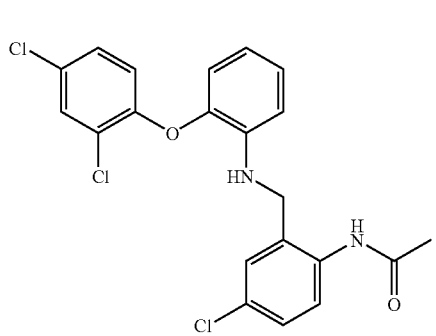 [SMILES: CC(=O)Nc1ccc(Cl)cc1CNc1ccccc1Oc1ccc(Cl)cc1Cl]

2-(2,4-Dichloro-phenoxy)-phenylamine hydrochloride (350 mg, 1.22 mmol) was dissolved in DCM (10 ml) and to this was added K$_2$CO$_3$ (335 mg, 2.44 mmol), the reaction was then stirred at r.t. for 30 min. H$_2$O was then added and the mixture was extracted with DCM. The organic layers were combined, dried (MgSO$_4$), filtered and evaporated in vacuo. The resulting amine was dissolved in DCE (2 ml) and to this was added N-(4-chloro-2-formyl-phenyl)-acetamide (160 mg, 0.81 mmol), acetic acid (0.15 ml) and sodium triacetoxyborohydride (0.43 g, 2.02 mmol). The resulting reaction mixture was stirred at r.t. for 2 h. NaHCO$_3$ was then added and the mixture was repeatedly extracted with DCM. The organic layers were combined, dried (MgSO$_4$), filtered and evaporated in vacuo. The crude mixture was purified using flash chromatography (0-50% EtOAc in hexane) to afford the title compound as a cream solid, 210 mg, 60% yield.

R.f 0.38 (EtOAc), m.p. 135-137° C.,

LCMS: t$_r$=1.3 min (95% MeOH in water), m/z M−H 433.1, 435.1,

HPLC: t$_r$=2.8 min (90% ACN in H$_2$O), 99%, $^1$H NMR (CDCl$_3$, 270 MHz): δ 1.98 (3H, s, CH$_3$), 4.28-4.29 (2H, m, CH$_2$), 4.40 (1H, br.s, NH), 6.70-6.88 (4H, m, ArH), 7.04-7.10 (1H, m, ArH), 7.17 (1H, dd, J=2.5 Hz, ArH), 7.25-7.27 (2H, m, ArH), 7.45 (1H, d, J=2.5 Hz, ArH), 7.96-7.99 (1H, m, ArCH), 8.64 (1H, br.s. NH), $^{13}$C NMR (CDCl$_3$, 101 MHz): δ 24.6 (CH$_3$), 47.4 (CH$_2$), 113.8, 117.8, 119.7, 120.3, 124.1, 125.3 (ArCH), 125.9 (ArC), 128.2, 128.7, 129.3 (ArCH), 129.4 (ArC), 129.6 (ArC), 130.7 (ArCH), 136.0, 138.6, 144.4, 151.1 (ArC), 168.5 (CO).

HRMS: Calcd for C$_{21}$H$_{17}$Cl$_3$N$_2$O$_2$ (M+H)$^+$ 435.0428. found (M+H)$^+$ 437.0387.

Synthesis of N-(4-chloro-2-[2-(4-trifluoromethoxy-phenoxy)-phenylamino]-methyl-phenyl)-acetamide, C$_{22}$H$_{18}$ClF$_3$N$_2$O$_3$, MW 450.84

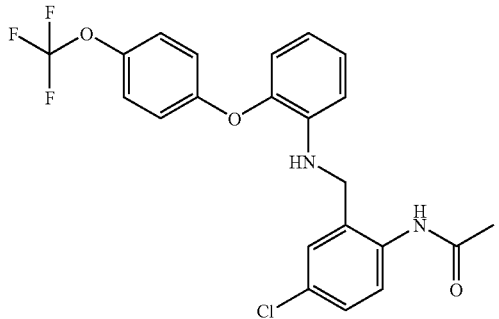 [SMILES: CC(=O)Nc1ccc(Cl)cc1CNc1ccccc1Oc1ccc(OC(F)(F)F)cc1]

Using the general procedure for the reductive amination of the substituted diphenylether aniline with the substituted 2-acetamide benzaldehyde the desired compound was isolated as a brown solid, 86 mg, 30% yield.

R.f 0.35 (1:1, EtOAc:Hexane),
m.p. 121-123° C.,
LCMS: t$_r$=1.07 min (95% MeOH in water), m/z M−H 449.29,
HPLC: t$_r$=3.28 min (90% ACN in H$_2$O), >99%,
$^1$H NMR (CDCl$_3$, 270 MHz): δ 1.94 (3H, s, CH$_3$), 4.23 (3H, s, CH$_2$ and NH), 6.80-6.96 (5H, m, ArH), 7.08-7.18 (3H, m, ArH), 7.25-7.30 (3H, m, ArH), 7.99 (1H, dd, J=8.4 Hz, ArH), 8.54 (1H, br.s, NHCO).
$^{13}$C NMR (CDCl$_3$, 101 MHz): 24.4 (CH$_3$), 47.4 (CH$_2$), 113.8, 118.1, 119.6, 119.8, 112.8, 123.9, 125.5, 128.6, 129.2 (ArCH), 135.9, 139.3 (ArC), 155.6 (OCF$_3$), 207.9 (CO).
$^{19}$F NMR (CDCl$_3$, 376 MHz): δ −58.3 (OCF$_3$)
Anal. Calcd for C$_{22}$H$_{18}$ClF$_3$N$_2$O$_3$: C, 58.61; H, 4.02; N, 6.21%. Found: C, 58.1; H, 4.12; N, 5.96%,
HRMS: Calcd for C$_{22}$H$_{18}$ClF$_3$N$_2$O$_3$ (M+H)$^+$ 451.1031. found (M+H)$^+$ 451.1024.

Synthesis of N-[2-(4-chloro-phenoxy)-phenyl]-2-nitro-benzamide, C$_{19}$H$_{13}$ClN$_2$O$_4$, MW 368.77

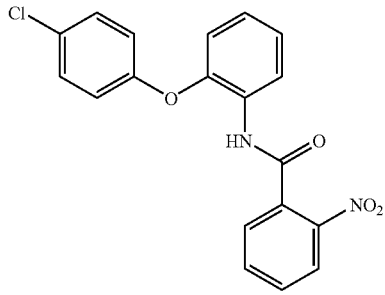

To a solution of 2-(4-chloro-phenoxy)-phenylamine (200 mg, 0.91 mmol) in DCM (5 ml) at 0° C. was added 2-nitrobenzoyl chloride (338 mg, 1.82 mmol) and TEA (0.15 ml). The reaction was then stirred at r.t. for 30 min. NaHCO$_3$ was added and the mixture was extracted with DCM, dried (MgSO$_4$) and purified by flash chromatography (0-100% DCM in hexane) to yield the desired product, 258 mg, 77% yield.

LCMS: t$_r$=1.91 min (80% MeOH in water), m/z M−H 367.09,
HPLC: t$_r$=2.16 min (90% ACN in water), 90%,
$^1$H NMR (CDCl$_3$, 270 MHz): δ 6.83 (1H, dd, J=1.4, 8.0 Hz, ArH), 6.91-6.99 (2H, m, ArH), 7.07 (1H, td, J=1.6, 8.0 Hz, ArH), 7.17 (1H, t, J=7.2 Hz, ArH), 7.24-7.31 (2H, m, ArH), 7.48 (1H, dd, J=1.4, 7.2 Hz, ArH), 7.58 (1H, td, J=1.4, 7.5 Hz, ArH), 7.65 (1H, dd, J=1.1, 7.4 Hz, ArH), 8.00-8.06 (2H, m, ArH and NH), 8.47 (1H, dd, J=1.1, 8.0 Hz, ArH).

Synthesis of 2-amino-N-[2-(4-chloro-phenoxy)-phenyl]-benzamide, C$_{19}$H$_{15}$ClN$_2$O$_2$, MW 338.79

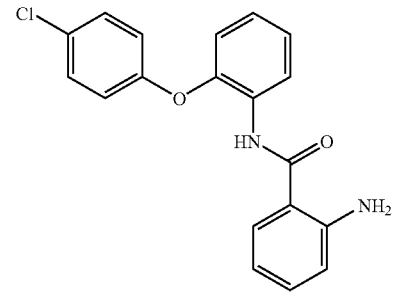 [SMILES: O=C(Nc1ccccc1Oc1ccc(Cl)cc1)c1ccccc1[N+](=O)[O-]]

Using the general procedure for the reduction of the substituted 2-nitrobenzylalcohol the desired product was obtained as a white waxy solid, 143 mg, 62% yield.

R.f 0.39 (DCM),
LCMS: t$_r$=2.67 min (80% MeOH in water), m/z M−H 337.05,
HPLC: t$_r$=2.59 min (90% ACN in water), 98%,
$^1$H NMR (CDCl$_3$, 270 MHz): δ 5.55 (2H, br.s., NH$_2$), 6.62-6.70 (2H, m, ArH), 6.87 (1H, dd, J=1.4, 8.0 Hz, ArH), 6.96-6.99 (2H, m, ArH), 7.04 (1H, td, J=1.4, 7.5 Hz, ArH), 7.15-7.25 (2H, m, ArH), 7.39-7.34 (3H, m, ArH), 8.34 (1H, br.s, NH), 8.50 (1H, dd, J=1.4, 8.0 Hz, ArH).

Synthesis of 2-acetylamino-N-[2-(4-chloro-phenoxy)-phenyl]-benzamide, C$_{21}$H$_{17}$ClN$_2$O$_3$, MW 380.82

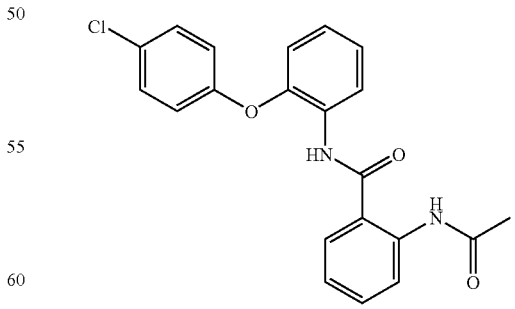

2-Amino-N-[2-(4-chloro-phenoxy)-phenyl]-benzamide (120 mg, 0.36 mmol) was dissolved in DCM (3 ml) and cooled to 0° C., to this was added acetyl chloride (0.05 ml, 0.72 mmol) and TEA (0.07 ml, 1.1 mmol). The resulting solution was stirred at r.t. for 1 h, NaHCO$_3$ was then added and the mixture extracted repeatedly with DCM. The organic portions were then washed with HCl (1M) and dried (MgSO$_4$). The crude mixture was then purified by flash chromatography (0-50% EtOAc in DCM) to yield the desired product as a white solid, 65 mg, 48% yield.

R.f 0.46 (25% EtOAc in DCM),
m.p. 158-160° C.,
LCMS: t$_r$=1.05 min (95% MeOH in water), m/z M−H 379.00,
HPLC: t$_r$=2.48 min (90% ACN in water), 99%,
$^1$H NMR (CDCl$_3$, 270 MHz): δ 2.2 (3H, s, CH$_3$), 6.87 (1H, dd, J=1.6, 8.3 Hz, ArH), 6.96-7.01 (2H, m, ArH), 7.05-7.13 (2H, m, ArH), 7.19 (1H, td, J=1.6, 7.7 Hz, ArH), 7.29-7.34 (2H, m, ArH), 7.45-7.52 (2H, m, ArH), 8.40-8.44 (2H, m, ArH and NH), 8.58 (1H, d, J=15.7 Hz, ArH).
$^{13}$C NMR (CDCl$_3$, 68 MHz): 28.0 (CH$_3$), 117.7, 120.3 (ArCH), 121.0 (ArC), 121.5, 121.9, 123.1, 124.4, 125.2, 126.6 (ArCH), 128.9, 129.6 (ArC), 130.2, 133.2 (ArCH), 139.9, 146.4, 154.6 (ArC), 167.3, 169.1 (CO).
HRMS: Calcd for C$_{21}$H$_{17}$ClN$_2$O$_3$ (M+H)$^+$ 381.1000. found (M+H)$^+$ 381.0994.

Synthesis of 2-benzoylamino-N-[2-(4-chloro- phenoxy)-phenyl]-benzamide, C$_{26}$H$_{19}$ClN$_2$O$_3$, MW 442.89

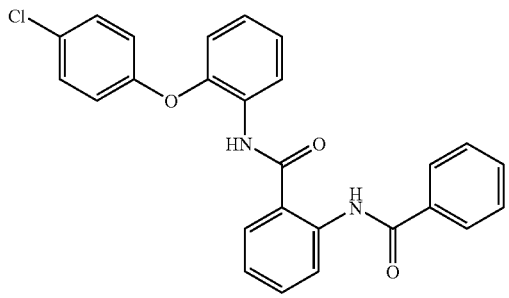 [SMILES: O=C(Nc1ccccc1C(=O)Nc1ccccc1Oc1ccc(Cl)cc1)c1ccccc1]

2-Amino-N-[2-(4-chloro-phenoxy)-phenyl]-benzamide (120 mg, 0.36 mmol) was dissolved in DCM (3 ml) and cooled to 0° C., to this was added benzoyl chloride (0.08 ml, 0.72 mmol) and TEA (0.07 ml, 1.1 mmol). The resulting solution was stirred at r.t. for 1 h and NaHCO$_3$ was then added and the mixture was repeatedly extracted with DCM. This was then washed with HCl (1M) and dried (MgSO$_4$). The crude mixture was then purified by flash chromatography (0-100% DCM in hexane) to yield the desired product as a white solid, 60 mg, 38% yield.

R.f 0.46 (DCM),
m.p. 183-185° C.,
LCMS: t$_r$=1.29 min (95% MeOH in water), m/z M−H 440.97,
HPLC: t$_r$=3.89 min (90% ACN in water), >99%,
$^1$H NMR (CDCl$_3$, 270 MHz): δ 6.88 (1H, d, J=7.6 Hz, ArH), 6.99 (2H, d, J=2.0 Hz, ArH), 7.08-7.15 (2H, m, ArH), 7.21 (1H, t, J=7.2 Hz, ArH), 7.31 (2H, dd, J=0.8, 6.8 Hz, ArH), 7.50-7.59 (5H, m, ArH and NH), 8.04 (2H, dd, J=1.2, 4.8 Hz, ArH), 8.49-8.51 (2H, m, ArH), 8.83 (1H, d, J=8.0 Hz, ArH), 11.89 (1H, br.s, NH).
$^{13}$C NMR (CDCl$_3$, 68 MHz): δ 117.6, 120.2 (ArCH), 128.8 (ArC), 121.6, 121.9, 123.1, 124.3, 125.1, 127.4, 128.8 (ArCH), 128.9, 129.4 (ArC), 130.1, 131.9, 133.3 (ArCH), 134.7, 140.3, 146.3, 154.6 (ArC), 165.6, 167.3 (CO).

HRMS: Calcd for C$_{26}$H$_{19}$ClN$_2$O$_3$ (M+H)$^+$ 443.1157. found (M+H)$^+$ 443.1162.

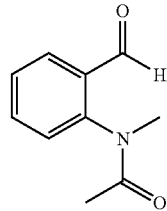

Synthesis of N-(2-formyl-phenyl)-N-methyl-acetamide, C$_{10}$H$_{11}$NO$_2$, MW 177.20

To a solution of N-(2-formyl-phenyl)- acetamide (100 mg, 0.61 mmol) in DMF (10 ml) was added NaH (60% dispersion in mineral oil, 30 mg, 0.73 mmol). After 1 h had elapsed MeI (0.08 ml, 1.2 mmol) was added and this was then stirred at r.t. under N$_2$ for 3 days. This was poured onto water (20 ml), extracted with EtOAc and dried (MgSO$_4$). The crude product was purified by flash chromatography (0-100% DCM in hexane) to yield the desired product, 60 mg, 56% yield.

R.f 0.35 (DCM),
LCMS: t$_r$=1.0 min (95% MeOH in water), m/z M+H 177.80,
HPLC: t$_r$=1.0 min (95% MeOH in water), 97%,
$^1$H NMR (CDCl$_3$, 270 MHz): δ 1.79 (3H, s, CH$_3$CO), 3.28 (3H, s, CH$_3$N), 7.26-7.29 (1H, m, ArH), 7.50-7.55 (1H, m, ArH), 7.69 (1H, td, J=1.6, 7.5 Hz, ArH), 7.97 (1H, J=1.6, 7.7 Hz, ArH), 10.13 (1H, s, CHO).

Synthesis of N-(2-([2-(4-chloro-phenoxy)-phenylamino]-methyl)-phenyl)-N-methyl-acetamide, C$_{22}$H$_{21}$ClN$_2$O$_2$, MW 380.87

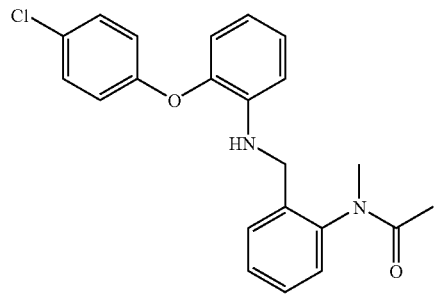 [SMILES: CC(=O)N(C)c1ccccc1CNc1ccccc1Oc1ccc(Cl)cc1]

To a solution of 2-(4-chloro-phenoxy)-phenylamine (174 mg, 0.78 mmol) and N-(2-formyl-phenyl)-N-methyl-acetamide (70 mg, 0.39 mmol) in DCE (2 ml) was added NaHB(OAc)$_3$ (210 mg, 0.98 mmol) and AcOH (0.07 ml). The resulting solution was stirred at r.t. for 2 h. NaHCO$_3$ was then added and the mixture was extracted with DCM and dried (MgSO$_4$). The crude product was purified by flash chromatography (0-100% DCM in hexane) to yield the desired product as a brown oil, 65 mg, 44% yield.

R.f 0.51 (DCM),
LCMS: t$_r$=1.19 min (95% MeOH in water), m/z M−H 378.93,
HPLC: t$_r$=2.64 min (90% ACN in water), 98%, ¹H NMR (CDCl₃, 270 MHz): δ 1.78 (3H, s, CH₃CO), 3.24 (3H, s, CH₃N), 4.25-4.29 (2H, m, CH₂), 6.59 (1H, dd, J=1.4, 8.0 Hz, ArH), 6.67 (1H, td, J=1.4, 7.7 Hz, ArH), 6.83 (1H, dd, J=1.4, 7.7 Hz, ArH), 6.88-6.92 (2H, m, ArH), 7.00 (1H, td, J=1.6, 7.7 Hz, ArH), 7.11-7.17 (1H, m, ArH), 7.23-7.26 (2H, m, ArH), 7.31-7.34 (2H, m, ArH), 7.41-7.44 (1H, m, ArH).

¹³C NMR (CDCl₃, 68 MHz): 26.5, 36.6 (CH₃), 43.7 (CH₂), 117.7, 118.7, 119.5, 125.4 (ArCH), 127.9 (ArC), 128.5, 128.9, 129.1, 129.7 (ArCH), 136.3, 139.9, 142.5, 142.8, 156.1 (ArC), 170.8 (CO).

HRMS: Calcd for C₂₂H₂₁ClN₂O₂ (M+H)⁺ 381.1364. found (M+H)⁺ 381.1378.

Synthesis of N-[2-(([2-(4-chloro-phenoxy)-phenyl]-methyl-amino)-methyl)-phenyl]-N-methyl-acetamide, C₂₃H₂₃ClN₂O₂, MW 394.89

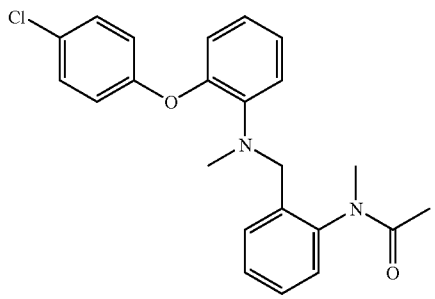 [SMILES: CC(=O)N(C)c1ccccc1CN(C)c1ccccc1Oc1ccc(Cl)cc1]

N-(2-([2-(4-chloro-phenoxy)-phenylamino]-methyl)-phenyl)-acetamide, (100 mg, 0.27 mmol) in DMF (10 ml) was cooled to 0° C., to this was added NaH (35 mg, 0.81 mmol) and the resulting solution was stirred for 1 h. MeI (0.05 ml, 0.81 mmol) was then added and the solution stirred for a further 18 h. The reaction mixture was then poured onto water, extracted with EtOAc and dried (MgSO₄). NMR analysis showed the crude product to be a mixture of product and the related mono-methylated compound. Preparative-HPLC was used for purification to yield the desired product, 25 mg, 23% yield. Please note N-(2-([2-(4-chloro-phenoxy)-phenylamino]-methyl)-phenyl)-N-methyl-acetamide was also isolated, 46 mg, 43% yield.

R.f 0.45 (EtOAc),

LCMS: t_r=5.6 min (80% MeOH in water), m/z M+H 395.18,

HPLC: t_r=3.75 min (90% ACN in water), 98%,

¹H NMR (CDCl₃, 270 MHz): δ 1.70 (3H, s, CH₃), 2.66 (3H, s, NCH₃), 3.09 (3H, s, NCH₃), 4.10 (2H, s, CH₂), 6.67-6.73 (2H, m, ArH), 6.96 (2H, d, J=3.9 Hz, ArH), 7.04-7.27 (8H, m, ArH).

¹³C NMR (CDCl₃, 68 MHz): δ 22.0, 36.3, 39.7 (CH₃), 54.9 (CH₂), 117.8, 119.7, 122.2, 122.5, 125.6 (ArCH), 127.1 (ArC), 142.4, 145.0, 147.4 (ArC), 170.8 (CO).

HRMS: Calcd for C₂₃H₂₃ClN₂O₂ (M+H)⁺ 395.1521. found (M+H)⁺ 395.1533.

Synthesis of N-[2-(([2-(4-chloro-phenoxy)-phenyl]-methyl-amino)-methyl)-phenyl]-acetamide, C₂₂H₂₁ClN₂O₂, MW 380.87

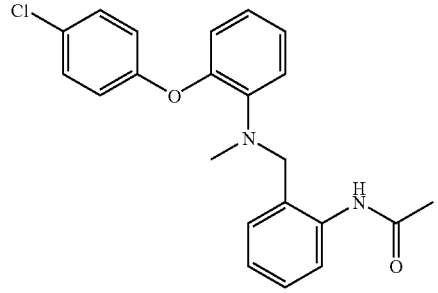 [SMILES: CC(=O)Nc1ccccc1CN(C)c1ccccc1Oc1ccc(Cl)cc1]

To a solution of N-(2-[2-(4-chloro-phenoxy)-phenylamino]-methyl-phenyl)-acetamide, (100 mg, 0.27 mmol), paraformaldehyde (81 mg, 2.7 mmol) and NaBH₄ (55 mg, 1.35 mmol) in THF (5 ml) was added TFA (1.3 ml). The resulting solution was stirred at r.t. for 18 h. This was then poured into NaOH solution (25%) with ice chips, extracted with DCM and dried (MgSO₄). The crude product was then purified by flash chromatography (0-100% EtOAc in hexane) to produce the desired compound as a colourless oil, 64 mg, 62% yield.

R.f 0.66 (EtOAc),

LCMS: t_r=4.02 min (80% MeOH in water), m/z M+H 379.12,

HPLC: t_r=2.88 min (90% MeOH in water), 99%,

¹H NMR (CDCl₃, 270 MHz,): δ 1.99 (3H, s, CH₃), 2.65 (3H, s, CH₃N), 4.19 (2H, s, CH₂), 6.81 (1H, dd, J=1.6, 8.4 Hz, ArH), 6.93-6.95 (2H, m, ArH), 6.99-7.04 (2H, m, ArH), 7.10 (1H, td, J=1.6, 8.0 Hz, ArH), 7.14-7.15 (1H, m, ArH), 7.23-7.32 (4H, m, ArH), 8.27 (1H, d, J=8.4 Hz, ArH), 10.12 (1H, br.s, NHCO),

¹³C NMR (CDCl₃, 101 MHz): 24.8, 40.7 (CH₃), 59.5 (CH₂), 118.7, 120.3, 120.9, 121.3, 123.2, 124.1, 124.6 (ArCH), 125.1 (ArC), 128.6 (ArCH), 129.0 (ArC), 130.1 (ArCH), 138.6, 142.4, 150.8, 155.1 (ArC), 168.6 (CO).

HRMS: Calcd for C₂₂H₂₁ClN₂O₂ (M+H)⁺ 381.1364. found (M+H)⁺ 381.1363.

Synthesis of N-(2-Acetylamino-benzyl)-N-[2-(4-chloro-phenoxy)-phenyl]-acetamide, C₂₃H₂₁ClN₂O₃, MW 408.88

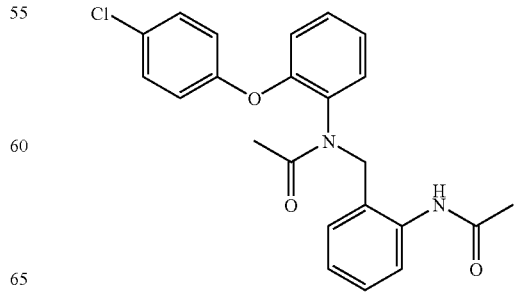

A solution of N-(2-[2-(4-chloro-phenoxy)-phenylamino]-methyl-phenyl)-acetamide (100 mg, 0.27 mmol) in DCM (5 ml) and cooled to 0° C., to this was added TEA (0.2 ml) and acetyl chloride (0.34 ml, 0.81 mmol) the resulting solution was stirred at r.t. for 1 h. Saturated NaHCO$_3$ was added, extracted with DCM and dried (MgSO$_4$). The crude product was purified by flash chromatography (0-100% EtOAc in hexane) and preparative HPLC to yield the desired product as an off white waxy solid, 53 mg, 48% yield.

R.f 0.54 (EtOAc),

LCMS: t$_r$=2.17 min (95% MeOH in water), m/z M−H 407.15,

HPLC: t$_r$=2.40 min (90% ACN in water), 95%, $^1$H NMR (CDCl$_3$, 270 MHz): δ 1.93 (3H, s, CH$_3$), 2.24 (3H, s, CH$_3$), 4.80 (2H, s, CH$_2$), 7.02-7.12 (2H, m, ArH), 7.21-7.30 (4H, m, ArH), 8.20 (1H, dd, J=7.7 Hz, ArH), 9.89 (1H, s, NHCO).

$^{13}$C NMR (CDCl$_3$, 68 MHz): 22.1, 24.6 (CH$_3$), 49.8 (CH$_2$), 118.1, 120.7, 122.1, 123.0, 124.0 (ArCH), 125.0 (ArC), 129.2 (ArCH), 129.8 (ArC), 130.1, 130.2, 131.5 (ArCH), 137.7, 153.2, 153.8 (ArC), 169.5, 172.7 (CO).

HRMS: Calcd for C$_{23}$H$_{21}$ClN$_2$O$_3$ (M+H)$^+$ 409.1313. found (M+Na)$^+$ 431.1105.

Synthesis of N-(4-([2-(4-chloro-phenoxy)- phenylamino]-methyl)-phenyl)-acetamide, C$_{21}$H$_{19}$ClN$_2$O$_2$, MW 366.84

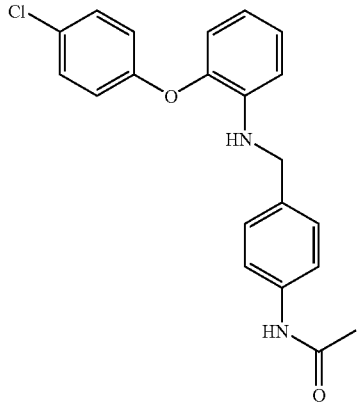 [SMILES: CC(=O)Nc1ccc(CNc2ccccc2Oc2ccc(Cl)cc2)cc1]

Using the general procedure for the reductive amination of the substituted diphenylether aniline with the substituted 2-acetamide benzaldehyde the desired compound was isolated as a light pink solid, 195 mg, 78% yield.

R.f 0.55 (5% MeOH in DCM), m.p. 137-139° C.,

LCMS: t$_r$=1.39 min (95% MeOH in H$_2$O), m/z M−H 365.48,

HPLC: t$_r$=2.0 min (90% ACN in H$_2$O), 98%, $^1$H NMR (CDCl$_3$, 270 MHz): δ 2.15 (3H, s, CH$_3$), 4.30 (2H, d, J=5.7 Hz, CH$_2$), 6.60-6.69 (2H, m, ArH), 6.82 (1H, dd, J=1.5, 7.7 Hz, ArH), 6.86-6.91 (2H, m, ArH), 6.96-7.02 (1H, m, ArH), 7.12 (1H, s, NH), 7.21-7.26 (4H, m, ArH), 7.41-7.44 (2H, m, ArH).

$^{13}$C NMR (CDCl$_3$, 101 MHz): δ 24.6 (CH$_3$), 47.2 (CH$_2$), 111.9, 117.1, 118.5, 119.3, 120.1, 125.3 (ArCH), 127.6 (ArC), 127.9, 129.6 (ArCH), 135.1, 136.8, 140.1, 142.6, 156.2 (ArC), 168.2 (CO).

HRMS: Calcd for C$_{21}$H$_{19}$ClN$_2$O$_2$ (M+Na)$^+$ 389.1025. found (M+Na)$^+$ 389.1028.

Anal. calcd for C$_{21}$H$_{19}$ClN$_2$O$_2$: C, 68.76; H, 5.22; N, 7.64%. Found: C, 68.5; H, 5.26; N, 7.61%.

Synthesis of N-(4-([2-(2,4-dichloro-phenoxy)- phenylamino]-methyl)-phenyl)-acetamide, C$_{21}$H$_{18}$Cl$_2$N$_2$O$_2$, MW 401.29

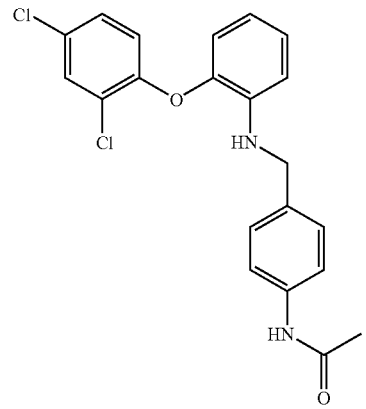 [SMILES: CC(=O)Nc1ccc(CNc2ccccc2Oc2ccc(Cl)cc2Cl)cc1]

To a solution of 2-(2,4-dichloro-phenoxy)-phenylamine hydrochloride (0.15 g, 0.52 mmol) in DCM (10 ml) was added K$_2$CO$_3$ (0.22 g, 1.04 mmol), the resulting solution was stirred at r.t for 30 min. Water was then added and the mixture was extracted with DCM. The organic layers were combined, dried (MgSO$_4$), filtered and evaporated in vacuo. The resulting amine was dissolved in DCE (3 ml) and to this was added 4-acetamidobenzaldehyde (0.126 g, 0.0.75 mmol), acetic acid (0.11 ml) and sodium triacetoxyborohydride (0.27 g, 1.3 mmol). The resulting reaction mixture was stirred at r.t. for 2 h. NaHCO$_3$ was then added and the mixture was repeatedly extracted with DCM. The organic layers were combined, dried (MgSO$_4$), filtered and evaporated in vacuo. The crude mixture was purified using flash chromatography (0-100% EtOAc in hexane) to afford the title compound as a white waxy solid, 142 mg, 69% yield.

R.f 5.8 (EtOAc),

LCMS: t$_r$=1.2 min (95% MeOH in H$_2$O), m/z M−H 399.03, 401.04,

HPLC: t$_r$=2.42 min (90% ACN in H$_2$O), 98%, $^1$H NMR (CDCl$_3$, 270 MHz): δ 2.15 (3H, s, CH$_3$), 4.31 (2H, s, CH$_2$), 4.59 (1H, br.s, NH), 6.59-6.68 (2H, m, ArH), 6.75 (1H, dd, J=1.5, 7.9 Hz, ArH), 6.80 (1H, d, J=8.7 Hz, ArH), 6.96-7.02 (1H, m, ArH), 7.12 (1H, dd, J=2.5, 8.9 Hz, ArH), 7.22-7.31 (1H, m, ArH), 7.41-7.45 (2H, m, ArH).

$^{13}$C NMR (CDCl$_3$, 68 MHz): δ 24.7 (CH$_3$), 47.3 (CH$_2$), 112.2, 117.1, 118.5, 119.4, 120.2, (ArCH), 125.3 (ArC), 125.5, 127.9, 128.0 (ArCH), 128.2 (ArC), 130.4 (ArCH), 135.1, 136.9, 139.7, 142.7, 151.8 (ArC), 168.4 (CO).

HRMS: Calcd for C$_{21}$H$_{18}$Cl$_2$N$_2$O$_2$ (M+H)$^+$ 399.0673. found (M+H)$^+$ 399.0674.

Anal. calcd for C$_{21}$H$_{18}$Cl$_2$N$_2$O$_2$ C, 62.85; H, 4.52; N, 6.98%. Found: C, 62.7; H, 4.52; N, 6.92%.

Synthesis of 3-amino-benzaldehyde, C₇H₇NO, MW 121.14

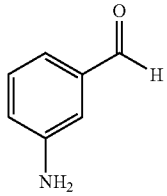

Using the general procedure for the reduction of the substituted 2-nitrobenzylalcohol the desired compound was obtained as a yellow solid, 1.7 g, 71% yield.

R.f 0.25 (DCM),

Further analysis was not carried out and the product was used crude in the following reactions.

Synthesis of N-(3-formyl-phenyl)-acetamide, C₉H₉NO₂, MW 163.17

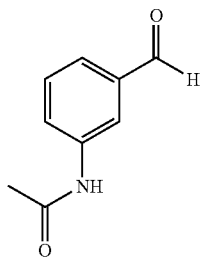

Using the general procedure for the acylation of substituted 2-aminobenzylalcohols the title compound was obtained as a cream oil, 250 mg, 37% yield.

R.f 0.43 (10% MeOH in DCM), $^1$H NMR (CDCl₃, 270 MHz): δ 2.19 (3H, s, CH₃), 7.42 (1H, t, J=7.9 Hz, ArH), 7.56 (1H, d, J=7.7 Hz, ArH), 7.83-7.86 (1H, m, ArH), 8.03 (1H, s, ArH), 8.60 (1H, s, NH), 9.90 (1H, s, CHO).

Synthesis of N-(3-[2-(4-chloro-phenoxy)-phenylamino]-methyl-phenyl)-acetamide, C₂₁H₁₉ClN₂O₂, MW 366.84

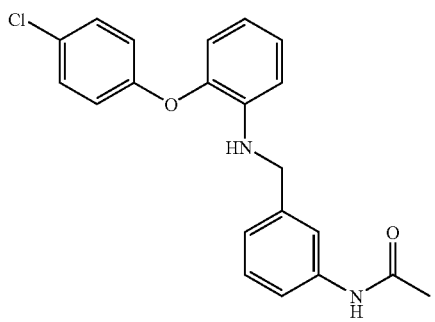 [SMILES: CC(=O)Nc1cccc(CNc2ccccc2Oc2ccc(Cl)cc2)c1]

Using the general procedure for the reductive amination of the substituted diphenylether aniline with the substituted 2-acetamide benzaldehyde the desired compound was isolated as a cream solid, 110 mg, 63% yield.

R.f 0.6 (EtOAc), m.p. 187-190° C.,

LCMS: $t_r$=1.39 min (50% to 95% MeOH in water at 0.5 ml/min to 1.0 ml/min over 5 min), m/z M−H 365.55, HPLC: $t_r$=1.89 min (90% ACN in H₂O), 93%, $^1$H NMR (CDCl₃, 270 MHz): δ 2.13 (3H, s, CH₃), 4.32 (2H, d, J=5.4 Hz, CH₂), 4.55 (1H, d, J=5.4 Hz, NH), 6.61-6.66 (2H, m, ArH), 6.81-6.84 (1H, m, ArH), 6.68-6.92 (2H, m, ArH), 6.98-7.04 (2H, m, ArH), 7.21-7.27 (4H, m, ArH and NH), 7.38-7.43 (2H, m, ArH).

$^{13}$C NMR (CDCl₃, 68 MHz): δ 24.6 (CH₃), 47.5 (CH₂), 112.1, 117.2, 118.4, 118.7, 119.4, 123.0, 125.4 (ArCH), 127.7 (ArC), 129.0, 129.7, 129.9 (ArC), 138.2, 140.1, 140.4, 142.7, 156.3 (ArC), 168.5 (CO).

HRMS: Calcd for C₂₁H₁₉ClN₂O₂ (M+Na)⁺ 389.1027. found (M+Na)⁺ 389.1021.

Synthesis of N-[2-(4-chloro-phenoxy)-phenyl]-N-(2-nitro-benzyl)-acetamide, C₂₁H₁₇ClN₂O₄, MW 396.82

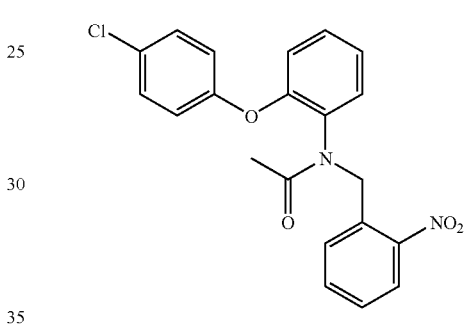

Using the general procedure for the acylation of substituted 2-aminobenzylalcohols the title compound was obtained as a brown oil, 92 mg, 48% yield.

R.f 0.21 (1:1, DCM:hexane),

LCMS: $t_r$=5.12 min (50% to 95% MeOH in water at 0.5 ml/min to 1.0 ml/min over 5 min), m/z M+H 397.48, HPLC: $t_r$=5.0 min (90% ACN in H₂O), 91%, $^1$H NMR (CDCl₃, 270 MHz,): δ 1.98 (3H, s, CH₃), 5.13 (1H, d, J=16.3 Hz, ½CH₂), 5.33 (1H, d, J=16.3 Hz, ½CH₂), 6.79-6.87 (3H, m, ArH), 7.00-7.11 (2H, m, ArH), 7.20-7.35 (4H, m, ArH), 7.46 (1H, td, J=1.5, 7.4 Hz, ArH), 7.72 (1H, dd, J=1.2, 7.9 Hz, ArH), 7.83 (1H, dd, J=1.2, 8.2 Hz, ArH).

Synthesis of N-(2-amino-benzyl)-N-[2-(4-chloro-phenoxy)-phenyl]-acetamide, C₂₁H₁₉ClN₂O₂, MW 366.84

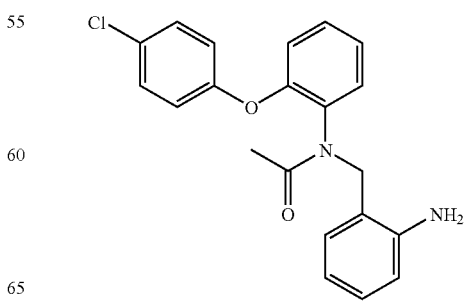

Using the general procedure for the reduction of the substituted 2-nitrobenzylalcohol the desired compound was obtained as a pale yellow solid, 53 mg, 62% yield.

R.f 0.25 (1:1, DCM:EtOAc), $^1$H NMR (CDCl$_3$, 270 MHz): δ 1.92 (3H, s, CH$_3$), 4.55 (2H, br.s, NH$_2$), 4.73-4.87 (2H, m, CH$_2$), 6.38-6.52 (3H, m, ArH), 6.58-6.64 (2H, m, ArH), 6.77 (1H, d, J=8.2 Hz, ArH), 6.96-7.05 (3H, m, ArH), 7.19-7.25 (3H, m, ArH), $^{13}$C NMR (CDCl$_3$, 68 MHz): δ 22.2 (CH$_3$), 49.3 (CH$_2$), 115.41, 116.7, 118.3 (ArCH), 119.8 (ArC), 120.7, 123.8, 129.3, 129.6, 129.9, 130.4, 131.9 (ArCH), 132.1, 146.5, 153.4, 154.4 (ArC), 171.7 (CO).

Synthesis of N-[2-(1-acetyl-piperidin-4-ylamino)-benzyl]-N-[2-(4-chloro-phenoxy)-phenyl]-acetamide, C$_{28}$H$_{30}$ClN$_3$O$_3$, MW 492.01

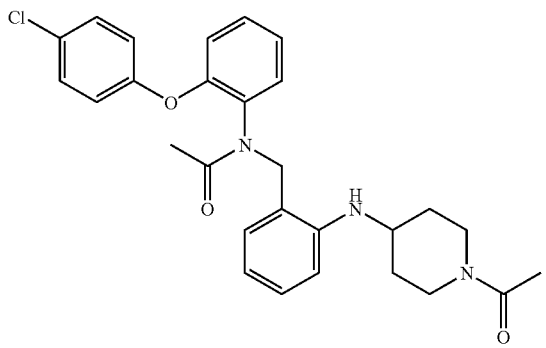 [SMILES: CC(=O)N1CCC(Nc2ccccc2CN(C(C)=O)c2ccccc2Oc2ccc(Cl)cc2)CC1]

Using the general procedure for the reductive amination of the substituted diphenylether aniline with the substituted 2-acetamide benzaldehyde the desired compound was isolated as a cream oil, 45 mg, 63% yield.

R.f 0.72 (10% MeOH in EtOAc),

LCMS: t$_r$=5.4 min (50% to 95% MeOH in water at 0.5 ml/min to 1.0 ml/min over 5 min), m/z

M+H 492.49,

HPLC: t$_r$=6.42 min (90% ACN in H$_2$O), 99%, $^1$H NMR (CDCl$_3$, 400 MHz): δ 1.34-1.51 (1H, m, ½CH$_2$), 1.55-1.66 (1H, m, ½CH$_2$), 1.75-1.79 (1H, m, ½CH$_2$), 1.91, 1.93 (3H, s, CH$_3$), 1.96-2.01 (1H, m, ½CH$_2$), 2.08, 2.09 (3H, s, CH$_3$), 2.91-2.97 (½H, m, ¼CH$_2$), 3.02-3.09 (½H, m, ¼CH$_2$), 3.11-3.18 (½H, m, ¼CH$_2$), 3.21-3.27 (½H, m, ¼CH$_2$), 3.33-3.41 (1H, m, CH), 3.68-3.74 (½H, m, ¼CH$_2$), 3.81-3.86 (½H, m, ¼CH$_2$), 3.99-4.04 (½H, m, ¼CH$_2$), 4.23-4.28 (½H, m, ¼CH$_2$), 4.36 (½H, d, J=14.4 Hz, ¼CH$_2$), 4.65 (½H, d, J=14.8 Hz, ¼CH$_2$), 4.92 (½H, d, J=14.4 Hz, ¼CH$_2$), 5.25 (½H, d, J=14.4 Hz, ¼CH$_2$), 5.58-5.66 (1H, m, NH), 6.30-6.37 (3H, m, ArH), 6.44-6.50 (2H, m, ArH), 6.63-6.66 (½H, m, ArH), 6.72-6.74 (½H, m, ArH), 7.03-7.12 (3H, m, ArH), 7.13-7.16 (1H, m, ArH), 7.17-7.23 (2H, m, ArH).

$^{13}$C NMR (CDCl$_3$, 101 MHz): δ 21.5, 21.5, 22.0 (CH$_3$), 30.6, 31.3, 31.9, 32.3, 39.5, 39.7, 44.7 (CH$_2$), 48.4, 48.7 (CH), 49.5, 49.9 (CH$_2$), 110.1, 110.2, 114.9, 115, 117.8, 118.1, 119.6, 119.7, 120.5, 120.9, 123.7, 123.8, 129.1, 129.1, 129.3, 129.4, 129.6, 129.7, 129.9 (ArCH), 131.6, 131.7 (ArC), 132.1, 132.2 (ArCH), 145.8, 145.9, 153.3, 153.8, 154.0, 154.3 (ArC), 168.7, 168.7, 171.6, 171.7 (CO).

HRMS: Calcd for C$_{28}$H$_{30}$ClN$_3$O$_3$ (M+H)$^+$ 492.2048. found (M+H)$^+$ 492.2049.

Synthesis of [2-(4-chloro-phenoxy)-phenyl]-2-nitro-benzylamine, C$_{19}$H$_{15}$ClN$_2$O$_3$, MW 354.79

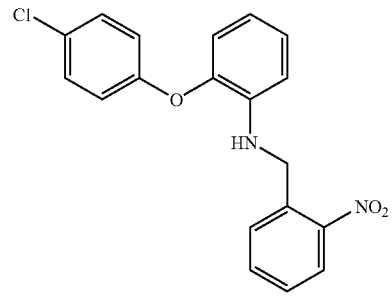 [SMILES: O=[N+]([O-])c1ccccc1CNc1ccccc1Oc1ccc(Cl)cc1]

To a solution of 2-(4-chloro-phenoxy)-phenylamine (150 mg, 0.68 mmol) and 2-nitrobenzaldehyde (310 mg, 2.04 mmol) in DCE (3.5 ml) was added acetic acid (0.36 ml) and sodium triacetoxyborohydride (0.36 g, 1.7 mmol). The resulting reaction mixture was heated in a microwave at 140° C. for 10 min. NaHCO$_3$ was then added and the mixture was repeatedly extracted with EtOAc. The organic layers were combined, dried (MgSO$_4$), filtered and evaporated in vacuo. The crude mixture was purified using flash chromatography (0-100% EtOAc in hexane) to afford the title compound as a yellow solid, 194 mg, 77% yield.

R.f 0.63 (1:1, EtOAc:Hexane),

LCMS: t$_r$=1.66 min (95% MeOH in H$_2$O), m/z M+H 355.48,

HPLC: t$_r$=6.6 min (90% ACN in H$_2$O), 92%, $^1$H NMR (CDCl$_3$, 270 MHz): δ 4.75 (2H, s, CH$_2$), 4.97 (1H, s, NH), 6.52 (1H, dd, J=1.2, 7.9 Hz, ArH), 6.66 (1H, td, J=1.5, 7.7 Hz, ArH), 6.83-6.99 (4H, m, ArH), 7.21-7.27 (2H, m, ArH), 7.37-7.44 (1H, m, ArH), 7.54-7.57 (2H, m, ArH), 8.05 (1H, dd, J=1.0, 7.7 Hz, ArH).

Synthesis of [2-(4-chloro-phenoxy)-phenyl]-(2-amino-benzyl)-amine, C$_{19}$H$_{17}$ClN$_2$O, MW 324.80

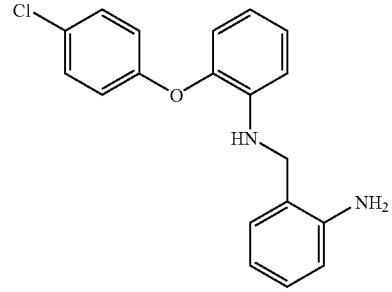

Using the general procedure for the reduction of the substituted 2-nitrobenzylalcohol the desired compound was obtained as a pale yellow solid, 118 mg, >100% yield.

R.f 0.35 (EtOAc), m.p. 178-180° C.,

LCMS: t$_r$=5.51 min (50% to 95% MeOH in water at 0.5 ml/min to 1.0 ml/min over 5 min), m/z M+H 323.4, HPLC: t$_r$=5.95 min (90% ACN in H$_2$O), 85%, $^1$H NMR (CDCl$_3$, 270 MHz,): δ 3.99 (2H, s, NH$_2$), 4.16 (1H, s, NH), 4.23 (2H, s, CH$_2$), 6.66-6.77 (3H, m, ArH), 6.83-6.91 (4H, m, ArH), 7.07-7.16 (3H, m, ArH), 7.20-7.26 (2H, m, ArH).

Synthesis of 1-[4-(2-[2-(4-chloro-phenoxy)-phenylamino]-methyl-phenylamino)-piperidin-1-yl]-ethanone, C$_{26}$H$_{28}$ClN$_3$O$_2$, MW 449.97

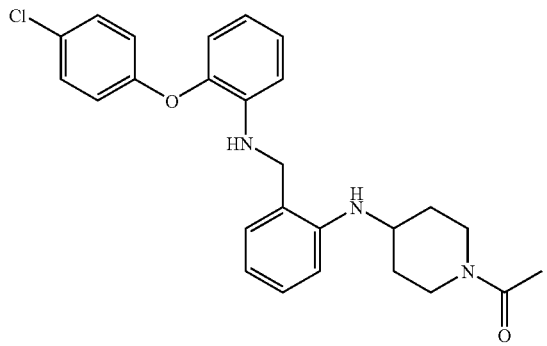 [SMILES: CC(=O)N1CCC(Nc2ccccc2CNc2ccccc2Oc2ccc(Cl)cc2)CC1]

To a solution of [2-(4-chloro-phenoxy)-phenyl]-(2-aminobenzyl)-amine (50 mg, 0.15 mmol) and N-benzoyl-4-piperidone (0.038 ml, 0.30 mmol) in DCE (1.5 ml) was added acetic acid (0.03 ml) and sodium triacetoxyborohydride (82 mg, 0.38 mmol). The resulting reaction mixture was then subjected to microwave heating for 20 min at 140° C. A further portion of sodium triacetoxyborohydride (0.45 g, 0.2 mmol) was added and the solution was subjected to microwave heating for a further 10 min at 140° C. NaHCO$_3$ was then added and the mixture was repeatedly extracted with DCM. The organic layers were combined, dried (MgSO$_4$), filtered and evaporated in vacuo. The crude mixture was purified using flash chromatography (0-10% MeOH in DCM) to afford the title compound as a cream oil, 23 mg, 33% yield.

R.f 0.2 (1:1, EtOAc:Hexane),

LCMS: t$_r$=5.75 min (50% to 95% MeOH in water at 0.5 ml/min to 1.0 ml/min over 5 min), m/z M+Na 472.41, HPLC: t$_r$=6.19 min (90% ACN in H$_2$O), 96%, $^1$H NMR (CDCl$_3$, 400 MHz): δ 1.25 (2H, s, CH$_2$), 1.83-1.92 (2H, m, CH$_2$), 2.07 (3H, s, CH$_3$), 2.98-3.04 (1H, m, ½CH$_2$), 3.11-3.17 (1H, m, ½CH$_2$), 3.47-3.51 (1H, m, ½CH$_2$), 3.56-3.62 (1H, m, ½CH$_2$), 4.09-4.17 (1H, m, NH), 4.21 (2H, td, J=9.6 Hz, CH$_2$NH), 4.70 (1H, s, NH), 6.65-6.71 (2H, m, ArH), 6.75 (1H, td, J=1.6, 7.6 Hz, ArH), 6.81-6.86 (3H, m, ArH), 6.92 (1H, dd, J=1.2, 8.0 Hz, ArH), 7.12 (1H, td, J=1.2, 8.0 Hz, ArH), 7.15-7.17 (1H, m, ArH), 7.19-7.23 (3H, m, ArH).

$^{13}$C NMR (CDCl$_3$, 101 MHz): δ 21.5 (CH$_3$), 29.7, 32.1, 39.7, 44.6 (CH$_2$), 47.5 (CH$_2$NH), 48.7 (CH), 110.9, 112.8, 116.8, 118.4, 119.4 (ArCH), 122.1 (ArC), 125.4 (ArCH), 127.7 (ArC), 129.2, 129.6, 130.4 (ArCH), 140.2, 143.3, 145.9, 156.1 (ArC), 168.8 (CO).

HRMS: Calcd for C$_{26}$H$_{28}$ClN$_3$O$_2$ (M+H)$^+$ 450.1943. found (M+H)$^+$ 450.1943.

Synthesis of 1-acetyl-piperidine-4-carboxylic acid (2-[2-(4-chloro-phenoxy)-phenyl amino]-methyl-phenyl)-amide, C$_{27}$H$_{28}$ClN$_3$O$_3$, MW 477.98

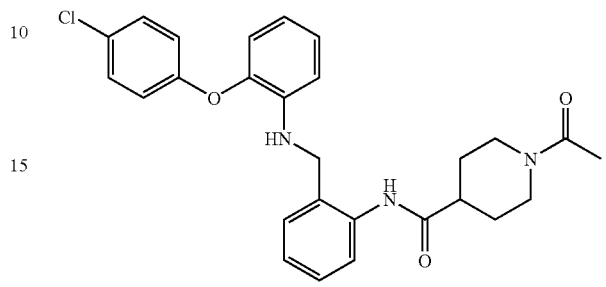

To a solution of [2-(4-chloro-phenoxy)-phenyl]-(2-aminobenzyl)-amine (48 mg, 0.15 mmol) and TEA (0.09 ml) in DCM (6 ml) at 0° C., was added 1-acetylpiperidine-4-carbonyl chloride (58 mg, 0.6 mmol) and the resulting solution stirred was allowed to warm to room temperature and stirred for 24 h. NaHCO$_3$ was then added and the mixture was repeatedly extracted with DCM. The organic portions were then washed with 1M HCl. The organic layers were combined, dried (MgSO$_4$), filtered and evaporated in vacuo. The title compound was obtained as an off white solid, 44 mg, 62% yield.

R.f 0.15 (10% MeOH in DCM), m.p. 140-143° C.,

LCMS: t$_r$=1.25 min (95% MeOH in water), m/z M−H 476.56

HPLC: t$_r$=1.71 min (90% ACN in H$_2$O), 95%, $^1$H NMR (CDCl$_3$, 400 MHz): δ 1.49-1.63 (2H, m, CH$_2$), 1.74-1.83 (2H, m, CH$_2$), 1.99 (3H, s, CH$_3$), 2.18-2.24 (1H, m, CH), 2.49-2.57 (1H, m, CH$_2$), 2.92-2.99 (1H, m, CH$_2$), 3.69-3.73 (1H, m, CH$_2$), 4.28 (3H, s, CH$_2$NH and NH), 4.42-4.46 (1H, m, CH$_2$), 6.77-6.86 (3H, m, ArH), 6.92-6.94 (1H, m, ArH), 7.06-7.10 (2H, m, ArH), 7.22-7.33 (5H, m, ArH), 8.05 (1H, d, J=8.0 Hz, ArH), 8.85 (1H, s, NHCO).

$^{13}$C NMR (CDCl$_3$, 101 MHz): δ 21.4 (CH$_3$), 28.5, 28.7, 40.8 (CH$_2$), 43.8 (CH), 45.6, 47.8 (CH$_2$), 113.5, 118.7, 119.2, 119.7, 122.4, 124.5, 125.3 (ArCH), 127.2, 128.2 (ArC), 128.9, 129.7, 129.8 (ArCH), 137.4, 139.3, 144.0, 155.7 (ArC), 168.7, 172.1 (CO).

HRMS: Calcd for C$_{27}$H$_{28}$ClN$_3$O$_3$ (M+Na)$^+$ 500.1711. found (M+Na)$^+$ 500.1705.

Synthesis of 1-acetyl-piperidine-4-carboxylic acid (3-formyl-phenyl)-amide, C$_{15}$H$_{18}$N$_2$O$_3$, MW 274.32

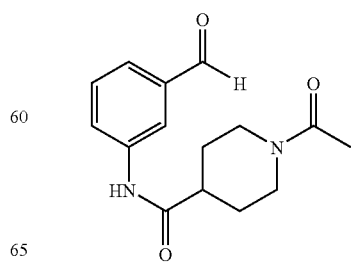

To a solution of 3-amino-benzaldehyde (200 mg, 1.65 mmol) and TEA (0.13 ml) in DCM (4 ml) at 0° C., was added 1-acetylpiperidine-4-carbonyl chloride (0.6 g, 3.3 mmol) and the resulting solution was allowed to warm to room temperature and stirred for 2 days. NaHCO$_3$ was then added and the mixture was repeatedly extracted with DCM, the organic layers were then washed with HCl (1 M). The organic layers were combined, dried (MgSO$_4$), filtered and evaporated in vacuo. The title compound was obtained as a cream oil, 97 mg, 22% yield.

R.f 0.42 (10% MeOH in DCM),

LCMS: t$_r$=0.99 min (95% MeOH in water), m/z M−H 273.39,

HPLC: t$_r$=1.26 min (90% ACN in H$_2$O), 81%, $^1$H NMR (CDCl$_3$, 270 MHz): δ 1.66-1.90 (2H, m, CH$_2$), 1.95-2.03 (2H, m, CH$_2$), 2.11 (3H, s, CH$_3$), 2.50-2.61 (1H, m, CH), 2.66-2.76 (1H, m, ½CH$_2$), 3.09-3.20 (1H, m, ½CH$_2$), 3.89-3.94 (1H, m, ½CH$_2$), 4.61-4.65 (1H, m, ½CH$_2$), 7.48 (1H, t, J=7.9 Hz, ArH), 7.61 (1H, td, J=1.2, 7.7 Hz, ArH), 7.90-8.00 (4H, m, ArH and NH), 9.97 (1H, s, CHO).

Synthesis of 1-acetyl-piperidine-4-carboxylic acid (3-[2-(4-chloro-phenoxy)-phenyl amino]-methyl-phenyl)-amide, C$_{27}$H$_{28}$ClN$_3$O$_3$, MW 477.98

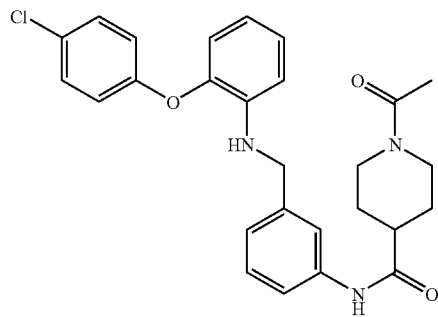 [SMILES: CC(=O)N1CCC(C(=O)Nc2cccc(CNc3ccccc3Oc3ccc(Cl)cc3)c2)CC1]

Using the general procedure for the reductive amination of the substituted diphenylether aniline with the substituted 2-acetamide benzaldehyde the desired compound was isolated as a cream waxy solid, 70 mg, 41% yield.

R.f 0.22 (10% MeOH in EtOAc),

LCMS: t$_r$=5.5 min (50% to 95% MeOH in water at 0.5 ml/min to 1.0 ml/min over 5 min), m/z M−H 476.42, HPLC: t$_r$=1.73 min (90% ACN in H$_2$O), 93%, $^1$H NMR (CDCl$_3$, 270 MHz): δ 1.63-1.77 (2H, m, CH$_2$), 1.78-1.90 (2H, m, CH$_2$), 2.09 (3H, s, CH$_3$), 2.38-2.50 (1H, m, CH), 2.63-2.73 (1H, m, ½CH$_2$), 3.11 (1H, td, J=2.7, 13.9 Hz, ½CH$_2$), 3.88 (1H, d, J=13.6 Hz, ½CH$_2$), 4.33 (2H, s, CH$_2$), 4.58-4.63 (2H, m, ½CH$_2$ and NH), 6.60-6.66 (2H, M, ArH), 6.82- (1H, dd, J=1.5, 8.4 Hz, ArH), 6.86-6.92 (2H, m, ArH), 6.95-7.06 (2H, m, ArH), 7.21-7.28 (3H, m, ArH), 7.39-7.44 (3H, m, ArH and NH).

$^{13}$C NMR (CDCl$_3$, 68 MHz): δ 21.6 (CH$_3$), 28.6, 28.9, 41.0, (CH$_2$), 44.1 (CH), 45.8, 47.6 (CH$_2$), 112.0, 117.2, 118.5, 118.7, 118.8, 119.4, 123.2, 125.4 (ArCH), 127.7 (ArC), 129.4, 129.8 (ArCH), 129.8, 138.1, 140.2, 140.5 (ArC), 169.0, 172.3 (CO).

HRMS: Calcd for C$_{27}$H$_{28}$ClN$_3$O$_3$ (M+H)$^+$ 478.1892. found (M+H)$^+$ 478.1878.

Synthesis of N-(2-1-[2-(4-chloro-phenoxy)- phenylamino]-ethyl-phenyl)-ethylamine, C$_{22}$H$_{23}$ClN$_2$O, MW 366.88

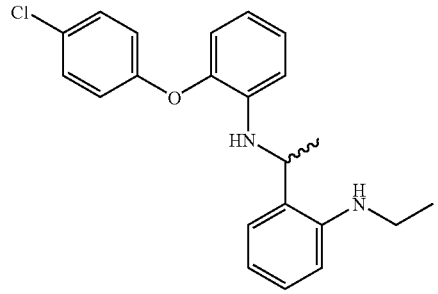 [SMILES: CCNc1ccccc1C(C)Nc1ccccc1Oc1ccc(Cl)cc1]

A solution of 2-(4-chloro-phenoxy)-phenylamine (298 mg, 1.4 mmol), N-(2-acetyl-phenyl)-acetamide, (200 mg, 1.13 mmol) and chlorotriisopropoxytitanium IV (0.53 ml, 2.26 mmol) in toluene (15 ml) was stirred at r.t. for 4 days. NaHCO$_3$ was added and the mixture was extracted repeatedly with EtOAc, dried (MgSO$_4$) and evaporated to dryness. The residue was re-dissolved in THF (20 ml) and cooled to 0° C., to this was added succinic acid (270 mg, 2.26 mmol) and borane (1M in THF, 2.3 ml, 2.26 mmol). The reaction was slowly warmed to r.t. and stirred for 8 h. NaHCO$_3$ was added and the volatile solvents removed in vacuo, the mixture was then extracted with EtOAc and dried (MgSO$_4$). The crude material was purified by flash chromatography (0-100% DCM in hexane) to yield the product, 79 mg, 19% yield.

LCMS: t$_r$=1.42 min (95% MeOH in water), m/z M−H 365.33,

HPLC: t$_r$=4.49 min (90% ACN in water), 97%, $^1$H NMR (CDCl$_3$, 270 MHz): δ 1.17 (3H, t, J=7.2 Hz, CH$_3$CH$_2$), 1.56 (3H, d, J=6.7 Hz, CH$_3$CH), 3.10 (2H, q, J=14.1 Hz, CH$_2$), 4.22 (1H, d, J=6.0 Hz, NH), 4.53 (1H, q, J=13.3 Hz, CH), 4.59 (1H, br.s, NH), 6.66-6.93 (7H, m, ArH), 7.01 (1H, td, J=7.9, 1.5 Hz, ArH), 7.16-7.31 (4H, m, ArH).

$^{13}$C NMR (CDCl$_3$, 68 MHz): 14.9, 19.9 (CH$_3$), 38.1 (CH$_2$), 50.9 (CH), 111.1, 113.6, 117.0, 118.0, 118.6, 119.5, 125.5, 126.5 (ArCH), 128.6, 127.8 (ArC), 128.3, 129.7 (ArCH), 13.7, 143.3, 146.7, 156.4 (ArC).

HRMS: Calcd for C$_{22}$H$_{23}$ClN$_2$O (M+Na)$^+$ 389.1386. found (M+Na)$^+$ 389.1391.

Synthesis of N-(2-(1-[2-(4-chloro-phenoxy)- phenylamino]-ethyl)-phenyl)-N-ethyl-acetamide, C$_{24}$H$_{25}$ClN$_2$O$_2$, MW 408.92

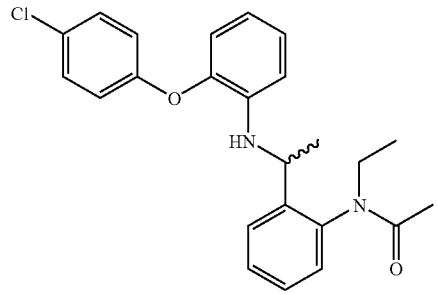 [SMILES: CCN(C(C)=O)c1ccccc1C(C)Nc1ccccc1Oc1ccc(Cl)cc1]

N-(2-(1-[2-(4-Chloro-phenoxy)-phenylamino]-ethyl)-phenyl)-ethane (50 mg, 0.14 mmol) was dissolved in DCM (1 ml) and cooled to 0° C., to this was added acetyl chloride (0.04 ml, 0.56 mmol) and TEA (0.02 ml, 0.42 mmol). This was then allowed to warm to room temperature and stirred for 1 h. Saturated NaHCO$_3$ solution was added and the mixture was extracted with DCM, dried (MgSO$_4$) and purified by flash chromatography to yield the title compound as an off-white oil, 23 mg, 40% yield.

R.f 0.55 (EtOAc),

LCMS: $t_r$=1.37 min (95% MeOH in water), m/z M–H 407.34,

HPLC: $t_r$=3.03 min (90% ACN in H$_2$O), 96%, $^1$H NMR (CDCl$_3$, 270 MHz): δ 1.15 (3H, dt, J=6.8, 10.4 Hz, CH$_3$CH$_2$), 1.43 (3H, dd, J=6.4, 15.6 Hz, CH$_3$CH), 1.74 (3H, d, J=25.6 Hz, CH$_3$CO), 3.07-3.15 (1H, m, ½CH$_2$), 4.24-4.36 (2H, m, ½CH$_2$ and NH), 4.64-4.75 (1H, m, CH), 6.51 (1H, dd, J=1.6, 8.4 Hz, ArH), 6.57-6.67 (2H, m, ArH), 6.74-6.84 (2H, m, ArH), 6.86-6.90 (1H, m, ArH), 6.92-6.97 (1H, m, ArH), 7.06 (1H, td, J=1.6, 8.0 Hz, ArH), 7.21-7.35 (4H, m, ArH), 7.39-7.47 (1H, m, ArH).

$^{13}$C NMR (CDCl$_3$, 68 MHz): 12.8, 22.5, 23.1 (CH$_3$), 43.5 (CH$_2$), 47.5 (CH), 112.7, 117.7, 118.8, 119.4, 125.3, 126.9, 128.3, 129.4, 129.7, 130.3 (ArCH), 138.9, 139.9, 141.7, 142.4, 143.1, 156.3 (ArC), 170.5 (CO).

HRMS: Calcd for C$_{24}$H$_{25}$ClN$_2$O$_2$ (M+H)$^+$ 431.1497. found (M+H)$^+$ 431.1487.

Synthesis of N-(2-([2-(4-chloro-phenoxy)-phenylimino]-methyl)-phenyl)-acetamide, C$_{21}$H$_{17}$ClN$_2$O$_2$, MW 364.82, (Method 1)

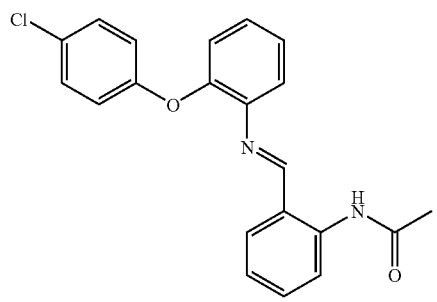 [SMILES: CC(=O)Nc1ccccc1/C=N/c1ccccc1Oc1ccc(Cl)cc1]

A solution of 2-(4-chloro-phenoxy)-phenylamine (100 mg, 0.46 mmol) and N-(2-formyl-phenyl)-acetamide (74 mg, 0.46 mmol) in anhydrous DCM (5 ml) was stirred at r.t. and to this was added MgSO$_4$ (550 mg, 4.6 mmol) and the resulting mixture stirred for a further 18 h at r.t. The mixture was then filtered and the solid was washed with DCM. The filtrate was then evaporated to dryness to yield the desired product. The product was identified by NMR, as no CHO peak was visible in the $^1$H NMR and it had been replaced with an imine peak. The product was used crude in all following experiments.

Synthesis of N-(2-([2-(4-chloro-phenoxy)-phenylimino]-methyl)-phenyl)-acetamide, C$_{21}$H$_{17}$ClN$_2$O$_2$, MW 364.82, (Method 2)

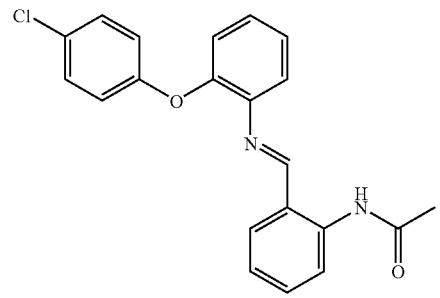 [SMILES: CC(=O)Nc1ccccc1/C=N/c1ccccc1Oc1ccc(Cl)cc1]

A solution of 2-(4-chloro-phenoxy)-phenylamine (100 mg, 0.46 mmol) and N-(2-formyl-phenyl)-acetamide (74 mg, 0.46 mmol) in anhydrous DCM (5 ml) was stirred at r.t. and to this was added TiCl(O$^i$Pr)$_3$ (0.25 mL, 1 mmol). The resulting mixture was stirred for a further 4 h at room temperature. The mixture was then evaporated to dryness to yield the desired product. As in Method 1 (see above) the product could easily be identified by $^1$H NMR. The product was used crude in all following experiments.

$^1$H NMR (CDCl$_3$, 270 MHz): δ 2.03 (3H, s, CH$_3$), 6.87-7.46 (11H, m, ArH), 8.60 (1H, s, N=CH), 8.72 (1H, d, J=8.5 Hz, ArH).

$^{13}$C NMR (CDCl$_3$, 101 MHz): 24.9 (CH$_3$), 116.7, 119.2, 119.6, 120.3 (ArCH), 120.6 (ArC), 122.5, 125.0, 127.9 (ArCH), 128.2 (ArC), 129.8, 132.7 (ArCH), 140.4, 141.7, 149.6, 156.1 (ArC), 163.4 (CH), 169.9 (CO).

Synthesis of N-(2-(1-[2-(4-chloro-phenoxy)-phenylamino]-but-2-enyl)-phenyl)-acetamide, C$_{24}$H$_{23}$ClN$_2$O$_2$, MW 406.90

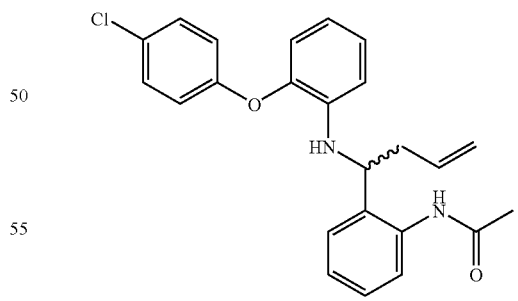

N-(2-([2-(4-Chloro-phenoxy)-phenylimino]-methyl)-phenyl)-acetamide (500 mg, assumed 100% pure, 1.4 mmol) was dissolved in THF (15 ml) and cooled to 0° C. under a N$_2$ atmosphere, to this was added BF$_3$OEt$_2$ (0.18 ml, 1.4 mmol) and allylmagnesium bromide (1 M in ether, 4.2 ml, 4.2 mmol). The resulting solution was stirred at r.t. for 18 h. The reaction was then quenched with sat. NH$_4$Cl solution then extracted with EtOAc and dried (MgSO$_4$). The crude product was purified by flash chromatography (0-50% EtOAc in hexane) to yield the desired product as a light brown solid, 320 mg, 57% yield.

R.f 0.36 (DCM),

LCMS: $t_r$=1.59 min (95% MeOH in water), m/z M+H (+Na) 429.13, M+H 407.15,

HPLC: $t_r$=2.45 min (90% ACN in water), 92%,

HRMS: Calcd for $C_{24}H_{23}ClN_2O_2$ (M+H)$^+$ 407.1521. found (M+H)$^+$ 407.1503.

Synthesis of N-(2-(1-[2-(4-chloro-phenoxy)-phenylamino]-2-phenyl-ethyl)-phenyl)-acetamide, MW 456.96

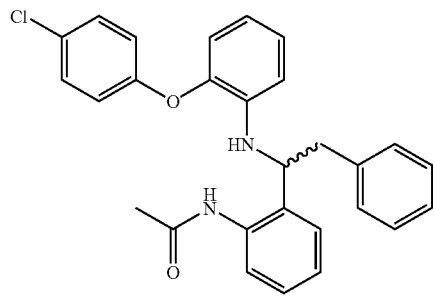 [SMILES: CC(=O)Nc1ccccc1C(Cc1ccccc1)Nc1ccccc1Oc1ccc(Cl)cc1]

N-(2-([2-(4-Chloro-phenoxy)-phenylimino]-methyl)-phenyl)-acetamide (111 mg, assumed 100% pure, 0.3 mmol) was dissolved in THF (5 ml) and cooled to 0° C. under a $N_2$ atmosphere, to this was added $BF_3OEt_2$ (0.04 ml, 0.3 mmol) and benzylmagnesium bromide (2 M in THF, 0.3 ml, 1.2 mmol). The resulting solution was stirred at r.t. for 18 h. The reaction was then quenched with sat. $NH_4Cl$ solution, extracted with EtOAc and dried ($MgSO_4$). The crude product was purified by flash chromatography (0-20% EtOAc in DCM) to yield the desired product, 20 mg, 14% yield.

R.f 0.25 (DCM),

LCMS: $t_r$=1.26 min (95% MeOH in water), m/z M−H 455.15,

HPLC: $t_r$=2.73 min (90% ACN in water), 97%, $^1$H NMR (CDCl$_3$, 400 MHz): δ 1.82 (3H, s, CH$_3$), 3.02-3.04 (2H, m, CH$_2$), 4.43 (1H, t, J=8.0 Hz, CH), 4.50 (1H, br.s, NH), 6.52 (1H, d, J=6.8 Hz, ArH), 6.63-6.74 (4H, m, ArH), 6.79-6.84 (1H, m, ArH), 6.98-7.00 (1H, m, ArH), 7.05 (1H, t, J=7.2 Hz, ArH), 7.15-7.24 (7H, m, ArH), 7.91 (1H, d, J=8.4 Hz, ArH), 8.90 (1H, br.s, NHCO).

$^{13}$C NMR (CDCl$_3$, 101 MHz): 24.3 (CH$_3$), 42.9 (CH$_2$), 60.8 (CH), 114.9, 117.9, 119.6, 119.7, 123.4, 124.9, 125.6, 127.2 (ArCH), 127.9 (ArC), 128.1, 128.2, 128.9, 129.1, 129.8 (ArCH), 131.2, 136.7, 136.8, 139.3, 143.4, 156.0 (ArC), 168.2 (CO).

HRMS: Calcd for $C_{28}H_{25}ClN_2O_2$ (M+H)$^+$ 457.1677. found (M+H)$^+$ 457.1666.

Synthesis of N-(2-(1-[2-(4-chloro-phenoxy)-phenylamino]-butyl)-phenyl)-acetamide, $C_{24}H_{25}ClN_2O_2$, MW 408.92

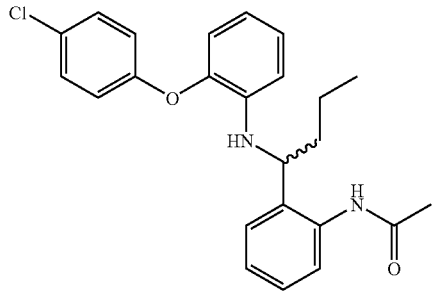 [SMILES: CCCC(Nc1ccccc1Oc1ccc(Cl)cc1)c1ccccc1NC(C)=O]

To a solution of N-(2-(1-[2-(4-chloro-phenoxy)-phenylamino]-but-2-enyl)-phenyl)-acetamide, (50 mg, 0.12 mmol) in EtOAc (25 ml) was added Pd/C (15 mg). The solution was then stirred under a $H_2$ atmosphere for 15 min and filtered through celite. Purification by flash chromatography (0-50% EtOAc in hexane) afforded the desired product, 44 mg, 88% yield.

R.f 0.42 (EtOAc),

LCMS: $t_r$=3.72 min (90% MeOH in water), m/z M+H 409.00,

HPLC: $t_r$=4.69 min (90% MeOH in water), 99%, $^1$H NMR (CDCl$_3$, 400 MHz): δ 0.90 (3H, t, J=7.6 Hz, CH$_2$CH$_3$), 1.21-1.39 (2H, m, CH$_2$), 1.79-1.86 (2H, m, CH$_2$), 1.87 (3H, s, CH$_3$CO), 4.29 (1H, t, J=7.6 Hz, CH), 4.37 (1H, br.s, NH), 6.70 (1H, d, J=8.0 Hz, ArH), 6.73-6.78 (1H, m, ArH), 6.85-6.87 (1H, m, ArH), 6.90-6.96 (3H, m, ArH), 7.11 (1H, t, J=7.2 Hz, ArH), 7.25-7.31 (4H, m, ArH), 8.05 (1H, d, J=8.0 Hz, ArH), 9.36 (1H, br.s, NHCO).

$^{13}$C NMR (CDCl$_3$, 101 MHz): 13.7 (CH$_3$CH$_2$), 19.6 (CH$_2$), 24.4 (CH$_3$CO), 38.0 (CH$_2$), 60.0 (CH), 114.7, 118.3, 119.4, 119.5, 123.0, 124.4, 125.4, 127.9, 128.1, 128.5, 129.9 (ArCH), 130.9, 136.8, 139.3, 143.7, 156.0 (ArC), 168.1 (CO).

HRMS: Calcd for $C_{24}H_{25}ClN_2O_2$ (M+H)$^+$ 409.1677. found (M+H)$^+$ 409.1677.

Synthesis of N-(2-(1-[2-(4-chloro-phenoxy)-phenylamino]-ethyl)-phenyl)-acetamide, $C_{22}H_{21}ClN_2O_2$, MW 380.87

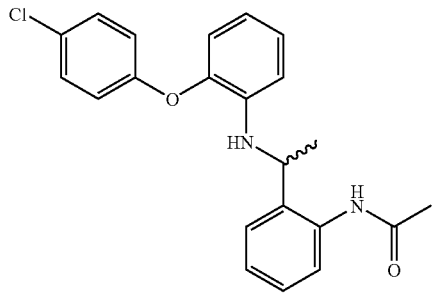 [SMILES: CC(=O)Nc1ccccc1C(C)Nc1ccccc1Oc1ccc(Cl)cc1]

A cerium chloride suspension was prepared as follows: CeCl$_3$.7H$_2$O (stored in the oven, 515 mg, 1.38 mmol) was heated under high-vac for 15 min and allowed to cool to r.t. then 0° C. in an ice bath. To this was added THF (3 ml) and methylmagnesium bromide (3 M in diethyl ether, 0.46 ml, 1.38 mmol), this was then stirred at r.t. for 2 h. To this was added N-(2-([2-(4-chloro-phenoxy)-phenylimino]-methyl)-phenyl)-acetamide intermediate (166 mg, 0.46 mmol) and stirred at r.t. for a further 18 h. NaHCO$_3$ was added and the mixture was extracted with EtOAc, dried (MgSO$_4$) and purified by flash chromatography (0-100% DCM) to yield the desired product as an off white oil, 14 mg, 8% yield.

R.f 0.56 (DCM with TEA),

LCMS: $t_r$=1.08 min (90% MeOH in water), m/z M+Na 403.20,

HPLC: $t_r$=2.6 min (90% ACN in water), 94%, $^1$H NMR (CDCl$_3$, 270 MHz): δ 1.55 (3H, d, J=6.6 Hz, CH$_3$CH), 1.90 (3H, s, CH$_3$CO), 4.25 (1H, d, J=3.0 Hz, CHNH), 4.52-4.54 (1H, m, CH), 6.73-6.78 (2H, m, ArH), 6.84-6.99 (4H, m, ArH), 7.11 (1H, t, J=7.7 Hz, ArH), 7.24-7.31 (4H, m, ArH), 8.02 (1H, d, J=8.0 Hz, ArH), 9.16 (1H, br.s, NH).

$^{13}$C NMR (CDCl$_3$, 101 MHz): 21.5, 24.4 (CH$_3$), 53.9 (CH), 114.6, 118.5, 119.4, 119.6, 123.2, 124.7, 125.4, 127.3, 128.1 (ArCH), 128.2 (ArC), 129.9 (ArCH), 132.0, 136.8, 138.9, 143.9, 155.9 (ArC), 168.2 (CO).

HRMS: Calcd for C$_{22}$H$_{21}$ClN$_2$O$_2$ (M+H)$^+$ 381.1364. found (M+H)$^+$ 381.1352.

Synthesis of 1-bromo-2-phenoxy-benzene, C$_{12}$H$_9$BrO, MW 249.10

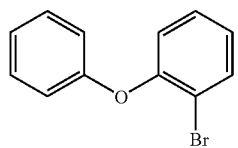 [SMILES: Brc1ccccc1Oc1ccccc1]

A mixture of 2-bromophenol (0.211 ml, 2 mmol), phenylboronic acid (490 mg, 4 mmol), copper acetate (364 mg, 2 mmol), TEA (1.38 ml, 10 mmol) and 4 Å molecular sieves in DCM (25 ml) was stirred at r.t. for 18 h. The slurry was filtered through celite and concentrated in vacuo. This was then diluted with EtOAc and NaHCO$_3$ solution, extracted and the organic portions were washed with brine and dried (MgSO$_4$). The crude mixture was purified by flash chromatography (hexane) to yield the desired product as a colourless oil, 232 mg, 47% yield.

R.f 0.75 (DCM),

LCMS: $t_r$=1.3 min (95% MeOH in water), m/z M−H 246.84, 248.86,

HPLC: $t_r$=2.88 min (90% ACN in water), 98%, $^1$H NMR (CDCl$_3$, 270 MHz): δ 6.95-7.04 (4H, m, ArH), 7.11 (1H, td, J=1.1, 8.0 Hz, ArH), 7.22-7.37 (3H, m, ArH), 7.61-7.65 (1H, m, ArH), $^{13}$C NMR (CDCl$_3$, 68 MHz): 115.0 (ArC), 118.2, 120.7, 123.5, 125.1, 128.8, 129.9, 133.9 (ArCH), 153.8, 156.9 (ArC).

Synthesis of 1-bromo-2-phenoxy-4' chlorobenzene, C$_{12}$H$_8$BrClO, MW 283.55

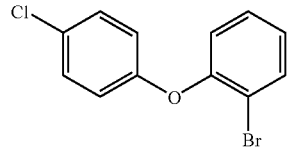 [SMILES: Clc1ccc(Oc2ccccc2Br)cc1]

A mixture of 2-bromophenol (0.2 ml, 2 mmol), phenylboronic acid (600 mg, 4 mmol), copper acetate (350 mg, 2 mmol), TEA (1.4 ml, 10 mmol) and powdered 4 Å molecular sieves (~2 g) in DCM (25 ml) was stirred at r.t. for 18 h. The slurry was filtered through celite and concentrated in vacuo. This was then diluted with EtOAc and NaHCO$_3$ solution, extracted and the organic portions were washed with brine and dried (MgSO$_4$). The crude mixture was purified by flash chromatography (hexane) to yield the desired product as a colourless oil, 320 mg, 59% yield.

R.f 0.72 (DCM),

HPLC: $t_r$=3.29 min (90% ACN in water), >99%, $^1$H NMR (CDCl$_3$, 270 MHz,): δ 6.85-6.91 (1H, m, ArH), 6.96 (1H, dd, J=1.4, 8.0 Hz, ArH), 7.00-7.07 (1H, m, ArH), 7.25-7.29 (3H, m, ArH), 7.62 (1H, dd, J=1.6, 8.0 Hz, ArH).

Synthesis of 1-(2-nitro-phenyl)-ethanone-O-methyl-oxime, C$_9$H$_{10}$N$_2$O$_3$, MW 194.19

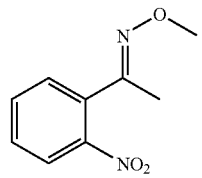

To a solution of 2-nitroacetophenone (1.9 g, 10.9 mmol), methoxyamine hydrochloride (0.96 g, 10.9 mmol) in anhydrous pyridine (38 ml) and anhydrous EtOH (38 ml) was added powdered 4 Å molecular sieves (~1 g). The resulting mixture was heated at reflux for 3 h. The resulting mixture was filtered through celite to remove the molecular sieves and then evaporated to dryness. The solid was re-dissolved in EtOAc and extracted with 20% NaHCO$_3$ solution, this was then dried (MgSO$_4$) and evaporated in vacuo to yield the desired compound as a mixture of enantiomers, yellow oil, 1.95 g, 87% yield. The product was used crude in following reactions.

R.f 0.55 (DCM),

HPLC: $t_r$=1.87 min (90% ACN in water), 58%, $t_r$=2.39 min (90% ACN in water), 29%, LCMS: $t_r$=3.30 min (70% MeOH in water), m/z M$^+$H 195.4, $t_r$=4.00 min (70% MeOH in water), m/z M$^+$H 195.3, Synthesis of 1-(2-nitro-phenyl)-ethylamine hydrochloride, $C_8H_{11}ClN_2O_2$, MW 202.64

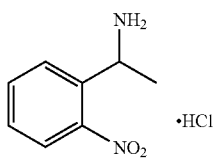

A solution of 1-(2-nitro-phenyl)-ethanone-O-methyl-oxime (1.95 g, 10.05 mmol) in THF (7 ml) was cooled to 0° C., to this was added borane/THF complex (28 ml, 28.1 mmol) and the resulting solution was then heated at reflux for 6 h. The reaction was then cooled to −20° C. and water (2 ml) was added slowly followed by aq. 20% KOH solution (2 ml) over 20 min. The resulting mixture was then heated at reflux for a further 2 h and then poured into DCM. The mixture was then extracted with brine and dried (MgSO$_4$). To form the salt, the product was re-dissolved in DCM and then conc. HCl (1.5 ml) was added and the mixture was stirred for 1 h. The resulting solid was removed by filtration and washed with ether and dried, 345 mg, 17% yield.

R.f 0.32 (Hexane: DCM, 1:1),

LCMS: $t_r$=1.33 min (70% MeOH in water), m/z M+H 167.2 (free base),

HPLC: $t_r$=2.09 min (90% ACN in water), >99%, $^1$H NMR (CDCl$_3$, 400 MHz): δ 1.60 (3H, d, J=6.8 Hz, CH$_3$), 4.77-4.80 (1H, m, CH), 7.63-7.67 (1H, m, ArH), 7.86 (1H, td, J=1.2, 7.6 Hz, ArH), 8.03-8.05 (2H, m, ArH), 8.72 (2H, br.s, NH$_2$).

Synthesis of [2-(4-chloro-phenoxy)-phenyl]-[1-(2-nitro-phenyl)-ethyl]-amine, $C_{20}H_{17}ClN_2O_3$, MW 368.81

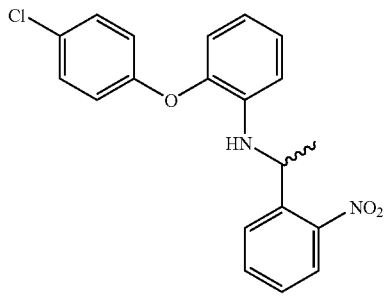 [SMILES: CC(Nc1ccccc1Oc1ccc(Cl)cc1)c1ccccc1[N+](=O)[O-]]

Palladium acetate (15 mg, 10 mol %), rac-BINAP (45 mg, 10 mol %) and 1-(2-nitro-phenyl)-ethylamine hydrochloride (151 mg, 0.75 mmol) were placed into an over dried flask, this was evacuated and back filled with N$_2$. To this was then added (via syringe) 1-bromo-2-phenoxy-4' chlorobenzene (190 mg, 0.68 mmol) and toluene (2 ml). This was stirred for 10 min at r.t. Sodium t-butoxide (195 mg, 2.04 mmol) and a further portion of toluene (2 ml) was then added. The resulting solution was heated to reflux for 24 hThe slurry was then filtered through celite and purified by flash chromatography (0-100% DCM in hexane) to yield the desired product as a yellow oil, 120 mg, 48% yield.

R.f 0.45 (1:1, Hexane: DCM),

LCMS: $t_r$=3.85 min (90% MeOH in water), m/z M−H 367.50, $^1$H NMR (CDCl$_3$, 400 MHz): δ 1.51 (3H, d, J=6.8 Hz, CH$_3$), 5.16 (1H, q, J=6.4 Hz, CH), 6.28 (1H, dd, J=1.2, 7.6 Hz, ArH), 6.56 (1H, td, J=1.2, 7.6 Hz, ArH), 6.76 (1H, dd, J=1.6, 8.4 Hz, ArH), 6.82 (1H, td, J=1.2, 7.2 Hz, ArH), 6.89-6.93 (2H, m, ArH), 7.24-7.28 (2H, m, ArH), 7.31-7.35 (1H, m, ArH), 7.47 (1H, td, J=1.2, 7.6 Hz, ArH), 7.54 (1H, dd, J=1.2, 8.0 Hz, ArH), 7.88 (1H, dd, J=1.2, 8.4 Hz, ArH).

Synthesis of [2-(4-chloro-phenoxy)-phenyl][1-(2-amino-phenyl)-ethyl]-amine, $C_{20}H_{19}ClN_2O$, MW 338.83

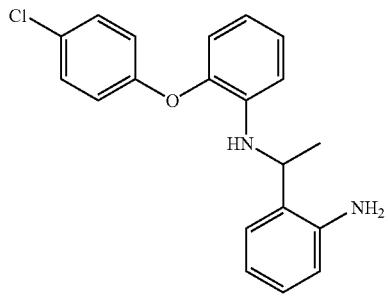 [SMILES: CC(Nc1ccccc1Oc1ccc(Cl)cc1)c1ccccc1N]

Using the general procedure for the reduction of the substituted 2-nitrobenzylalcohol, but with a shortened reaction time of 10 min at reflux, the product was isolated as a yellow oil, 12 mg, 25% yield.

R.f 0.32 (DCM),

LCMS: $t_r$=2.81 min (90% MeOH in water), m/z M−H 337.60, $^1$H NMR (CDCl$_3$, 400 MHz): δ 1.53 (3H, d, J=6.8 Hz, CH$_3$), 4.06 (2H, br.s, NH$_2$), 4.21 (1H, br.s, NH), 4.54-4.56 (1H, m, CH), 6.63-6.67 (2H, m, ArH), 6.70-6.77 (2H, m, ArH), 6.81 (1H, dd, J=0.8, 7.6 Hz, ArH), 6.87-6.91 (2H, m, ArH), 6.95-6.99 (1H, m, ArH), 7.07 (1H, td, J=0.8, 7.2 Hz, ArH), 7.19 (1H, dd, J=1.2, 7.6 Hz, ArH), 7.23-7.27 (2H, m, ArH).

$^{13}$C NMR (CDCl$_3$, 101 MHz): 20.2 (CH$_3$), 50.1 (CH), 113.3, 116.6, 117.7, 118.6, 118.7, 119.3, 125.3, 126.7 (ArCH), 127.5, 127.7 (ArC), 128.0, 129.6 (ArCH), 139.5, 143.1, 144.8, 156.2 (ArC).

Chiral Separation of R-(−)-N-(2-(1-[2-(4-chloro-phenoxy)-phenylamino]-but-2-enyl)-phenyl)-acetamide, $C_{24}H_{23}ClN_2O_2$, MW 406.90

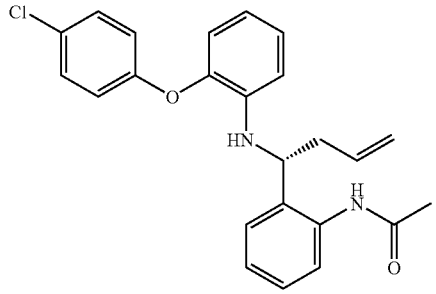 [SMILES: C=CC[C@@H](Nc1ccccc1Oc1ccc(Cl)cc1)c1ccccc1NC(C)=O]

m.p. 139-140° C.,

LCMS (Chiracel AD-H column): $t_r$=11.5 min (80% MeOH in water), m/z M−H 405.2,

HPLC (Chiracel AD-H column): $t_r$=9.00 min (80% MeOH in water), >99%, $[\alpha]_D$=−155.7, $^1$H NMR (CDCl$_3$, 400 MHz): δ 1.86 (3H, s, CH$_3$), 2.54-2.62 (2H, m, CH$_2$), 4.31 (1H, t, J=6.4 Hz, CHNH), 4.60 (1H, s, NH), 5.10 (1H, s, ½CH$_2$CH), 5.13 (1H, d, J=5.2 Hz, ½CH$_2$CH), 5.65-5.75 (1H, m, CHCH$_2$), 6.66 (1H, d, J=8.0 Hz, ArH), 6.77 (1H, t, J=8.0 Hz, ArH), 6.87-6.96 (4H, m, ArH), 7.13 (1H, t, J=7.6 Hz, ArH), 7.26-7.31 (4H, m, ArH), 8.05 (1H, d, J=8.4 Hz, ArH), 9.40 (1H, br.s, NHCO).

$^{13}$C NMR (CDCl$_3$, 101 MHz): 24.3 (CH$_3$), 40.6 (CH$_2$), 58.9 (CH$_2$), 114.9, 118.0 (ArCH), 119.3 (CH$_2$), 119.8, 120.0, 123.1, 124.7, 125.6 (ArCH), 128.0 (ArC), 128.2, 128.2, 129.8 (ArCH), 130.7 (ArC), 134.0 (CH), 136.9, 139.3, 143.5, 156.1 (ArC), 168.1 (CO).

Anal. Calcd for C$_{24}$H$_{23}$ClN$_2$O$_2$. ½H$_2$O C, 69.31; H, 5.82; N, 6.74%. Found: C, 68.9; H, 5.75; N, 6.50%.

HRMS: Calcd for C$_{24}$H$_{23}$ClN$_2$O$_2$ (M+H)$^+$ 407.1521. found (M+H)$^+$ 407.1503.

X-Ray Crystallography used to determine absolute stereochemistry.

Chiral Separation of S-(+)- N-(2-(1-[2-(4-chlorophenoxy)-phenylamino]-but-2-enyl)-phenyl)-acetamide, C$_{24}$H$_{23}$ClN$_2$O$_2$, MW 406.90

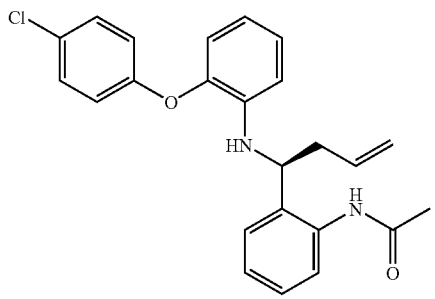 [SMILES: C=CC[C@H](Nc1ccccc1Oc1ccc(Cl)cc1)c1ccccc1NC(C)=O]

m.p. 139-141° C.,

LCMS (Chiracel AD-H column): $t_r$=14.8 min (80% MeOH in water), m/z M−H 405.4,

HPLC (Chiracel AD-H column): $t_r$=11.50 min (90% ACN in water), >99%, $[\alpha]_D$=+158.0, $^1$H NMR (CDCl$_3$, 400 MHz): δ 1.86 (3H, s, CH$_3$), 2.54-2.62 (2H, m, CH$_2$), 4.31 (1H, t, J=6.4 Hz, CHNH), 4.60 (1H, s, NH), 5.10 (1H, s, ½CH$_2$CH), 5.13 (1H, d, J=5.2 Hz, ½CH$_2$CH), 5.65-5.75 (1H, m, CHCH$_2$), 6.66 (1H, d, J=8.0 Hz, ArH), 6.77 (1H, t, J=8.0 Hz, ArH), 6.87-6.96 (4H, m, ArH), 7.13 (1H, t, J=7.6 Hz, ArH), 7.26-7.31 (4H, m, ArH), 8.05 (1H, d, J=8.4 Hz, ArH), 9.40 (1H, br.s, NHCO).

$^{13}$C NMR (CDCl$_3$, 101 MHz): 24.3 (CH$_3$), 40.6 (CH$_2$), 58.9 (CH$_2$), 114.9, 118.0 (ArCH), 119.3 (CH$_2$), 119.8, 120.0, 123.1, 124.7, 125.6 (ArCH), 128.0 (ArC), 128.2, 128.2, 129.8 (ArCH), 130.7 (ArC), 134.0 (CH), 136.9, 139.3, 143.5, 156.1 (ArC), 168.1 (CO).

Anal. Calcd for C$_{24}$H$_{23}$ClN$_2$O$_2$. ½H$_2$O C, 69.31; H, 5.82; N, 6.74%. Found: C, 69.7; H, 5.74; N, 6.75%.

HRMS: Calcd for C$_{24}$H$_{23}$ClN$_2$O$_2$ (M+H)$^+$ 407.1521. found (M+H)$^+$ 407.1502.

Preparation of 1-(3-((2-(4-chlorophenoxy)phenylamino)methyl)-1H-indol-1-yl)ethanone C$_{23}$H$_{19}$ClN$_2$O$_2$, Mol. Wt.: 390.86

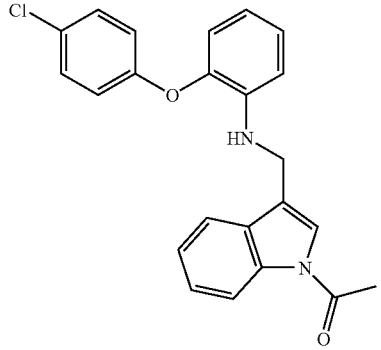 [SMILES: CC(=O)n1cc(CNc2ccccc2Oc2ccc(Cl)cc2)c2ccccc21]

A solution of the aniline (250 mg, 1.14 mmol), 1-acetyl-3-indolecarboxaldehyde (107 mg, 0.57 mmol), NaBH(OAc)$_3$ (302 mg, 1.43 mmol) and AcOH (205 mg, 3.42 mmol) in 1,2-DCE (3 ml) was stirred at room temperature for 16 h. The reaction was quenched with a saturated aqueous solution of sodium bicarbonate (5 ml) and extracted with EtOAc (3×5 ml). The combined organics were dried (MgSO$_4$), filtered and concentrated in vacuo before purification by flash chromatography (eluant; 8:2 hexane:EtOAc to EtOAc) proceeded to afford the desired product which was recrystallised from EtOAc and hexane to afford a cream solid (174.1 mg, 78%).

$^1$H NMR: (CDCl$_3$, 270 MHz): δ 2.56 (3H, s, CH$_3$), 3.77 (1H, br s, NH), 4.47 (2H, br s, CH2), 6.65-7.50 (12H, m, ArH), 8.41 ppm (1H, d, J=7.9 Hz, ArH).

$^{13}$C NMR: (CDCl$_3$, 67.93 MHz): δ 24.1, 39.7, 112.1, 117.0, 117.6, 118.5, 119.0, 119.6, 120.1, 123.0, 123.7, 125.5, 125.7, 128.0, 129.7, 136.1, 140.0, 143.5, 156.2, 168.6 ppm.

LCMS: 1.550 min, (95% MeOH:5% water at 1.0 ml/min), AP$^-$: 389.20.

HPLC: 3.410 min, 95.90% purity, (isocratic, 90% acetonitrile: 10% water at 1.0 ml/min).

HRMS (MicroTOF): C$_{23}$H$_{20}$ClN$_2$O$_2$ requires 391.1208, found 391.1194.

M. Pt. 107-108° C.

Preparation of 1-acetyl-5-methoxy-1H-indole-3-carbaldehyde

C$_{12}$H$_{11}$NO$_3$, Mol. Wt.: 217.22

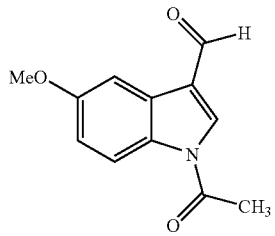 [SMILES: COc1ccc2c(c1)c(C=O)cn2C(C)=O]

To a solution of 5-methoxyindole-3-carboxaldehyde (250 mg, 1.43 mmol) and triethylamine (195 mg, 1.93 mmol) in DCM (14 ml) was added acetyl chloride (152 mg, 1.93 mmol) at 0° C.

The reaction was then stirred at reflux for 90 min before being cooled to room temperature and stirred for a further 14 h. The mixture was poured on to a solution of 2 M HCl (20 ml) and extracted with DCM (3×20 ml). The combined organics were dried (MgSO$_4$), filtered and concentrated in vacuo. The obtained yellow solid was recrystallised from hexane and EtOAc to afford the product as a pale yellow solid (239 mg, 77%).

$^1$H NMR: (CDCl$_3$, 270 MHz): δ 2.72 (3H, s, NCOCH$_3$), 3.88 (3H, s, OMe), 7.00-7.05 (1H, dd, J=2.7, 9.1 Hz, ArH), 7.73 (1H, d, J=2.5 Hz, ArH), 8.01 (1H, s, ArH), 8.27 (1H, d, J=9.2 Hz, ArH), 10.08 ppm (1H, s, CHO).

Preparation of 1-(3-((2-(4-chlorophenoxy)phenylamino)methyl)-5-methoxy-1H-indol-1-yl)ethanone C$_{24}$H$_{21}$ClN$_2$O$_3$, Mol. Wt.: 420.89

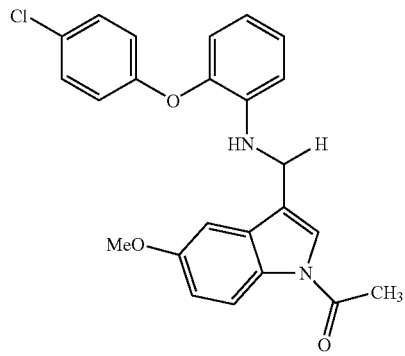 [SMILES: COc1ccc2c(c1)c(CNc1ccccc1Oc1ccc(Cl)cc1)cn2C(C)=O]

Similar procedure to the synthesis of 1-(3-((2-(4-chlorophenoxy)phenylamino)methyl)-1H-indol-1-yl)ethanone was followed however the product was purified by flash chromatography (eluant; 8:1 hexane:EtOAc to EtOAc). Once columned, spontaneous crystallisation occurred in the eluate and the solid was collected and recrystallised from hexane and EtOAc to afford the title compound as a white solid (HPLC, 99.21% 3.092 min (90% acetonitrile:10% water at 1.0 ml/min)) M. Pt. 141.5-142.5° C.

2$^{nd}$ batch: HPLC (98.82%, 3.099 min (90% acetonitrile: 10% water at 1.0 ml/min)), M. Pt. 140-141° C.

$^1$H NMR: (CDCl$_3$, 270 MHz): δ 2.53 (3H, s, CH$_3$), 3.78 (3H, s, OMe), 4.37 (3H, br s, NH, CH$_2$), 4.47 (2H, br s, CH2), 6.62-6.68 (1H, m, ArH), 6.80-7.00 (6H, m, ArH), 7.05-7.12 (1H, m, ArH), 7.20-7.25 (3H, m, ArH), 8.30 ppm (1H, d, J=9.2 Hz, ArH).

$^{13}$C NMR: (CDCl$_3$, 67.93 MHz): δ 23.8, 39.7, 55.7, 101.9, 112.1, 113.8, 117.6, 118.5, 119.6, 120.5, 123.7, 125.5, 127.0, 129.7, 129.8, 130.5, 139.1, 142.0, 143.5, 155.1, 156.2, 168.6 ppm.

LCMS: M$^+$Na: 443.18, 1.510 min (95% MeOH, 5% water at 1.0 ml/min).

HRMS (MicroTOF): C$_{24}$H$_{22}$ClN$_2$O$_3$ requires 421.1313, found 421.1297.

Preparation of N-(3-(1-(2-(4-Chlorophenoxy)phenylamino)ethyl)phenyl)acetamide

C$_{22}$H$_{21}$ClN$_2$O$_2$, MW 380.8673

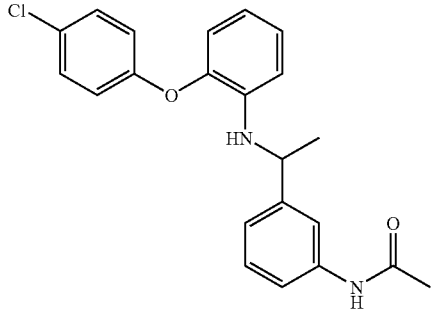 [SMILES: CC(=O)Nc1cccc(C(C)Nc2ccccc2Oc2ccc(Cl)cc2)c1]

2-(4-Chlorophenoxy)aniline (100 mg, 0.4552 mmol, 1.1 eq) and N-(3-acetylphenyl)acetamide (73 mg, 0.4120 mmol, 1 eq) were stirred in dry dichloromethane (DCM) at room temperature for 10 min. Tri-isopropoxytitanium chloride (215 μL, 0.9002 mmol, 2.2 eq) was added to the reaction mixture which was stirred at room temperature for an additional 10 min. Sodium triacetoxyborohydride (438 mg, 2.0667 mmol, 5 eq) and acetic acid (3 drops) were added to the reaction mixture which was stirred at room temperature for 16 h. The reaction mixture was then poured onto a solution of saturated aqueous sodium bicarbonate (100 mL) and extracted with DCM (120 mL). The organic layer was washed with brine (120 mL), dried over MgSO$_4$, filtered and concentrated to give the crude as a yellow foam. Purification of the crude by flash chromatography (ISCO) eluting with a gradient [from 100% petroleum ether (PE) to 100% EtOAc] gave the title compound (62 mg, 40%) as a white solid.

$^1$H NMR (270 MHz, CDCl$_3$) δ 1.45 (3H, d, J=7.0 Hz, CH$_3$), 2.09 (3H, s, CH$_3$), 4.39-4.52 (2H, m, CH+NH), 6.41-6.46 (1H, m, ArH), 6.51-6.60 (1H, m, ArH), 6.75-6.95 (5H, m, ArH), 7.01-7.08 (1H, m, ArH), 7.18-7.29 (2H, m, ArH), 7.35-7.42 (2H, m, ArH), 7.70 (1H, br s, NH); $^{13}$C NMR (67.5 MHz, CDCl$_3$) δ 24.7, 25.2, 53.2, 113.0, 117.0, 117.1, 118.6, 118.8, 119.2, 121.7, 125.3, 129.4, 129.7, 138.4, 139.4, 142.6, 146.3, 156.4, 168.5; LCMS (90% MeOH and 10% H$_2$O; Symmetry C$_{18}$ reverse phase column) t$_r$=2.25 min; (ES$^-$), m/z 381 ($^{35}$ClM$^-$, 75%), 383 ($^{37}$ClM$^-$, 25%); HRMS (ESI) calcd. for C$_{22}$H$_{22}$ClN$_2$O$_2$ (M+H)$^+$ 381.1364, found 381.1369.

Preparation of 1-Acetyl-N-(2-(1-(2-(4-chlorophenoxy)phenylamino)ethyl)phenyl)piperidine-4-carboxamide C$_{28}$H$_{30}$ClN$_3$O$_3$, MW 492.0091

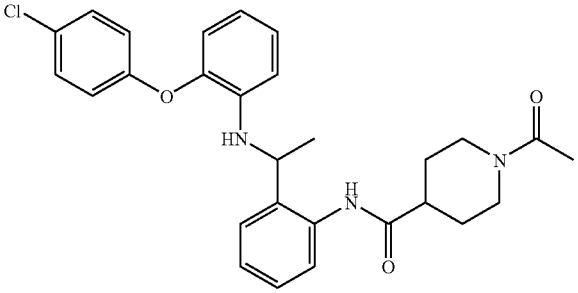 [SMILES: CC(=O)N1CCC(C(=O)Nc2ccccc2C(C)Nc2ccccc2Oc2ccc(Cl)cc2)CC1]

2-(4-Chlorophenoxy)aniline (25 mg, 0.1138 mmol, 1.1 eq) and 1-acetyl-N-(2-acetylphenyl)piperidine-4-carboxamide (30 mg, 0.1040 mmol, 1 eq) were stirred in dry dichloromethane (DCM) at room temperature for 10 min. Tri-isopropoxytitanium chloride (55 µL, 0.2303 mmol, 2.2 eq) was added to the reaction mixture which was stirred at room temperature for an additional 10 min. Sodium triacetoxyborohydride (110 mg, 0.5190 mmol, 5 eq) and acetic acid (3 drops) were added to the reaction mixture which was stirred at room temperature for 16 h. The reaction mixture was then poured onto a solution of saturated aqueous sodium bicarbonate (50 mL) and extracted with DCM (30 mL). The organic layer was washed with brine (50 mL), dried over $MgSO_4$, filtered and concentrated to give the crude as a yellow oil. Purification of the crude by flash chromatography (ISCO) eluting with a gradient [from 100% petroleum ether (PE) to 100% EtOAc] gave the title compound (5 mg, 10%) as a clear oil.

$^1$H NMR (270 MHz, $CDCl_3$) δ 1.44 (3H, d, J=7.5 Hz, $CH_3$), 1.63-1.68 (2H, m, $CH_2$), 1.82-1.98 (2H, m, $CH_2$), 2.02 (3H, s, $CH_3$), 2.38-2.45 (1H, m, CH), 2.65-2.69 (2H, m, $CH_2$), 3.09-3.21 (2H, m, $CH_2$), 4.40-4.48 (2H, m, CH+NH), 6.40-6.44 (1H, m, ArH), 6.51-6.58 (1H, m, ArH), 6.74-6.95 (4H, m, ArH), 7.05-7.11 (1H, m, ArH), 7.19-7.22 (3H, m, ArH), 7.35-7.49 (3H, m, NH+ArH); $^{13}$C NMR (67.5 MHz, $CDCl_3$) δ 21.6, 25.2, 41.0, 45.8, 53.2, 60.5, 113.0, 117.0, 117.1, 118.6, 118.8, 119.2, 119.3, 119.4, 119.6, 125.3, 129.5, 129.7, 129.8, 139.4, 142.6, 146.3, 168.5, 172.3; LCMS (90% MeOH and 10% $H_2O$; Symmetry $C_{18}$ reverse phase column) $t_r$=2.38 min; (ES$^-$), m/z 492 ($^{35}$ClM$^-$, 75%), 494 ($^{37}$ClM$^-$, 25%); HRMS (ESI) calcd. for $C_{28}H_{31}ClN_3O_3$ (M+H)$^+$ 492.2048, found 492.2038.

Preparation of 1-Acetyl-N-(3-(1-(2-(4-chlorophenoxy)phenylamino)ethyl)phenyl)piperidine-4-carboxamide $C_{28}H_{30}ClN_3O_3$, MW 492.0091

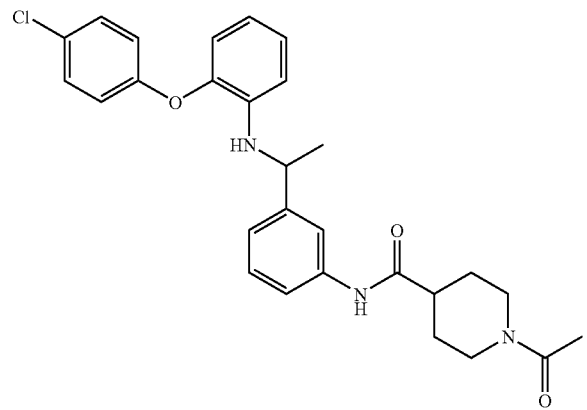 [SMILES: CC(=O)N1CCC(C(=O)Nc2cccc(C(C)Nc3ccccc3Oc3ccc(Cl)cc3)c2)CC1]

2-(4-Chlorophenoxy)aniline (137 mg, 0.6237 mmol, 1.1 eq) and 1-acetyl-N-(3-acetylphenyl)piperidine-4-carboxamide (160 mg, 0.5549 mmol, 1 eq) were stirred in dry dichloromethane (DCM) at room temperature for 10 min. Tri-isopropoxytitanium chloride (295 µL, 1.2351 mmol, 2.2 eq) was added to the reaction mixture which was stirred at room temperature for an additional 10 min. Sodium triacetoxyborohydride (590 mg, 2.7838 mmol, 5 eq) and acetic acid (3 drops) were added to the reaction mixture which was stirred at room temperature for 16 h. The reaction mixture was then poured onto a solution of saturated aqueous sodium bicarbonate (100 mL) and extracted with DCM (80 mL). The organic layer was washed with brine (100 mL), dried over $MgSO_4$, filtered and concentrated to give the crude as a yellow oil. Purification of the crude by flash chromatography (ISCO) eluting with a gradient [from 100% petroleum ether (PE) to 100% EtOAc] gave the title compound (48 mg, 18%) as a clear oil.

$^1$H NMR (270 MHz, $CDCl_3$) δ 1.43 (3H, d, J=7.0 Hz, $CH_3$), 1.60-1.95 (4H, m, 2×$CH_2$), 2.07 (3H, s, $CH_3$), 2.38-2.52 (1H, m, CH), 2.55-2.72 (2H, m, $CH_2$), 3.01-3.15 (2H, m, $CH_2$), 4.36-4.50 (2H, m, CH+NH), 6.40-6.48 (1H, m, ArH), 6.52-6.60 (1H, m, ArH), 6.75-6.95 (4H, m, ArH), 7.04-7.09 (1H, m, ArH), 7.19-7.28 (3H, m, ArH), 7.35-7.50 (2H, m, ArH), 7.78 (1H, br s, NH);

$^{13}$C NMR (67.5 MHz, $CDCl_3$) δ 21.6, 25.2, 41.0, 45.8, 53.3, 60.5, 113.0, 117.0, 117.1, 118.6, 118.8, 119.2, 119.4, 119.6, 125.3, 129.4, 129.7, 138.4, 139.4, 142.6, 146.4, 156.3, 169.1, 172.5; LCMS (90% MeOH and 10% $H_2O$; Symmetry $C_{18}$ reverse phase column) $t_r$=2.32 min; (ES$^-$), m/z 492 ($^{35}$ClM$^-$, 75%), 494 ($^{37}$ClM$^-$, 25%); HRMS (ESI) calcd. for $C_{28}H_{31}ClN_3O_3$ (M+H)$^+$ 492.2048, found 492.2051.

Preparation of N-(3-(1-(2-(4-Chlorophenoxy)phenylamino)ethyl)phenyl)-N-methylacetamide $C_{23}H_{23}ClN_2O_2$, MW 394.8939

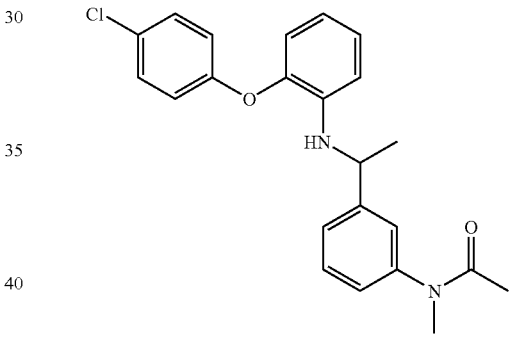

2-(4-Chlorophenoxy)aniline (95 mg, 0.4314 mmol, 1.1 eq) and N-(3-acetylphenyl)-N-methylacetamide (75 mg, 0.3922 mmol, 1 eq) were stirred in dry dichloromethane (DCM) at room temperature for 10 min. Tri-isopropoxytitanium chloride (187.4 µL, 0.7844 mmol, 2 eq) was added to the reaction mixture which was stirred at room temperature for 16 hours. Sodium triacetoxyborohydride (332.4 mg, 1.568 mmol, 4 eq) was then added to the reaction mixture and was stirred at room temperature for a further 24 h. The reaction mixture was then poured onto a solution of saturated aqueous sodium bicarbonate (100 mL) and extracted with DCM (120 mL).

The organic layer was washed with brine (120 mL), dried over $MgSO_4$, filtered and concentrated to give the crude as a yellow oil. Purification of the crude by flash chromatography (ISCO) eluting with a gradient [from 100% dichloromethane (DCM) to 5% MeOH in dichloromethane] gave (26 mg, 17%) as an off-white solid.

Mp 127-131° C.; $^1$H NMR (270 MHz, $CDCl_3$) δ 1.45 (3H, d, J=7.0 Hz, $CH_3$), 1.72 (3H, s, $CH_3$), 3.22 (3H, s, $NCH_3$), 4.51-4.60 (2H, m, CH and NH) 6.37 (1H, d, J=6.7 Hz, ArH), 6.59 (1H, dt, J=1.3, 6.7 Hz ArH), 6.75-6.97 (4H, m, ArH), 6.90-7.10 (2H, m, ArH), 7.22-7.39 (4H, m, ArH); $^{13}$C NMR (67.5 MHz, $CDCl_3$) δ 22.1, 25.2, 37.3, 53.5, 112.9, 117.2, 118.8, 119.2, 124.5, 125.0, 125.2, 125.4, 129.8, 130.0, 134.1, 138.9, 142.8, 145.0, 147.1, 156.2, 170.5 LCMS (90% MeOH and 10% H$_2$O; Symmetry C$_{18}$ reverse phase column) t$_r$=2.58 min; (ES$^+$), m/z 395.3 ($^{35}$ClM$^-$, 75%), 383 ($^{37}$ClM$^-$, 25%); HRMS (ESI) calcd. for C$_{23}$H$_{23}$ClN$_2$O$_2$ (M+H)$^+$ 395.1507, found 395.1511. Anal. calcd for C$_{23}$H$_{23}$ClN$_2$O$_2$; N, 7.09; C, 69.95; H, 5.87%. found N, 6.81; C, 69.8; H, 6.13%.

Preparation of N-(3-(1-(2-(4-Chlorophenoxy)phenylamino)ethyl)phenyl)-N-ethylacetamide C$_{24}$H$_{25}$ClN$_2$O$_2$, MW 408.9205

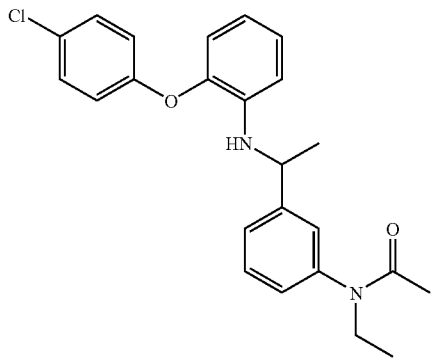 [SMILES: CCN(C(C)=O)c1cccc(C(C)Nc2ccccc2Oc2ccc(Cl)cc2)c1]

2-(4-Chlorophenoxy)aniline (200 mg, 0.9107 mmol, 1.1 eq) and N-(3-acetylphenyl)-N-ethylacetamide (169 mg, 0.827 mmol, 1 eq) were stirred in dry dichloromethane (DCM) at room temperature for 10 min. Tri-isopropoxytitanium chloride (395 µL, 1.654 mmol, 2 eq) was added to the reaction mixture which was stirred at room temperature for 16 hours. Sodium triacetoxyborohydride (700 mg, 3.308 mmol, 4 eq) was then added to the reaction mixture and was stirred at room temperature for a further 24 h. The reaction mixture was then poured onto a solution of saturated aqueous sodium bicarbonate (100 mL) and extracted with DCM (120 mL). The organic layer was washed with brine (120 mL), dried over MgSO$_4$, filtered and concentrated to give the crude as a yellow oil. Purification of the crude by flash chromatography (ISCO) eluting with a gradient [from 25% ethyl acetate in petrol ether to 50% ethyl acetate in petrol ether] gave (87 mg, 26%) as a white solid.

$^1$H NMR (270 MHz, CDCl$_3$) δ 1.05 (3H, t, J=8.1 Hz, CH$_3$), 1.49 (3H, d, J=6.4 Hz CH$_3$), 1.67 (3H, s, CH$_3$), 3.68 (2H, q, J=8.1 Hz, CH$_2$), 4.45-4.60 (2H, m, NH and CH) 6.37 (1H, d, J=8.2 Hz, ArH), 6.57 (1H, dt, J=1.4, 8.2 Hz ArH), 6.75-7.06 (6H, m, ArH), 7.23-7.39 (4H, m, ArH);

$^{13}$C NMR (67.5 MHz, CDCl$_3$) δ 13.1, 22.8, 25.0, 43.8, 52.8, 112.0, 112.9, 117.2, 118.7, 119.3, 125.0, 126.1, 126.5, 128.0, 129.8, 130.0, 138.0, 139.1, 142.8, 147.1, 156.5, 169.9 LCMS (90% MeOH and 10% H$_2$O; Symmetry C$_{18}$ reverse phase column) t$_r$=2.88 min; (ES$^+$), m/z 409.2 ($^{35}$ClM$^-$, 75%), 383 ($^{37}$ClM$^-$, 25%);

HRMS (ESI) calcd. for C$_{24}$H$_{25}$ClN$_2$O$_2$ (M+H)$^+$ 409.1605, found 409.1689. 99.48% purity.

Preparation of 1-Acetyl-N-(3-(1-(2-(4-chlorophenoxy)phenylamino)ethyl)phenyl)-N-ethylpiperidine-4-carboxamide C$_{30}$H$_{34}$ClN$_3$O$_3$, MW 520.0623

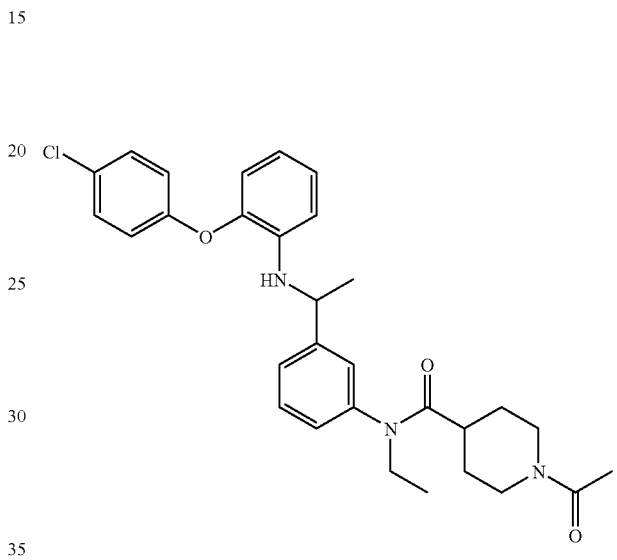

2-(4-Chlorophenoxy)aniline (95 mg, 0.431 mmol, 1 eq) and 1-acetyl-N-(3-acetylphenyl)-N-ethylpiperidine-4-carboxamide (150 mg, 0.474 mmol, 1.1 eq) were stirred in dry dichloromethane (DCM) (2 mL) at room temperature for 10 min. Tri-isopropoxytitanium chloride (206 µL, 1.654 mmol, 2 eq) was added to the reaction mixture which was stirred at room temperature for 16 hours. Sodium triacetoxyborohydride (365 mg, 1.724 mmol, 4 eq) was then added to the reaction mixture and was stirred at room temperature for a further 24 h. The reaction mixture was then poured onto a solution of saturated aqueous sodium bicarbonate (100 mL) and extracted with DCM (120 mL). The organic layer was washed with brine (120 mL), dried over MgSO$_4$, filtered and concentrated to give the crude as a yellow oil. Purification of the crude by flash chromatography (ISCO) eluting with a gradient [0-10% MeOH/DCM] gave as a pale yellow oil. $^1$H NMR (270 MHz, CDCl$_3$) δ 0.98 (3H, dt, J=3.1, 7.0 Hz, CH$_3$), 1.25 (1H, m, CH$_2$), 1.50 (3H, d, J=6.2 Hz CH$_3$), 1.50-1.71 (3H, m, CH$_2$), 1.95 (3H, d, J=7.2 Hz) 2.05-2.20 (2H, m, CH$_2$), 2.40 and 2.65 (1H, m, CH), 3.50-3.72 (3H, m, CH$_2$), 4.30-4.61 (3H, m, CH and NH), 6.32 (1H, d, J=7.8 Hz, ArH), 6.55 (1H, q, J=7.3 Hz, Ar), 6.70-6.90 (4H, m, Ar), 6.95-7.05 (2H, m, Ar), 7.20-7.42 (4H, m, Ar); LCMS (90% MeOH and 10% H$_2$O; Symmetry C$_{18}$ reverse phase column) t$_r$=2.38 min; (ES$^+$), m/z 520.3; HRMS (ESI) calcd. for C$_{30}$H$_{35}$ClN$_3$O$_3$ (M+H)$^+$ 520.2289, found 520.2343. HPLC 99.49% purity.

Preparation of 1-Acetyl-N-(3-(1-(2-(4-chlorophenoxy)phenylamino)ethyl)phenyl)-N-methylpiperidine-4-carboxamide $C_{29}H_{32}ClN_3O_3$, MW 506.0357

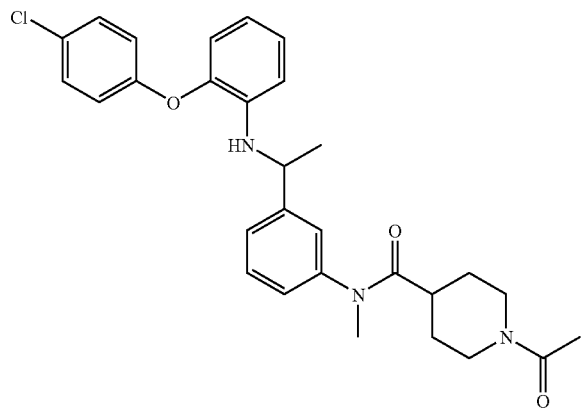 [SMILES: CC(=O)N1CCC(C(=O)N(C)c2cccc(C(C)Nc3ccccc3Oc3ccc(Cl)cc3)c2)CC1]

2-(4-Chlorophenoxy)aniline (118 mg, 0.541 mmol, 1 eq) and 1-acetyl-N-(3-acetylphenyl)-N-methylpiperidine-4-carboxamide (180 mg, 0.595 mmol, 1.1 eq) were stirred in dry dichloromethane (DCM) (2 mL) at room temperature for 10 min. Tri-isopropoxytitanium chloride (284 µL, 1.19 mmol, 2 eq) was added to the reaction mixture which was stirred at room temperature for 16 hours. Sodium triacetoxyborohydride (504 mg, 2.38 mmol, 4 eq.) was then added to the reaction mixture and was stirred at room temperature for a further 24 h. The reaction mixture was then poured into aqueous sodium bicarbonate (100 mL) and extracted with DCM (120 mL). The organic layer was washed with brine (120 mL), dried over MgSO₄, filtered and concentrated to give the crude as a yellow oil. Purification of the crude by flash chromatography (ISCO) eluting with a gradient [0-10% MeOH/DCM] gave (167 mg, 61%) as a white foam. $^1$H NMR (270 MHz, CDCl$_3$) δ 1.2-1.38 (2H, m, CH$_2$), 1.50 (3H, d, J=6.1 Hz, CH$_3$), 1.55-1.80 (2H, m, CH$_2$), 1.90 (3H, d, J=6.7 Hz CH$_3$), 2.10-2.30 (2H, m, CH$_2$), 2.39 and 2.65 (1H, m, CH$_2$), 3.15 (3H, s, NCH$_3$), 3.69 and 3.49 (1H, d, J=13.4 Hz, CH), 4.25-4.60 (3H, m, NH and CH), 6.30 (1H, d, J=8.0 Hz, Ar) 6.55 (1H, q, J=7.0 Hz, ArH), 6.75-6.95 (4H, m, ArH), 7.00-7.15 (2H, m, ArH), 7.23-7.51 (4H, m, ArH); LCMS (90% MeOH and 10% H$_2$O; Symmetry C$_{18}$ reverse phase column) t$_r$=2.15 min; (ES$^+$), m/z 506.4 HRMS (ESI) calcd. for C$_{29}$H$_{32}$ClN$_3$O$_3$ (M+H)$^+$ 505.2132, found 506.2193. HPLC 100% purity.

Preparation of 1-(3-(1-(2-(4-Chlorophenoxy)phenylamino)ethyl)phenyl)pyrrolidin-2-one $C_{24}H_{23}ClN_2O_2$, MW 406.9041

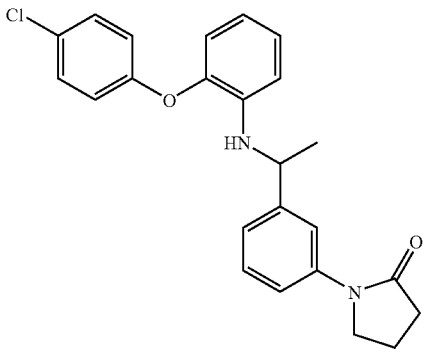 [SMILES: CC(Nc1ccccc1Oc1ccc(Cl)cc1)c1cccc(N2CCCC2=O)c1]

2-(4-Chlorophenoxy)aniline (245 mg, 1.118 mmol, 1 eq) and 1-acetyl-N-(3-acetylphenyl)-N-ethylpiperidine-4-carboxamide (250 mg, 1.230 mmol, 1.1 eq) were stirred in dry dichloromethane (DCM) (2 mL) at room temperature for 10 min. Tri-isopropoxytitanium chloride (534 µL, 2.236 mmol, 2 eq) was added to the reaction mixture which was stirred at room temperature for 16 hours. Sodium triacetoxyborohydride (947 mg, 4.472 mmol, 4 eq) was then added to the reaction mixture and was stirred at room temperature for a further 24 h. The reaction mixture was then poured into saturated aqueous sodium bicarbonate (100 mL) and extracted with DCM (120 mL). The organic layer was washed with brine (120 mL), dried over MgSO₄, filtered and concentrated to give the crude as a yellow oil. Purification of the crude by flash chromatography (ISCO) eluting with a gradient [0-10% MeOH/DCM] gave (437 mg, 91%) as a pale yellow oil. $^1$H NMR (270 MHz, CDCl$_3$) δ 1.45 (3H, d, J=8.1 Hz, CH$_3$), 2.02-2.18 (2H, m, CH$_2$), 2.58 (2H, t, J=10.8 Hz, CH$_2$), 3.77 (2H, t, J=9.7 Hz, CH$_2$), 4.50 (2H, m, NH and CH), 6.47-6.62 (2H, m, Ar) 6.77-6.96 (4H, m, Ar), 7.09 (1H, d, J=8.1 Hz, Ar), 7.22-7.32 (3H, m, Ar), 7.48 (1H, dd, J=2.4, 8.1 Hz, Ar), 7.59 (1H, m, Ar). LCMS (90% MeOH and 10% H$_2$O; Symmetry C$_{18}$ reverse phase column) t$_r$=2.73 min; (ES$^+$), m/z 407.2. HPLC 98.56% purity.

Biology

Assay Protocol-17β-Hydroxysteroid Dehydrogenase Type 3 Activity in the Presence of Regulatory Agents 293-EBNA cells stably transfected with 17β-HSD Type 3 were plated at 50,000 cells/well in 24 well plates in complete growth medium. After 48 hours 2-3 nM $^3$H-Androstenedione in assay medium (500 ml DMEM medium with 5 ml 100×L-Glutamine, and 5 ml 7.5% sodium bicarbonate solution) was added with or without test compound at 1.5 ml/well (triplicate), and the cells incubated at 37° C.

Two hours later 1 ml medium was removed from each well and placed in a 125×16 mm glass test tube containing 25 µl of recovery solution (5000 dpm $^{14}$C-Testosterone and 25 µg unlabelled Testosterone). Ether (4 ml) was added and the tubes vortexed at high speed for 2×30 sec. After the samples had settled into two phases they were snap-frozen in a dry ice/methanol bath. The upper organic phase was decanted into 75×12 mm tubes and evaporated to dryness under an airstream using a sample concentrator (TECHNE) at 40° C. The samples were resuspended in ether (8 drops, then a further 3), spotted onto silica 60 F254 20 cm×20 cm TLC plates, and separated using a 4:1 v/v dichloromethane:ethyl acetate mobile phase.

After drying the plates, the major spots were marked under a UV lamp, cut out, and placed in individual scintillation vials containing 0.5 ml methanol. These were then shaken lightly and allowed to stand for 15 min before adding 10 ml of EcoScint A (scintillation fluid) to each tube along with 0.5 ml assay medium, and counted in a scintillation spectrometer (Beckman) using a program for dual [$^3$H/$^{14}$C] isotopes. The number of cells/well was then counted using a Coulter counter (Beckman).

The inhibitory activity of the test compounds is then assessed by calculating the amount of product formed correcting for crossover between isotope counts, recovery, dilution and non-enzymatic degradation (fmol/hr/million cells) with and without inhibitor, (% inhibition).

Inhibition Data

The structures of representative examples of the above synthesised compounds and the data obtained are given in the table below.

Compounds were tested at 10 μM for inhibition of human 17β-HSD3 with typically ~200,000 to 300,000 human 293-EBNA cells/well. Compounds showing >60% inhibition of 17β-HSD3 when tested at 10 μM using the above protocol have been designated (A) in the table, those showing from 20 to 60% inhibition of 17β-HSD3 when tested at 10 μM using the same protocol have been designated (B) in the table, and those showing less than 20% inhibition of 17β-HSD3 when tested at 10 μM using the same protocol have been designated (C) in the table below.

| Structure | % Inhibition (at 10 μM)a |
|---|---|
| | A |
| | A |
| | A |

-continued

| Structure | % Inhibition (at 10 μM)a |
|---|---|
| (4-chlorophenoxy-phenyl)-aminomethyl benzodioxole acetamide structure | A |
| (4-chlorophenoxy-phenyl)-aminomethyl-4,5-dimethoxyphenyl acetamide structure | C |
| (2,4-dichlorophenoxy-phenyl)-aminomethyl-4,5-dimethoxyphenyl acetamide structure | C |
| (4-chlorophenoxy-phenyl)-aminomethyl naphthyl acetamide structure | C |

-continued

| Structure | % Inhibition (at 10 μM)a |
|---|---|
| (structure) | A |
| (structure) | A |
| (structure) | B |
| (structure) | A |
| (structure) | C |

-continued

| Structure | % Inhibition (at 10 μM)a |
|---|---|
| (structure) | C |
| (structure) | A |
| (structure) | B |
| (structure) | C |
| (structure) | C |

-continued

| Structure | % Inhibition (at 10 μM)a |
|---|---|
| (4-chlorophenoxy)-phenyl-NH-CH2-phenyl-NHC(O)CH3 | B |
| (2,4-dichlorophenoxy)-phenyl-NH-CH2-phenyl-NHC(O)CH3 | C |
| (4-chlorophenoxy)-phenyl-NH-CH2-(3-acetamidophenyl) | B |
| (4-chlorophenoxy)-phenyl-N(C(O)CH3)-CH2-phenyl-NH-(1-acetylpiperidin-4-yl) | B |

-continued
| Structure | % Inhibition (at 10 μM)a |
|---|---|
| 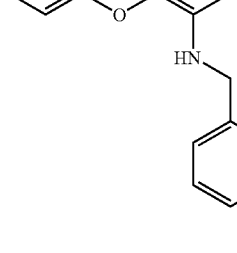 | B |
| 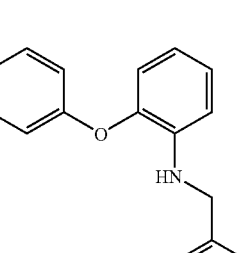 | A |
| 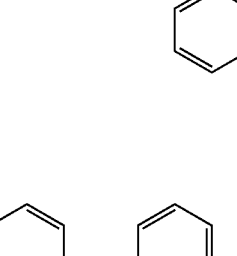 | A |
| 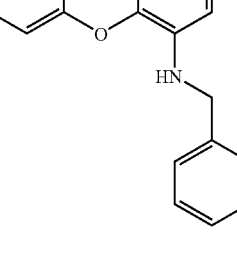 | B |

-continued

| Structure | % Inhibition (at 10 μM)a |
|---|---|
| (4-chlorophenoxy-phenyl)-NH-CH(-)-phenyl-N(Et)-C(=O)CH₃ | A |
| (4-chlorophenoxy-phenyl)-NH-CH(allyl)-phenyl-NHC(=O)CH₃ | A |
| (4-chlorophenoxy-phenyl)-NH-CH(allyl)-phenyl-NHC(=O)CH₃, R-(-)- | B |
| (4-chlorophenoxy-phenyl)-NH-CH(allyl)-phenyl-NHC(=O)CH₃, S-(+)- | A |
| (4-chlorophenoxy-phenyl)-NH-CH(benzyl)-phenyl-NHC(=O)CH₃ | C |

-continued

| Structure | % Inhibition (at 10 μM)a |
|---|---|
| 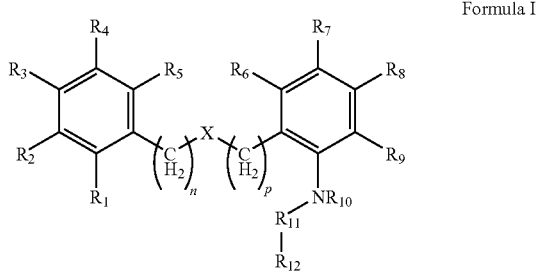 | A |
| | A | aResults obtained from the TLC assay. Mean of at least 2 measurements with typically a SD of ±5%.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry or related fields are intended to be within the scope of the following claims.

The invention claimed is:

1. A compound having Formula

Formula I wherein each of $R_1$, $R_2$, $R_3$, $R_4$, $R_5$, $R_6$, $R_7$, $R_8$ and $R_9$ are independently selected from:
(a) H; (b) $R_{13}$, —OC($R_{13}$)$_3$, —OCH($R_{13}$)$_2$, —OCH$_2$$R_{13}$, —C($R_{13}$)$_3$, —CH($R_{13}$)$_2$, or —CH$_2$$R_{13}$ wherein $R_{13}$ is a halogen; (c) —CN; (d) optionally substituted alkyl, (e) optionally substituted heteroalkyl; (f) optionally substituted aryl; (g) optionally substituted heteroaryl;
(h) optionally substituted arylalkyl; (i) optionally substituted heteroarylalkyl;
(j) hydroxy; (k) alkoxy; (l) aryloxy; (m)-SO$_2$-alkyl; or (n) —N($R_{14}$)C(O)$R_{15}$,
wherein $R_{14}$ and $R_{15}$ are independently selected from H; an alkyl group, an alkenyl group, an alkynyl group, any of which may be linear, branched or cyclic; or an aryl group, wherein the optional substituents of (d), (e), (f), (h), and (i) are $C_{1-6}$ alkyl, halo, cyano, nitro, haloalkyl, hydroxy, $C_{1-6}$ alkoxy, carboxy, carboxyalkyl, carboxamide, mercapto, amino, alkylamino, dialkylamino, sulfonyl, sulfonamido, aryl or heteroaryl;
wherein n and p are 0;
X is O,
$R_{10}$ is selected from H, alkyl, or acyl groups,
$R_{11}$ is selected from $CR_{19}R_{20}$, in which $R_{19}$ and $R_{20}$ are independently selected from H, alkyl, alkenyl or alkylaryl groups,
$R_{12}$ is selected from a substituted five or six membered carbon rings optionally comprising one or more hetero atoms selected from N, S, or O and optionally having fused thereto a further ring, and wherein the one or more substituent is at least selected from an amide group.

2. The compound of claim 1 wherein each of $R_1$, $R_2$, $R_3$, $R_4$, $R_5$, $R_6$, $R_7$, $R_8$ and $R_9$ are independently selected from
(a) H or
(b) $R_{13}$, —OC($R_{13}$)$_3$, —OCH($R_{13}$)$_2$, —OCH$_2$$R_{13}$, —C($R_{13}$)$_3$, —CH($R_{13}$)$_2$, or —CH$_2$$R_{13}$, wherein $R_{13}$ is a halogen.

3. The compound of to claim 1 wherein $R_{13}$ is Cl or F.

4. The compound of claim 1 wherein (b) is F, Cl, —OCF$_3$, —OCHF$_2$, —OCH$_2$F, —CF$_3$, —CHF$_2$, or —CH$_2$F.

5. The compound of claim 1 wherein (b) is F, Cl or OCF$_3$.

6. The compound of claim 1 wherein $R_1$ is H or Cl.

7. The compound of claim 1 wherein $R_2$ is H.

8. The compound of claim 1 wherein $R_3$ is Cl or OCF$_3$.

9. The compound of claim 1 wherein $R_4$ is H.

10. The compound of claim 1 wherein $R_5$ is H.

11. The compound of claim 1 wherein $R_6$ is H.

12. The compound of claim 1 wherein $R_7$ is H.

13. The compound of claim 1 wherein $R_8$ is H or F.

14. The compound of claim 1 wherein $R_1$ is H or Cl, $R_3$ is Cl or $OCF_3$, $R_8$ is H or F, and $R_2$, $R_4$, $R_5$, $R_6$ and $R_7$ are each H.

15. The compound of claim 1 wherein $R_{10}$ is H, methyl ($—CH_3$) or acetyl ($—CO—CH_3$) groups.

16. The compound of claim 1 wherein $R_{19}$ and $R_{20}$ are independently selected from H, $C_{1-6}$ alkyl, $C_{1-6}$ alkenyl or $C_{1-6}$ alkyl phenyl groups.

17. The compound of claim 1 wherein $R_{19}$ and $R_{20}$ are independently selected from H, $—CH_3$, $—CH_2CH_2CH_3$, $—CH_2CH=CH_2$, or $—CH_2$-Ph.

18. The compound of claim 1 wherein $R_{20}$ is H and $R_{19}$ is H, $—CH_3$, $—CH_2CH_2CH_3$, $—CH_2CH=CH_2$, or $—CH_2$-Ph.

19. The compound of claim 1 wherein $R_{20}$ is H and $R_{19}$ is $—CH_3$, $—CH_2CH_2CH_3$, $—CH_2CH=CH_2$, or $—CH_2$-Ph.

20. The compound of claim 1 wherein $R_{12}$ is a substituted aryl ring, optionally having fused thereto a further ring.

21. The compound of claim 1 wherein $R_{12}$ is a substituted carbocyclic ring, optionally having fused thereto a further ring.

22. The compound of claim 1 wherein $R_{12}$ is a substituted six membered carbocyclic ring, optionally having fused thereto a further ring.

23. The compound of claim 1 wherein $R_{12}$ is a substituted phenyl ring, optionally having fused thereto a further ring.

24. The compound of claim 1 wherein the optional fused ring of $R_{12}$ is selected from a substituted five or six membered carbon rings optionally comprising one or more hetero atoms of N, S, or O.

25. The compound of claim 1 wherein the $R_{12}$ is a substituted five or six membered carbon rings, wherein the one or more substituents are at least selected from amide groups.

26. The compound of claim 25 wherein the one or more substituents are at least selected from $—NR_{21}—CO—R_{22}$, wherein $R_{21}$ and $R_{22}$ are independently selected from H, phenyl or $C_{1-10}$ alkyl groups.

27. The compound of claim 25 wherein the one or more substituents are at least selected from $—NR_{21}—CO—R_{22}$, wherein $R_{21}$ and $R_{22}$ are independently selected from H, phenyl or $C_{1-10}$ alkyl groups.

28. The compound of claim 26 wherein $R_{21}$ and $R_{22}$ are independently selected from H, methyl or phenyl.

29. The compound according to claim 25 wherein the one or more substituents are at least selected from $—NH—CO-Me$.

30. The compound of claim 1 wherein the compound is of Formula II

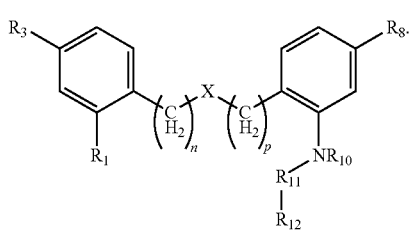

Formula II

31. The compound of claim 1 wherein the compound is of Formula III

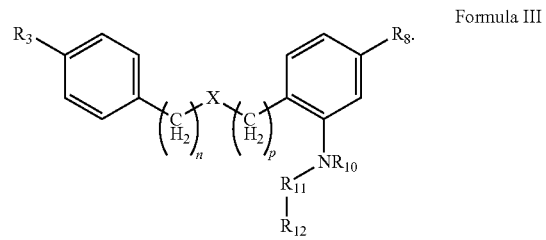

Formula III

32. The compound of claim 1 wherein the compound is of Formula IV

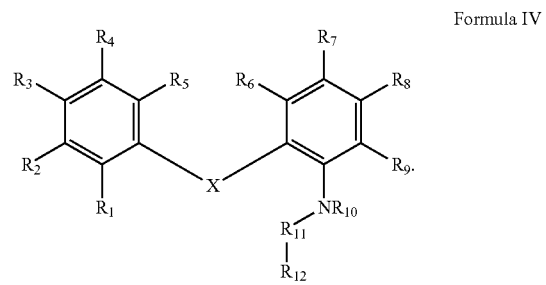

Formula IV

33. The compound of claim 1 wherein the compound is of Formula V

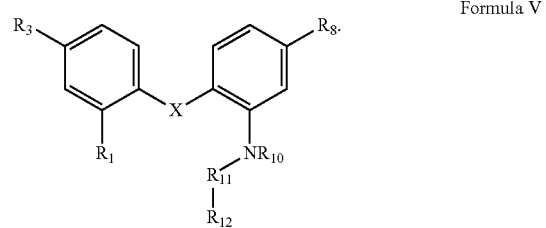

Formula V

34. The compound of claim 1 wherein the compound is of Formula VI

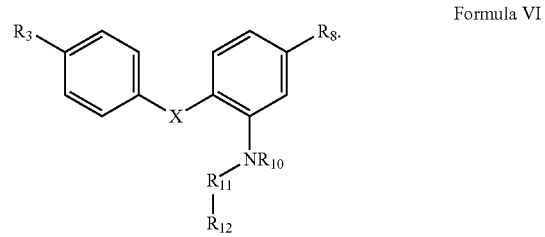

Formula VI

35. The compound of claim 1 wherein the compound is of Formula VII

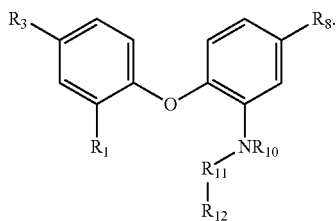

Formula VII

36. The compound of claim 1 wherein the compound is of Formula VIII

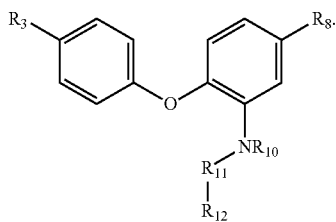

Formula VIII

37. A pharmaceutical composition comprising a compound of claim 1 optionally admixed with a pharmaceutically acceptable carrier, diluent, excipient or adjuvant.

38. A medicinal compound comprising the compound of claim 1.

39. The compound of claim 27 wherein $R_{21}$ and $R_{22}$ are independently selected from H, phenyl or $C_{1-10}$ alkyl groups.

40. The compound of claim 27 wherein $R_{21}$ and $R_{22}$ are independently selected from H, methyl or phenyl.

41. The compound of claim 1, wherein $R_{12}$ further comprises one or more alkyl group, alkoxy group, or halogen.

42. A compound having a formula of

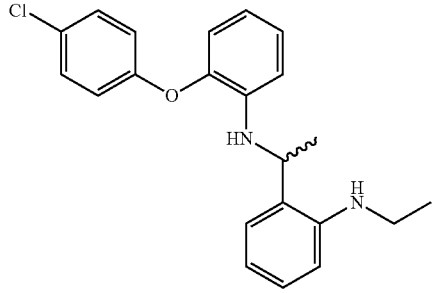

43. A pharmaceutical composition comprising a compound of claim 42 optionally admixed with a pharmaceutically acceptable carrier, diluent, excipient or adjuvant.

44. A medicinal compound comprising the compound of claim 42.

* * * * *

UNITED STATES PATENT AND TRADEMARK OFFICE
CERTIFICATE OF CORRECTION

PATENT NO. : 8,558,028 B2
APPLICATION NO. : 12/744044
DATED : October 15, 2013
INVENTOR(S) : Vicker et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 125 days.

Signed and Sealed this
Fifteenth Day of September, 2015

Michelle K. Lee
*Director of the United States Patent and Trademark Office*